United States Patent
Uemoto et al.

(10) Patent No.: US 9,290,440 B2
(45) Date of Patent: Mar. 22, 2016

(54) BICYCLIC COMPOUND

(71) Applicant: TOA EIYO LTD., Chuo-ku (JP)

(72) Inventors: Kazuhiro Uemoto, Kawaguchi (JP); Yoshimichi Sato, Ageo (JP); Naoki Okada, Ageo (JP); Emiko Iimori, Ota-ku (JP); Masayuki Kageyama, Kawaguchi (JP)

(73) Assignee: TOA EIYO LTD., Chuo-ku (JP)

( * ) Notice: Subject to any disclaimer, the term of this patent is extended or adjusted under 35 U.S.C. 154(b) by 0 days.

(21) Appl. No.: 14/394,652

(22) PCT Filed: Apr. 15, 2013

(86) PCT No.: PCT/JP2013/061231
§ 371 (c)(1),
(2) Date: Oct. 15, 2014

(87) PCT Pub. No.: WO2013/157528
PCT Pub. Date: Oct. 24, 2013

(65) Prior Publication Data
US 2015/0119418 A1 Apr. 30, 2015

(30) Foreign Application Priority Data

Apr. 16, 2012 (JP) ................................ 2012-092783

(51) Int. Cl.
| | |
|---|---|
| *A61K 31/47* | (2006.01) |
| *C07D 217/00* | (2006.01) |
| *C07D 215/00* | (2006.01) |
| *C07C 229/38* | (2006.01) |
| *C07D 311/04* | (2006.01) |
| *C07D 311/58* | (2006.01) |
| *C07D 311/76* | (2006.01) |
| *C07D 215/48* | (2006.01) |
| *C07D 317/54* | (2006.01) |
| *C07D 319/18* | (2006.01) |
| *C07D 333/56* | (2006.01) |
| *C07D 335/06* | (2006.01) |
| *C07C 229/50* | (2006.01) |

(Continued)

(52) U.S. Cl.
CPC .............. *C07C 229/38* (2013.01); *C07C 229/50* (2013.01); *C07C 255/24* (2013.01); *C07C 311/19* (2013.01); *C07C 311/20* (2013.01); *C07C 311/21* (2013.01); *C07C 323/16* (2013.01); *C07C 323/19* (2013.01); *C07D 215/48* (2013.01); *C07D 217/26* (2013.01); *C07D 257/04* (2013.01); *C07D 307/82* (2013.01); *C07D 311/04* (2013.01); *C07D 311/58* (2013.01); *C07D 311/68* (2013.01); *C07D 311/76* (2013.01); *C07D 317/54* (2013.01); *C07D 319/18* (2013.01); *C07D 333/56* (2013.01); *C07D 335/06* (2013.01); *C07C 2101/02* (2013.01); *C07C 2101/14* (2013.01); *C07C 2102/10* (2013.01); *C07C 2102/32* (2013.01)

(58) Field of Classification Search
None
See application file for complete search history.

(56) References Cited

U.S. PATENT DOCUMENTS

| 2,573,644 | A | 10/1951 | Kerwin et al. |
| 7,087,644 | B1 | 8/2006 | Alonso-Alija et al. |

(Continued)

FOREIGN PATENT DOCUMENTS

| CA | 2 879 456 A1 | 1/2014 |
| TW | 201028152 A1 | 8/2010 |

(Continued)

OTHER PUBLICATIONS

Harald H.H.W. Schmidt, et al., "NO- and Haem-Independent Soluble Guanylate Cyclase Activators", Handbook of Experiment Pharmacology, vol. 191, pp. 309-339, (2009).

(Continued)

*Primary Examiner* — Heidi Reese
(74) *Attorney, Agent, or Firm* — Oblon, McClelland, Maier & Neustadt, L.L.P.

(57) ABSTRACT

Provided is a pharmaceutical agent containing a compound represented by General Formula (1), a pharmaceutically acceptable salt thereof, or a solvate thereof:

General Formula (1)

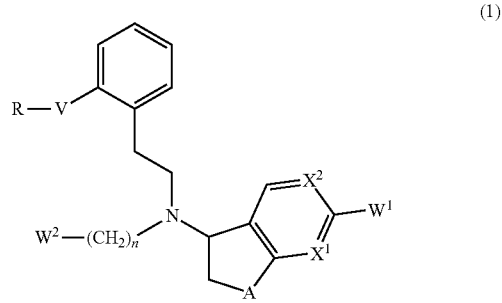

(1)

wherein A represents a $C_1$-$C_3$ linear alkylene group, in which one methylene group is optionally substituted with O or S;
n represents an integer of from 3 to 5;
$X^1$ and $X^2$ each independently represent CH or N;
$W^1$ and $W^2$ each independently represent a carboxyl group or a tetrazolyl group;
V represents a $C_1$-$C_8$ linear or branched alkylene group, in which one methylene group is optionally substituted with O or S; and
R represents a substituted phenyl group, for example.

10 Claims, No Drawings

(51) Int. Cl.

| | |
|---|---|
| *C07D 257/04* | (2006.01) |
| *C07D 307/82* | (2006.01) |
| *C07C 311/19* | (2006.01) |
| *C07C 311/20* | (2006.01) |
| *C07C 311/21* | (2006.01) |
| *C07C 323/16* | (2006.01) |
| *C07C 323/19* | (2006.01) |
| *C07C 255/24* | (2006.01) |
| *C07D 217/26* | (2006.01) |
| *C07D 311/68* | (2006.01) |

(56) References Cited

U.S. PATENT DOCUMENTS

| | | | |
|---|---|---|---|
| 2006/0052397 | A1 | 3/2006 | Alonso-Alija et al. |
| 2006/0063760 | A1 | 3/2006 | Wang et al. |
| 2006/0094769 | A1 | 5/2006 | Alonso-Alija et al. |
| 2009/0203906 | A1 | 8/2009 | Alonso-Alija et al. |
| 2009/0209556 | A1 | 8/2009 | Bittner et al. |
| 2010/0317854 | A1 | 12/2010 | Alonso-Alija et al. |
| 2011/0028493 | A1 | 2/2011 | Matsunaga et al. |
| 2011/0118282 | A1 | 5/2011 | Bittner et al. |
| 2011/0245273 | A1 | 10/2011 | Schirok et al. |
| 2013/0203751 | A1 | 8/2013 | Hübsch et al. |
| 2014/0031391 | A1 | 1/2014 | Hahn et al. |
| 2014/0088080 | A1 | 3/2014 | Koga et al. |
| 2015/0148376 | A1 | 5/2015 | Hahn et al. |

FOREIGN PATENT DOCUMENTS

| | | |
|---|---|---|
| WO | 01 19780 | 3/2001 |
| WO | 03 095451 | 11/2003 |
| WO | 2009 032249 | 3/2009 |
| WO | 2009 071504 | 6/2009 |
| WO | 2009 123316 | 10/2009 |
| WO | 2010 078900 | 7/2010 |
| WO | WO 2011/141409 A1 | 11/2011 |
| WO | WO 2014/012934 A1 | 1/2014 |
| WO | WO 2014/012935 A1 | 1/2014 |

OTHER PUBLICATIONS

Johannes-Peter Stasch, et al., "No-Independent, Haem-Dependent Soluble Guanylate Cyclase Stimulators", Handbook of Experiment Pharmacology, vol. 191, pp. 277-308, (2009).

John D. Parker, "Nitrate tolerance, oxidative stress, and mitochondrial function: another worrisome chapter on the effects of organic nitrates", Journal of Clinical Investigation, vol. 113, No. 3, pp. 352-254, (Feb. 2004).

Johannes-Peter Stasch, et al., "Targeting the heme-oxidized nitric oxide receptor for selective vasodilatation of diseased blood vessels", Journal of Clinical Investigation, vol. 116, No. 9, pp. 2552-2561, (Sep. 2006).

R.T. Schermuly, et al., "Expression and function of soluble guanylate cyclase in pulmonary arterial hypertension", European Respiratory Journal, vol. 32, No. 4, pp. 881-891, (2008).

International Search Report and Written Opinion Issued Jun. 18, 2013 in PCT/JP13/061231 Filed Apr. 15, 2013.

Extended European Search Report issued Jun. 12, 2015 in Patent Application No. 13778508.5.

BICYCLIC COMPOUND

FIELD OF THE INVENTION

The present invention relates to a bicyclic compound having a heme-independent activating function for soluble guanylate cyclase and a pharmaceutical agent containing the same.

BACKGROUND OF THE INVENTION

Soluble guanylate cyclase (sGC) is an enzyme which produces cyclic guanosine monophosphate (cGMP) from guanosine triphosphate (GTP), and which consists of a dimer of α subunit and β subunit. The β subunit binds heme, and the iron coordinated to the heme generally interacts with the histidine residue as $105^{th}$ amino acid to have an inactivated structure. Nitrogen monoxide (NO) is known to be an major sGC stimulating factor in vivo, and according to interaction with the heme iron which is present in β subunit of sGC and dissociating the interaction between the heme iron and the histidine residue of β subunit, it promotes conversion into activated form. cGMP produced by activated sGC subsequently activates, for example, a protein kinase, or an ion channel to play various roles including relaxing vascular smooth muscle, suppressing platelet activation, suppressing cell proliferation, and olfactory neuronal transmission. Under pathological condition, activity of sGC is lowered and decomposition of sGC occurs to suppress the cGMP system, thus leading to contraction of, for example, vascular smooth muscle, activation of platelet, or cell proliferation. Eventually, it may cause, for example, hypertension, pulmonary hypertension, heart failure, endothelial function disorder, atherosclerosis, peripheral vascular disease, angina pectoris, thrombosis, myocardial infarction, erectile dysfunction, or renal function disorder (Non Patent Documents 1 and 2).

For activating sGC, nitrates such as nitroglycerin are widely used in clinical use. They induce the activation of sGC by supplying exogenous NO, and thus exhibit a pharmaceutical effect. However, the nitrate agents are known to have a tolerance in addition to side effects, which is a significant problem of the pharmaceutical agent. It has been suggested that the tolerance to the nitrate agents are based on a mechanism such as reduced activity of mitochondrial aldehyde dehydrogenase involved with NO release, which is different from sGC (Non Patent Document 3). Thus, a compound directly activating sGC without being related to NO release can avoid the tolerance. Further, under disease state such as aging, hypertension, diabetes, or hyperlipidemia, it has been shown that oxidation of heme iron or decomposition of heme is enhanced by oxidative stress to prevent the interaction between NO and heme, and thus it cannot be expected to have sufficient activation of sGC (Non Patent Document 4). As an sGC stimulating agent other than NO, a heme-dependent direct sGC stimulating agent represented by Riociguat (Patent Document 1) is known. Those compounds can activate sGC independing on NO, however, it is described that they cannot fully exhibit the sGC activating property under condition for oxidizing heme iron (Non Patent Document 5). Thus, unlike NO or Riociguat, a compound having a function of directly activating sGC without depending on oxidation state of heme is believed to be effective for treatment or prevention of various disorders such as hypertension, pulmonary hypertension, heart failure, endothelial function disorder, atherosclerosis, peripheral vascular disease, angina pectoris, thrombosis, myocardial infarction, erectile dysfunction, and renal function disorder.

As a compound having a function of directly activating sGC without depending on oxidation state of heme, Cinaciguat and derivatives thereof are disclosed in Patent Document 2, pyrazole, triazole derivatives are disclosed in Patent Document 3, 2,6-disubstituted pyridine derivatives are disclosed in Patent Document 4, and heterocyclic derivatives are disclosed in Patent Document 5.

CITATION LIST

Patent Documents

Patent Document 1: WO 2003/095451 A
Patent Document 2: WO 2001/019780 A
Patent Document 3: WO 2009/032249 A
Patent Document 4: WO 2009/071504 A
Patent Document 5: WO 2009/123316 A Non Patent Documents Non Patent Document 1: Handbook of Experimental Pharmacology, Germany, Springer-Verlag, 2009, Vol. 191, p. 309-339
Non Patent Document 2: Handbook of Experimental Pharmacology, Germany, Springer-Verlag, 2009, Vol. 191, p. 277-308
Non Patent Document 3: The Journal of Clinical Investigation, USA, American Society for Clinical Investigation, 2004, Vol. 113, p. 352-354
Non Patent Document 4: The Journal of Clinical Investigation, USA, American Society for Clinical Investigation, 2006, Vol. 116, p. 2552-2561
Non Patent Document 5: European Respiratory Journal, Switzerland, European Respiratory Society, 2008, Vol. 32, p. 881-891

SUMMARY OF THE INVENTION

Problems to be Solved by the Invention

An object of the present invention is to provide a novel compound which has a heme-independent activating function for soluble guanylate cyclase and is useful as a pharmaceutical product.

Means for Solving the Problem

Under the circumstances, the inventors of the present invention synthesized various compounds and evaluated them using the soluble guanylate cyclase activating function as an indicator. As a result, it was found that a compound having a structure that a bicyclic compound connected to a nitrogen atom has a high heme-independent property, an excellent function of activating soluble guanylate cyclase, and is useful as a pharmaceutical agent for prevention or treatment of various disorders that are related with soluble guanylate cyclase, and the inventors completed the present invention accordingly.

Specifically, the present invention is to provide a compound represented by General Formula (1), a pharmaceutically acceptable salt thereof, or a solvate thereof:

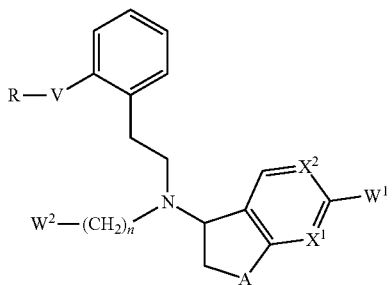

(1)

wherein A represents a $C_1$-$C_3$ linear alkylene group, wherein one methylene group is optionally substituted with O or S;
n represents an integer of from 3 to 5;
$X^1$ and $X^2$ each independently represent CH or N;
$W^1$ and $W^2$ each independently represent a carboxyl group or a tetrazolyl group;
V represents a $C_1$-$C_8$ linear or branched alkylene group, in which one methylene group is optionally substituted with O or S;
R represents a group selected from the followings:

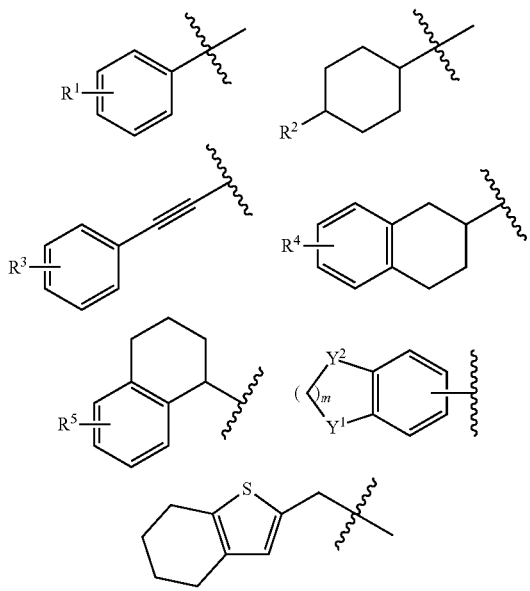

in which $R^1$, $R^2$, $R^3$, $R^4$ and $R^5$ represent a hydrogen atom, a halogen atom, a $C_1$-$C_6$ alkyl group which may have a substituent group, a $C_1$-$C_6$ alkoxy group, a $C_3$-$C_6$ cycloalkyl group, a $C_3$-$C_6$ cycloalkoxy group, a halo $C_1$-$C_4$ alkyl group, a halo $C_1$-$C_4$ alkoxy group, a vinyl group which may have a substituent group, an ethynyl group which may have a substituent group, an aryl group which may have a substituent group on an aromatic ring, an aryloxy group which may have a substituent group on an aromatic ring, a benzyl group which may have a substituent group on a benzene ring, a phenethyl group which may have a substituent group on a benzene ring, a benzyloxy group which may have a substituent group on a benzene ring, a benzylsulfanyl group which may have a substituent group on a benzene ring, a benzylamino group which may have a substituent group on a benzene ring, a phenyloxymethyl group which may have a substituent group on a benzene ring, a phenylsulfanylmethyl group which may have a substituent group on a benzene ring, or a phenylaminomethyl group which may have a substituent group on a benzene ring,
m represents an integer of 1 or 2, and
$Y^1$ and $Y^2$ each independently represent methylene, O or S, with the proviso that both of them do not simultaneously represent S).

The present invention further provides a pharmaceutical agent containing the compound represented by General Formula (1) shown above, a pharmaceutically acceptable salt thereof, or a solvate thereof.

The present invention further provides a pharmaceutical composition containing the compound represented by General Formula (1) shown above, a pharmaceutically acceptable salt thereof, or a solvate thereof, and a pharmaceutically acceptable carrier.

The present invention further provides the compound represented by General Formula (1) shown above, a pharmaceutically acceptable salt thereof, or a solvate thereof for prevention or treatment of disorders related with soluble guanylate cyclase such as heart failure, hypertension, pulmonary hypertension, or ischemic heart disease.

The present invention further provides a use of the compound represented by General Formula (1) shown above, a pharmaceutically acceptable salt thereof, or a solvate thereof for producing a pharmaceutical agent for prevention or treatment of disorders related with soluble guanylate cyclase such as heart failure, hypertension, pulmonary hypertension, or ischemic heart disease.

The present invention still further provides a method for prevention or treatment of disorders related with soluble guanylate cyclase such as heart failure, hypertension, pulmonary hypertension, or ischemic heart disease, characterized in that an effective amount of the compound represented by General Formula (1) shown above, a pharmaceutically acceptable salt thereof, or a solvate thereof is administered.

Advantageous Effects of the Invention

The compound of the present invention has a high heme-independent property, an excellent function of activating soluble guanylate cyclase, and is useful as a pharmaceutical agent for prevention or treatment of various disorders related with soluble guanylate cyclase. Examples of the disorders that can be prevented or treated by the function of activating soluble guanylate cyclase include heart failure, hypertension, pulmonary hypertension, and ischemic heart disease.

DETAILED DESCRIPTION OF THE INVENTION

As described herein, the "linear alkylene group" indicates a linear alkylene group having a predetermined number of carbon atoms. Specific examples thereof include a methylene group, —$(CH_2)_2$—, —$(CH_2)_3$—, —$(CH_2)_4$—, —$(CH_2)_5$—, and —$(CH_2)_6$—.

As described herein, the "branched alkylene group" indicates a branched alkylene group having a predetermined number of carbon atoms. Specific examples thereof include —$CH(CH_3)$—, —$CH(C_2H_5)$—, —$CH(C_3H_7)$—, —$CH(C_4H_9)$—, —$CH(C_5H_{11})$—, —$CH_2CH(CH_3)$—, and —$CH_2CH_2CH(CH_3)$—.

As described herein, "one methylene group is optionally substituted with O or S" for the "linear or branched alkylene group" means that any methylene group in the linear or branched alkylene group is substituted with O or S. Examples of a case in which the "linear alkylene group" is a methylene group with one carbon atom also include —O— and —S—.

Specific examples thereof include —CH$_2$O—, —CH$_2$S—, —(CH$_2$)$_2$S—, —(CH$_2$)$_3$O—, —(CH$_2$)$_3$S—, —(CH$_3$)O—, —CH(CH$_3$)O—, —CH(CH$_3$)S—, —CH$_2$CH(CH$_3$)O—, and —CH$_2$CH(CH$_3$)S—.

As described herein, the "halogen atom" includes a fluorine atom, a chlorine atom, a bromine atom, and an iodine atom.

As described herein, the "C$_1$-C$_6$ alkyl group" indicates a linear alkyl group having 1 to 6 carbon atoms or a branched alkyl group having 3 to 6 carbon atoms. Examples of the C$_1$-C$_6$ alkyl group include a methyl group, an ethyl group, an n-propyl group, an n-butyl group, an isopropyl group, an isobutyl group, a sec-butyl group, a tert-butyl group, an n-pentyl group, and an n-hexyl group.

As described herein, the "C$_1$-C$_6$ alkoxy group" indicates a group of the "C$_1$-C$_6$ alkyl group" in which one hydrogen atom is substituted with an oxygen atom. Specifically, it is a linear alkoxy group having 1 to 6 carbon atoms or a branched alkoxy group having 3 to 6 carbon atoms, and examples of the C$_1$-C$_6$ alkoxy group include a methoxy group, an ethoxy group, an n-propoxy group, an isopropoxy group, an n-butoxy group, an isobutoxy group, a tert-butoxy group, an n-pentyloxy group, and an n-hexyloxy group.

As described herein, the "C$_3$-C$_6$ cycloalkyl group" indicates a cyclic alkyl group having 3 to 6 carbon atoms. Specific examples thereof include a cyclopropyl group, a cyclobutyl group, a cyclopentyl group, and a cyclohexyl group.

As described herein, the "C$_3$-C$_6$ cycloalkoxy group" indicates a group of the "C$_3$-C$_6$ cycloalkyl group" in which one hydrogen atom is substituted with an oxygen atom. Specific examples thereof include a cyclopropoxy group, a cyclobutoxy group, a cyclopentyloxy group, and a cyclohexyloxy group.

As described herein, the "halo C$_1$-C$_4$ alkyl group" indicates a group of C$_1$-C$_4$ alkyl group, which is a linear alkyl group having 1 to 4 carbon atoms or a branched alkyl group having 3 or 4 carbon atoms, in which one or more hydrogen atoms are substituted with a halogen atom. Examples of the halo C$_1$-C$_4$ alkyl group include a chloromethyl group, a dichloromethyl group, a trichloromethyl group, a fluoromethyl group, a difluoromethyl group, a trifluoromethyl group, a bromomethyl group, a dibromomethyl group, a tribromomethyl group, a 2-chloroethyl group, a 2,2-dichloroethyl group, a 2,2,2-trichloroethyl group, a 2-fluoroethyl group, a 2,2-difluoroethyl group, a 2,2,2-trifluoroethyl group, a 1,1,2,2-tetrafluoroethyl group, a pentafluoroethyl group, a 2-bromoethyl group, a 2,2,2-tribromoethyl group, a 3,3,3-trichloropropyl group, a 3,3,3-trifluoropropyl group, a 3,3,3-tribromopropyl group, a 4,4,4-trichlorobutyl group, and a 4,4,4-trifluorobutyl group.

As described herein, the "halo C$_1$-C$_4$ alkoxy group" indicates a group of the "halo C$_1$-C$_4$ alkyl group" in which one hydrogen atom is substituted with an oxygen atom. Examples of the halo C$_1$-C$_4$ alkoxy group include a chloromethoxy group, a dichloromethoxy group, a trichloromethoxy group, a fluoromethoxy group, a difluoromethoxy group, a trifluoromethoxy group, a 2-chloroethoxy group, a 2,2-dichloroethoxy group, a 2,2,2-trichloroethoxy group, a 2-fluoroethoxy group, a 2,2-difluoroethoxy group, a 2,2,2-trifluoroethoxy group, a 1,1,2,2-tetrafluoroethoxy group, a pentafluoroethoxy group, a 3,3,3-trichloropropoxy group, a 3,3,3-trifluoropropoxy group, a 4,4,4-trichlorobutoxy group, and a 4,4,4-trifluorobutoxy group.

As described herein, the "aryl group" indicates a monocyclic or polycyclic aromatic hydrocarbon group having 6 to 10 carbon atoms. Examples of the aryl group include a phenyl group and a naphthyl group. More specific examples include a phenyl group, a 1-naphthyl group, and a 2-naphthyl group.

As described herein, the "aryloxy group" indicates a group of the "aryl group" in which one hydrogen atom is substituted with an oxygen atom. Examples of the aryloxy group include a phenoxy group and a naphthoxy group. More specific examples include a phenoxy group, a 1-naphthoxy group, and a 2-naphthoxy group.

As described herein, "which may have a substituent group" indicates non-substitution or having, on a substitutable position, one or more substituent groups that are the same with or different from each other, preferably 1 to 2, and more preferably one substituent group. Examples of the substituent group include a halogen atom, a C$_1$-C$_6$ alkyl group, a C$_1$-C$_6$ alkoxy group, a C$_3$-C$_5$ cycloalkyl group, a C$_3$-C$_6$ cycloalkoxy group, a halo C$_1$-C$_4$ alkyl group, and an aryl group. Definition of each substituent group is as defined above, and it may further have a substituent group.

As for the halogen atom represented by R$^1$, R$^2$, R$^3$, R$^4$ and R$^5$, it is preferably a fluorine atom or a chlorine atom, and more preferably a chlorine atom.

When the a C$_1$-C$_6$ alkyl group which may have a substituent group, which is represented by R$^1$, R$^2$, R$^3$, R$^4$ and R$^5$, has a substituent group, examples of the substituent group include a C$_1$-C$_6$ alkoxy group, a C$_3$-C$_6$ cycloalkyl group, and a C$_3$-C$_6$ cycloalkoxy group. Among them, a C$_3$-C$_6$ cycloalkyl group is preferable, and a cyclohexyl group is particularly preferable. As for the C$_1$-C$_6$ alkyl group which may have a substituent group, it is preferably a methyl group, an ethyl group, an isopropyl group, a tert-butyl group, a 2-methoxyethyl group, a 2-cyclopropylethyl group, or a 2-cyclohexylethyl group, and more preferably an isopropyl group, a tert-butyl group, or a 2-cyclohexylethyl group.

As for the C$_1$-C$_6$ alkoxy group represented by R$^1$, R$^2$, R$^3$, R$^4$ and R$^5$, it is preferably a methoxy group, an ethoxy group, an n-propoxy group, an isopropoxy group, or a tert-butoxy group, and more preferably a methoxy group or a tert-butoxy group.

As for the C$_3$-C$_6$ cycloalkyl group represented by R$^1$, R$^2$, R$^3$, R$^4$ and R$^5$, it is preferably a cyclopropyl group or a cyclohexyl group, and more preferably a cyclopropyl group.

As for the C$_3$-C$_6$ cycloalkoxy group represented by R$^1$, R$^2$, R$^3$, R$^4$ and R$^5$, examples include a cyclopropyloxy group, a cyclopentyloxy group, and a cyclohexyloxy group. It is preferably a cyclohexyloxy group.

As for the halo C$_1$-C$_4$ alkyl group represented by R$^1$, R$^2$, R$^3$, R$^4$ and R$^5$, it is preferably a C$_1$-C$_4$ alkyl group substituted with one or more fluorine atoms. It is more preferably a C$_1$-C$_4$ alkyl group substituted with 1 to 5 fluorine atoms. Specific examples thereof include a trifluoromethyl group, a 2,2,2-trifluoroethyl group, a 1,1,2,2-tetrafluoroethyl group, and a pentafluoroethyl group. More preferably, it is a trifluoromethyl group.

As for the halo C$_1$-C$_4$ alkoxy group represented by R$^1$, R$^2$, R$^3$, R$^4$ and R$^5$, it is preferably a C$_1$-C$_4$ alkoxy group which is substituted with one or more fluorine atoms. It is more preferably a C$_1$-C$_4$ alkoxy group substituted with 1 to 5 fluorine atoms. Specific examples thereof include a trifluoromethoxy group, a 2,2,2-trifluoroethoxy group, a 1,1,2,2-tetrafluoroethoxy group, and a pentafluoroethoxy group. More preferably, it is a trifluoromethoxy group.

When the vinyl group which may have a substituent group or the ethynyl group which may have a substituent group, as represented by R$^2$, R$^2$, R$^3$, R$^4$ and R$^5$, has a substituent group, the substituent group is preferably a C$_1$-C$_6$ alkyl group, a C$_3$-C$_6$ cycloalkyl group, or an aryl group, and the aryl group is preferably a phenyl group. The aryl group may further have a substituent group such as a halogen atom, a $C_1$-$C_6$ alkyl group, or a halo $C_1$-$C_4$ alkyl group. It is preferable that the vinyl group be not substituted or have 1 to 2 substituent groups. It is particularly preferable for the vinyl group to have one substituent group. It is preferable for the ethynyl group to have no substituent group or one substituent group. Examples of the vinyl group which may have a substituent group or the ethynyl group which may have a substituent group include a vinyl group, a cyclohexylvinyl group, a styryl group, an ethynyl group, a 3-methyl-1-butyn-1-yl group, a cyclopropylethynyl group, a cyclohexylethynyl group, and a phenylethynyl group. It is preferably a cyclohexylvinyl group, a styryl group, or a cyclohexylethynyl group.

With regard to the aryl group which may have a substituent group on an aromatic ring or the aryloxy group which may have a substituent group on an aromatic ring, which is represented by $R^1$, $R^2$, $R^3$, $R^4$ and $R^5$, the aromatic ring is preferably a benzene ring. When the aromatic ring has a substituent group, the substituent group is preferably a halogen atom, a $C_1$-$C_6$ alkyl group, a $C_1$-$C_6$ alkoxy group, or a halo $C_1$-$C_4$ alkyl group. It is preferable that the aryl group or aryloxy group which may have a substituent group have no substituent group or 1 to 2 substituent groups. It is more preferable that it have one substituent group at para position. Specific examples of the aryl group or aryloxy group which may have a substituent group include a phenyl group, a 4-trifluoromethylphenyl group, a 4-chlorophenyl group, a 4-tert-butylphenyl group, a 4-methoxyphenyl group, a phenoxy group, a 4-trifluoromethylphenoxy group, a 4-chlorophenoxy group, a 4-tert-butylphenoxy group, and a 4-methoxyphenoxy group. It is more preferably a phenyl group, a 4-trifluoromethylphenyl group, a 4-tert-butylphenyl group, a phenoxy group, a 4-trifluoromethylphenoxy group, or a 4-tert-butylphenoxy group.

With regard to the benzyl group which may have a substituent group on a benzene ring, the phenethyl group which may have a substituent group on a benzene ring, the benzyloxy group which may have a substituent group on a benzene ring, the benzylsulfanyl group which may have a substituent group on a benzene ring, the benzylamino group which may have a substituent group on a benzene ring, the phenyloxymethyl group which may have a substituent group on a benzene ring, the phenylsulfanylmethyl group which may have a substituent group on a benzene ring, or the phenylaminomethyl group which may have a substituent group on a benzene ring, which is represented by $R^1$, $R^2$, $R^3$, $R^4$ and $R^5$ (hereinbelow, the benzyl group to the phenylaminomethyl group are collectively referred to as a type of the benzyl group), it is preferable that it be not substituted or have 1 to 2 substituent groups on a benzene ring. It is particularly preferable that it have one substituent group at para position. As for the substituent group, it is preferably a halogen atom, a $C_1$-$C_6$ alkyl group, or a halo $C_1$-$C_4$ alkyl group, more preferably a halo $C_1$-$C_4$ alkyl group, and most preferably a trifluoromethyl group. As for the type of benzyl group, it is preferably a phenethyl group, a benzyloxy group, or a benzylsulfanyl group, and particularly preferably a phenethyl group. Specific examples of the type of benzyl group which may have a substituent group on a benzene ring include a benzyl group, a phenethyl group, a benzyloxy group, a benzylsulfanyl group, a benzylamino group, a phenyloxymethyl group, a phenylsulfanylmethyl group, a phenylaminomethyl group, a (4-fluoro)phenethyl group, a (4-fluoro)benzyloxy group, a (4-fluoro)benzylsulfanyl group, a (4-trifluoromethyl)phenethyl group, a (4-trifluoromethyl)benzyloxy group, a (4-trifluoromethyl)benzylsulfanyl group, a (4-tert-butyl)phenethyl group, a (4-tert-butyl)benzyloxy group, and a (4-tert-butyl)benzylsulfanyl group. It is preferably a phenethyl group, a benzyloxy group, a benzylsulfanyl group, a phenyloxymethyl group, a phenylsulfanylmethyl group, or a phenylaminomethyl group, and more preferably a phenethyl group, a benzyloxy group, or a benzylsulfanyl group.

Specific examples of the $C_1$-$C_3$ linear alkylene group represented by A include a methylene group, —O—, —S—, —$CH_2CH_2$—, —$CH_2O$—, —$CH_2S$—, —$OCH_2$—, —$SCH_2$—, —$(CH_2)_3$—, —$OCH_2CH_2$—, —$SCH_2CH_2$—, —$CH_2OCH_2$—, —$CH_2SCH_2$—, —$CH_2CH_2O$—, and —$CH_2CH_2S$—. Among them, a methylene group, —O—, —$CH_2CH_2$—, —$CH_2O$—, —$OCH_2$—, —$CH_2CH_2CH_2$—, —$CH_2OCH_2$—, —$CH_2SCH_2$—, and —$CH_2CH_2O$— are preferable, and —$CH_2CH_2$— and —$CH_2O$— are particularly preferable.

n is most preferably 4.

$X^2$ is most preferably CH.

$W^1$ and $W^2$ are preferably a carboxyl group.

Specific examples of the $C_1$-$C_8$ linear or branched alkylene group represented by V include a methylene group, —O—, —S—, —$CH_2CH_2$—, —$CH(CH_3)O$—, —$CH_2CH(CH_3)$—, —$CH_2CH(CH_3)O$—, —$CH_2CH(CH_3)S$—, —$CH_2O$—, —$CH_2S$—, —$OCH_2$—, and —$SCH_2$—. Among them, —$CH_2CH_2$—, —$CH(CH_3)O$—, and —$CH_2O$— are preferable, and —$CH_2O$— is particularly preferable.

When the group represented by R corresponds to the following formula,

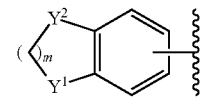

wherein m represents an integer of 1 or 2, and
$Y^1$ and $Y^2$ each independently represent a methylene group, O, or S, with the proviso that it is not simultaneously S) specific examples thereof include a group represented by the following formula.

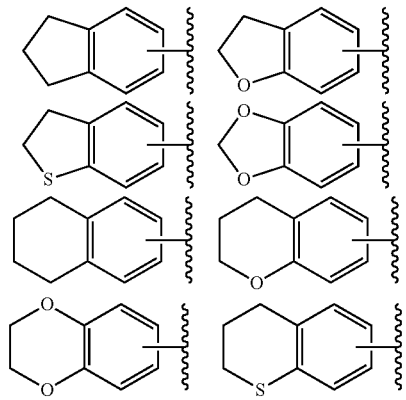

Among them, a group selected from the following formula is preferable.

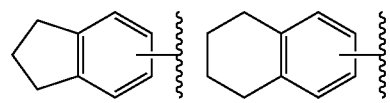

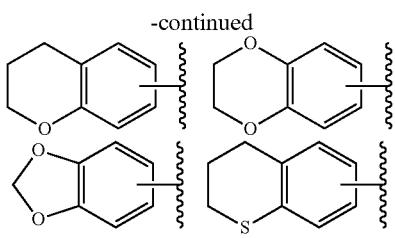

As for the group represented by R, a group selected from the following formula

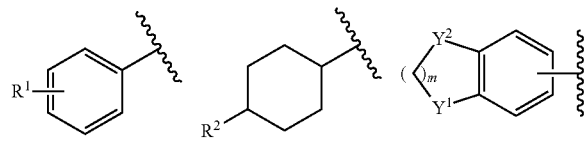

is preferable, and

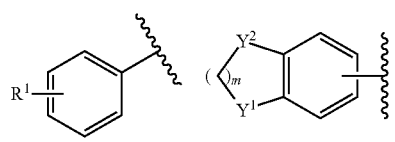

the above are particularly preferable.

As for $R^1$, a $C_1$-$C_6$ alkyl group which may have a substituent group, a $C_3$-$C_6$ cycloalkyl group, a $C_1$-$C_6$ alkoxy group, a halo $C_1$-$C_4$ alkyl group, a vinyl group which may have a substituent group, an ethynyl group which may have a substituent group, an aryl group which may have a substituent group on an aromatic ring, an aryloxy group which may have a substituent group on an aromatic ring, a benzyl group which may have a substituent group on a benzene ring, a phenethyl group which may have a substituent group on a benzene ring, a benzyloxy group which may have a substituent group on a benzene ring, a benzylsulfanyl group which may have a substituent group on a benzene ring, a benzylamino group which may have a substituent group on a benzene ring, a phenyloxymethyl group which may have a substituent group on a benzene ring, a phenylsulfanylmethyl group which may have a substituent group on a benzene ring, or a phenylaminomethyl group which may have a substituent group on a benzene ring is preferable. More preferably, it is a $C_1$-$C_6$ alkyl group, a $C_3$-$C_6$ cycloalkyl group, a vinyl group which may have a substituent group, an ethynyl group which may have a substituent group, a phenethyl group which may have a substituent group on a benzene ring, a benzyloxy group which may have a substituent group on a benzene ring, or a benzylsulfanyl group which may have a substituent group on a benzene ring. Position for $R^2$ substitution is preferably meta position or para position. Herein, the substituent group on the $C_1$-$C_6$ alkyl group is preferably a $C_1$-$C_6$ alkoxy group, a $C_3$-$C_6$ cycloalkyl group, or a $C_3$-$C_6$ cycloalkoxy group. The substituent group on the vinyl group or the ethynyl group is preferably a $C_1$-$C_6$ alkyl group, a $C_3$-$C_6$ cycloalkyl group, a phenyl group, a halogenophenyl group, a $C_1$-$C_6$ alkylphenyl group, or a halo $C_1$-$C_4$ alkylphenyl group. As for the aryl group, a phenyl group is preferable. As for the aryloxy group, a phenoxy group is preferable. The substituent group on the aryl or aryloxy group is preferably a halogen atom, a $C_1$-$C_6$ alkyl group, a $C_1$-$C_6$ alkoxy group, or a halo $C_1$-$C_4$ alkyl group. The substituent group on the benzene ring is preferably a halogen atom, a $C_1$-$C_6$ alkyl group, or a halo $C_1$-$C_4$ alkyl group.

As for $R^2$, a vinyl group which may have a substituent group, an ethynyl group which may have a substituent group, a benzyl group which may have a substituent group on a benzene ring, a phenethyl group which may have a substituent group on a benzene ring, a benzyloxy group which may have a substituent group on a benzene ring, a benzylsulfanyl group which may have a substituent group on a benzene ring, a benzylamino group which may have a substituent group on a benzene ring, a phenyloxymethyl group which may have a substituent group on a benzene ring, a phenylsulfanylmethyl group which may have a substituent group on a benzene ring, or a phenylaminomethyl group which may have a substituent group on a benzene ring is preferable. More preferably, it is a vinyl group which may have a substituent group, a phenethyl group which may have a substituent group on a benzene ring, a benzyloxy group which may have a substituent group on a benzene ring, or a benzylsulfanyl group which may have a substituent group on a benzene ring. Most preferably, it is a phenethyl group which may have a substituent group on a benzene ring. Herein, the substituent group on the vinyl group or the ethynyl group is preferably a $C_1$-$C_6$ alkyl group, a $C_3$-$C_6$ cycloalkyl group, a phenyl group, a halogenophenyl group, a $C_1$-$C_6$ alkylphenyl group, or a halo $C_1$-$C_4$ alkylphenyl group. The substituent group on a benzene ring is preferably a halogen atom, a $C_1$-$C_6$ alkyl group, or a halo $C_1$-$C_4$ alkyl group.

As for $R^3$, a hydrogen atom, a $C_1$-$C_6$ alkyl group which may have a substituent group, a $C_1$-$C_6$ alkoxy group, or a halo $C_1$-$C_4$ alkyl group, is preferable. Most preferably, it is a hydrogen atom. Position for $R^3$ substitution is most preferably para position. Herein, the substituent group on the $C_1$-$C_6$ alkyl group is preferably a $C_1$-$C_6$ alkoxy group, a $C_3$-$C_6$ cycloalkyl group, or a $C_3$-$C_6$ cycloalkoxy group.

As for $R^4$, a hydrogen atom, a $C_1$-$C_6$ alkyl group which may have a substituent group, a $C_1$-$C_6$ alkoxy group, or a halo $C_1$-$C_4$ alkyl group, an aryl group which may have a substituent group on an aromatic ring, or an aryloxy group which may have a substituent group on an aromatic ring is preferable. Most preferably, it is a hydrogen atom. Position for $R^4$ substitution is preferably 6 position. Herein, the substituent group on the $C_1$-$C_6$ alkyl group is preferably a $C_1$-$C_6$ alkoxy group, a $C_3$-$C_6$ cycloalkyl group, or a $C_3$-$C_6$ cycloalkoxy group. As for the aryl group, a phenyl group is preferable. As for the aryloxy group, a phenoxy group is preferable. The substituent group on the aryl or aryloxy group is preferably a halogen atom, a $C_1$-$C_6$ alkyl group, a $C_1$-$C_6$ alkoxy group, or a halo $C_1$-$C_4$ alkyl group.

As for $R^5$, a hydrogen atom, a benzyl group which may have a substituent group on a benzene ring, a phenethyl group which may have a substituent group on a benzene ring, a benzyloxy group which may have a substituent group on a benzene ring, a benzylsulfanyl group which may have a substituent group on a benzene ring, a benzylamino group which may have a substituent group on a benzene ring, a phenyloxymethyl group which may have a substituent group on a benzene ring, a phenylsulfanylmethyl group which may have a substituent group on a benzene ring, or a phenylaminomethyl group which may have a substituent group on a benzene ring is preferable. It is more preferably a hydrogen atom or a phenethyl group. Position for $R^5$ substitution is preferably 6 position. Herein, the substituent group on a benzene ring is preferably a halogen atom, a $C_1$-$C_6$ alkyl group, or a halo $C_1$-$C_4$ alkyl group.

In General Formula (1), it is preferable that A be a methylene group, —O—, —CH$_2$CH$_2$—, —CH$_2$O—, —OCH$_2$—, —CH$_2$CH$_2$CH$_2$—, —CH$_2$OCH$_2$—, —CH$_2$SCH$_2$— or —CH$_2$CH$_2$O—;
n be an integer of from 3 to 5;
W$^1$ and W$^2$ be a carboxy group;
V be —CH$_2$CH$_2$—, —CH(CH$_3$)O— or —CH$_2$O—; and
R be as follows:

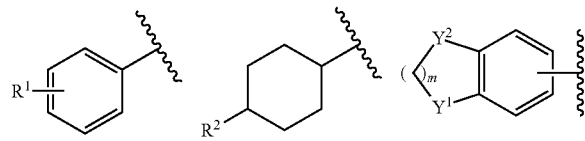

In the formula, R$^1$, R$^2$, Y$^1$, Y$^2$ and m are as defined above.
In General Formula (1), it is more preferable that A be a methylene group, —O—, —CH$_2$CH$_2$—, —CH$_2$O—, —OCH$_2$—, —CH$_2$CH$_2$CH$_2$—, —CH$_2$OCH$_2$—, —CH$_2$SCH$_2$— or —CH$_2$CH$_2$O;
n be an integer of 4;
W$^1$ and W$^2$ be a carboxyl group.
V be —CH$_2$CH$_2$—, —CH(CH$_3$)O— or —CH$_2$O—; and
R be as follows:

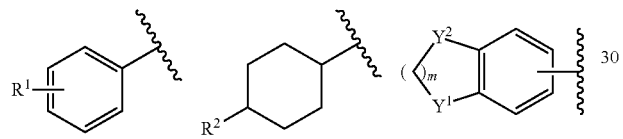

In the formula, R$^1$, R$^2$, Y$^1$, Y$^2$ and m are as defined above.
In the preferred embodiment, R$^1$ is preferably a C$_1$-C$_6$ alkyl group which may have a substituent group, a C$_3$-C$_6$ cycloalkyl group, a C$_1$-C$_6$ alkoxy group, a halo C$_1$-C$_4$ alkyl group, a vinyl group which may have a substituent group, an ethynyl group which may have a substituent group, an aryl group which may have a substituent group on an aromatic ring, an aryloxy group which may have a substituent group on an aromatic ring, a benzyl group which may have a substituent group on a benzene ring, a phenethyl group which may have a substituent group on a benzene ring, a benzyloxy group which may have a substituent group on a benzene ring, a benzylsulfanyl group which may have a substituent group on a benzene ring, a benzylamino group which may have a substituent group on a benzene ring, a phenyloxymethyl group which may have a substituent group on a benzene ring, a phenylsulfanylmethyl group on a benzene ring, or a phenylaminomethyl group which may have a substituent group on a benzene ring. More preferably, it is a C$_1$-C$_6$ alkyl group, a C$_3$-C$_6$ cycloalkyl group, a vinyl group which may have a substituent group, an ethynyl group which may have a substituent group, a phenethyl group which may have a substituent group on a benzene ring, a benzyloxy group which may have a substituent group on a benzene ring, or a benzylsulfanyl group which may have a substituent group on a benzene ring. Herein, the substituent group on an alkyl group, a vinyl group, an ethynyl group, an aryl group, an aryloxy group, and a benzene ring is preferably the same as those described above.

As for R$^2$, a vinyl group which may have a substituent group, an ethynyl group which may have a substituent group, a benzyl group which may have a substituent group on a benzene ring, a phenethyl group which may have a substituent group on a benzene ring, a benzyloxy group which may have a substituent group on a benzene ring, a benzylsulfanyl group which may have a substituent group on a benzene ring, a benzylamino group which may have a substituent group on a benzene ring, a phenyloxymethyl group which may have a substituent group on a benzene ring, a phenylsulfanylmethyl group which may have a substituent group on a benzene ring, or a phenylaminomethyl group which may have a substituent group on a benzene ring is preferable. More preferably, it is a vinyl group which may have a substituent group, a phenethyl group which may have a substituent group on a benzene ring, a benzyloxy group which may have a substituent group on a benzene ring, or a benzylsulfanyl group which may have a substituent group on a benzene ring. Most preferably, it is a phenethyl group which may have a substituent group on a benzene ring. Herein, the substituent group on a vinyl group, an ethynyl group, and a benzene ring is preferably the same as those described above.

In the preferred embodiment,

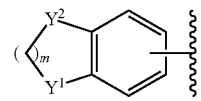

when R is as shown above,

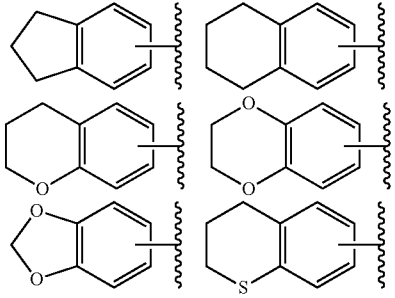

it is preferably a group selected from above.
Specific examples of the particularly preferred compounds among the compounds of General Formula (1) of the present invention include the followings.
1-{N-(4-Carboxybutyl)-N-[2-[2-[4-(2-phenylethyl)benzyloxy]phenyl]ethyl]amino}indane-5-carboxylic acid (Example 1)
5-{N-(4-Carboxybutyl)-N-[2-[2-[4-(2-phenylethyl)benzyloxy]phenyl]ethyl]amino}-5,6,7,8-tetrahydronaphthalene-2-carboxylic acid (Example 2)
5-{N-(4-Carboxybutyl)-N-[2-[2-[4-(2-phenylethyl)benzyloxy]phenyl]ethyl]amino}-6,7,8,9-tetrahydro-5H-benzocycloheptene-2-carboxylic acid (Example 3)
4-{N-(4-Carboxybutyl)-N-[2-[2-[4-(2-phenylethyl)benzyloxy]phenyl]ethyl]amino}chromane-7-carboxylic acid (Example 4)
4-{N-(4-Carboxybutyl)-N-[2-[2-[4-(2-phenylethyl)benzyloxy]phenyl]ethyl]amino}thiochromane-7-carboxylic acid (Example 5)
5-{N-(4-Carboxybutyl)-N-[2-[2-[4-(2-phenylethyl)benzyloxy]phenyl]ethyl]amino}-5,6,7,8-tetrahydroquinoline-2-carboxylic acid (Example 6)
3-{N-(4-Carboxybutyl)-N-[2-[2-[4-(2-phenylethyl)benzyloxy]phenyl]ethyl]amino}-2,3-dihydrobenzofuran-6-carboxylic acid (Example 7)

4-{N-(4-Carboxybutyl)-N-[2-[2-[4-(2-phenylethyl)benzyloxy]phenyl]ethyl]amino}-isochromane-7-carboxylic acid (Example 8)

5-{N-(4-Carboxybutyl)-N-[2-[2-(2-chlorobenzyloxyl)phenyl]ethyl]amino}-5,6,7,8-tetrahydronaphthalene-2-carboxylic acid (Example 13)

5-{N-[2-[2-(4-Benzyloxybenzyloxyl)phenyl]ethyl]-N-(4-carboxybutyl)amino}-5,6,7,8-tetrahydronaphthalene-2-carboxylic acid (Example 14)

5-{N-[2-[2-(4-Benzylsulfanylbenzyloxy)phenyl]ethyl]-N-(4-carboxybutyl)amino}-5,6,7,8-tetrahydronaphthalene-2-carboxylic acid (Example 15)

5-{N-(4-Carboxybutyl)-N-[2-[2-(4-phenoxymethylbenzyloxy)phenyl]ethyl]amino}-5,6,7,8-tetrahydronaphthalene-2-carboxylic acid (Example 16)

5-{N-(4-Carboxybutyl)-N-[2-[2-(4-phenylsulfanylmethylbenzyloxy)phenyl]ethyl]amino}-5,6,7,8-tetrahydronaphthalene-2-carboxylic acid (Example 17)

5-{N-(4-Carboxybutyl)-N-[2-[2-(4-ethynylbenzyloxy)phenyl]ethyl]amino}-5,6,7,8-tetrahydronaphthalene-2-carboxylic acid (Example 19)

5-{N-(4-Carboxybutyl)-N-[2-[2-(4-cyclohexylethynylbenzyloxy)phenyl]ethyl]amino}-5,6,7,8-tetrahydronaphthalene-2-carboxylic acid (Example 22)

5-{N-(4-Carboxybutyl)-N-[2-[2-[4-((E)-2-cyclohexylethenyl)benzyloxy]phenyl]ethyl]amino}-5,6,7,8-tetrahydronaphthalene-2-carboxylic acid (Example 23)

5-{N-(4-Carboxybutyl)-N-[2-[2-[4-(2-cyclohexylethyl)benzyloxy]phenyl]ethyl]amino}-5,6,7,8-tetrahydronaphthalene-2-carboxylic acid (Example 24)

5-{N-(4-Carboxybutyl)-N-[2-[2-[trans-4-(2-phenylethyl)cyclohexylmethoxy]phenyl]ethyl]amino}-5,6,7,8-tetrahydronaphthalene-2-carboxylic acid (Example 26)

5-{N-(4-Carboxybutyl)-N-[2-[2-[cis-4-(2-phenylethyl)cyclohexylmethoxy]phenyl]ethyl]amino}-5,6,7,8-tetrahydronaphthalene-2-carboxylic acid (Example 27)

5-{N-(4-Carboxybutyl)-N-[2-[2-(5,6,7,8-tetrahydronaphthalen-1-ylmethoxy)phenyl]ethyl]amino}-5,6,7,8-tetrahydronaphthalene-2-carboxylic acid (Example 29)

5-{N-[2-[2-(3-tert-Butylbenzyloxy)phenyl]ethyl]-N-(4-carboxybutyl)amino}-5,6,7,8-tetrahydronaphthalene-2-carboxylic acid (Example 41)

5-{N-(4-Carboxybutyl)-N-[2-[2-(4-cyclopropylbenzyloxy)phenyl]ethyl]amino}-5,6,7,8-tetrahydronaphthalene-2-carboxylic acid (Example 42)

5-{N-(4-Carboxybutyl)-N-[2-[2-(4-isopropylbenzyloxy)phenyl]ethyl]amino}-5,6,7,8-tetrahydronaphthalene-2-carboxylic acid (Example 43)

5-{N-[2-[2-[(1R)-1-(4-tert-Butylphenyl)ethoxy]phenyl]ethyl]-N-(4-carboxybutyl)amino}-5,6,7,8-tetrahydronaphthalene-2-carboxylic acid (Example 45)

5-{N-(4-Carboxybutyl)-N-[2-[2-(indane-5-ylmethoxy)phenyl]ethyl]amino}-5,6,7,8-tetrahydronaphthalene-2-carboxylic acid (Example 46)

As described herein, the compound of General Formula (1) may yield an isomer such as geometric isomer, optical isomer, stereo isomer, or tautomeric isomer. The compounds of General Formula (1) of the present invention include any one of those isomers or a mixture of them.

Furthermore, the compound of General Formula (1) of the present invention includes compounds obtained by labeling with, for example, an isotope (for example, $^2H$, $^3H$, $^{14}C$, $^{35}C$, $^{35}S$ or $^{125}I$).

Furthermore, the present invention includes pharmaceutically acceptable salts of the compound of General Formula (1). Specific examples thereof include acid addition salts with inorganic acids, such as hydrochloride, hydrobromide, hydroiodide, sulfate, nitrate and phosphate, acid addition salts with organic acids, such as formate, acetate, trichloroacetate, trifluoroacetate, propionate, oxalate, malonate, succinate, fumarate, maleate, lactate, malate, tartrate, citrate, methanesulfonate, ethanesulfonate, benzenesulfonate, p-toluenesulfonate (4-methylbenzenesulfonate), asparaginate and glutamate; salts with inorganic bases, such as sodium salts, potassium salts, magnesium salts, calcium salts, ammonium salts, and aluminum salts; and salts with organic bases, such as methylamine, ethylamine, ethanolamine, lysine, and ornithine.

Furthermore, according to the present invention, hydrates, various solvates and crystal polymorphisms of the compound (1) of the present invention and pharmaceutically acceptable salts thereof may exist. However, similarly, there are no limitations, and the present invention may include any single crystal form and a mixture of crystal forms and may include any of them.

Furthermore, the compound (1) of the present invention may be prepared as a prodrug by having a pharmaceutically acceptable group. Examples of the pharmaceutically acceptable group that forms a prodrug include the groups described in Prog. Med., 5, 2157-2161 (1985), or "Development of Pharmaceutical Products" (Hirokawa Shoten Ltd., 1990) Vol. 7, Molecular Design, 163-198.

The compound of General Formula (1) of the present invention, a pharmaceutically acceptable salt, or a solvate thereof (hereinbelow, they are collectively referred to as the compound of the present invention) can be produced by utilizing the features based on the type of the basic skeleton or a substituent group thereof, and applying various synthesis methods that are known per se in connection with the introduction of substituent groups or conversion of functional groups.

Examples of the method for producing the compound of the present invention are given below, however, the production method for the compound of the present invention is not intended to be limited to these methods.

The compound of General Formula (1) can be produced according to the following scheme, for example.

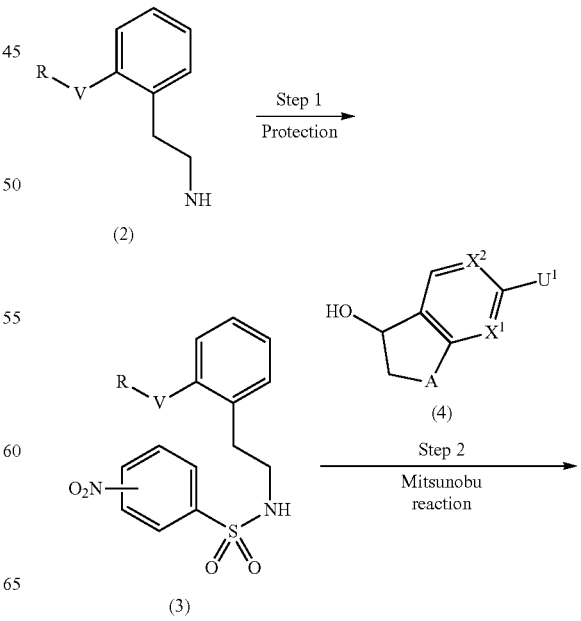

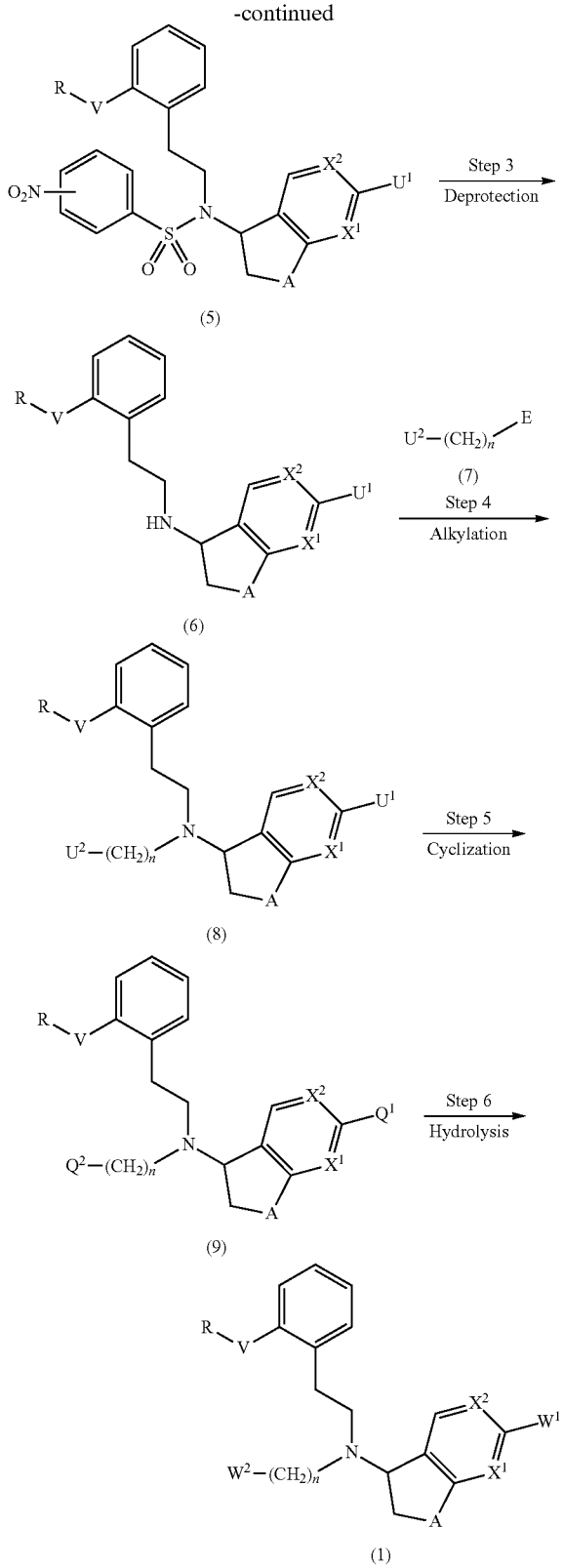

wherein A, n, $X^1$, $X^2$, $W^1$, $W^2$, R and V are as defined above. $U^1$ and $U^2$ each correspond to $W^1$ and $W^2$, and when $W^1$ and/or $W^2$ is a tetrazolyl group, $U^1$ and/or $U^2$ is a cyano group and when $W^1$ and/or $W^2$ is a carboxyl group, $U^1$ and/or $U^2$ represents $CO_2R^6$. $Q^1$ and $Q^2$ each correspond to $W^1$ and $W^2$, and when $W^1$ and/or $W^2$ is a tetrazolyl group, $Q^1$ and/or $Q^2$ is also a tetrazolyl group and when $W^1$ and/or $W^2$ is a carboxyl group, $Q^1$ and/or $Q^2$ represents $CO_2R^6$. Herein, $R^6$ represents a $C_1$-$C_6$ alkyl group. E represents a leaving group or a hydroxyl group).

As described herein, the "leaving group" represents a group which is substituted in the presence of a base or a group having an activated oxygen atom. Specific examples thereof include a halogen atom; a trihalogenomethyloxy group such as a trichloromethyloxy; a lower alkane sulfonyloxy group such as a methanesulfonyloxy group or an ethanesulfonyloxy group; a lower halogenoalkane sulfonyloxy group such as a trifluoromethanesulfonyloxy group or a pentafluoroethane-sulfonyloxy group; and an arylsufonyloxyl group such as a benzenesulfonyloxy group, a p-toluenesulfonyloxy group, or a p-nitrobenzenesulfonyloxy group.

Step 1: Nosyl protection

The compound (3) can be produced by reacting the compound (2) with an agent for introducing a nitrobenzenesulfonyl group in the presence or absence of a base, in the absence of a solvent or in an inert solvent. Examples of the agent for introducing a nitrobenzenesulfonyl group which can be used include 2-nitrobenzenesulfonyl chloride and 4-nitrobenzenesulfonyl chloride. The use amount of the agent for introducing a nitrobenzenesulfonyl group is, with respect to the compound (2), generally 1 to 5 equivalents, and preferably 1 to 2 equivalents. Examples of the base which can be used include alkali metal carbonate salt, alkali metal hydrogen carbonate salt, alkali metal hydroxide, and tertiary organic amines such as triethylamine or diisopropylethylamine. Examples of the solvent which can be used include aromatic hydrocarbons such as benzene or toluene, nitriles such as acetonitrile, propionotirile, or butyronitrile, halogenated hydrocarbons such as chloroform or dichloromethane, ethers such as diethyl ether or tetrahydrofuran (hereinbelow, referred to as THF), water, or a mixture thereof. The reaction temperature is usually –30° C. to 40° C., and preferably 0° C. to room temperature. The reaction time is usually 0.5 to 24 hours, and preferably 0.5 to 3 hours.

Meanwhile, the compound (2) is either commercially available or can be produced by a known method.

Step 2: Mitsunobu Reaction

The compound (5) can be produced by reacting the compound (3) and the compound (4) in the presence of a dehydration and condensation agent, and in the absence of a solvent, or in an inert solvent.

The use amount of the compound (4) is, with respect to the compound (3), generally 1 to 3 equivalents, and preferably 1 to 1.5 equivalents. Examples of the dehydration and condensation agent which can be used include a combination of an azodicarboxylic acid compound such as diethyl azodicarboxylate or 1,1'-azobis(N,N-dimethyl formamide) and phosphines such as triphenyl phosphine or tri-n-butyl phosphine. The use amount of the dehydration and condensation agent is, with respect to the compound (3), generally 1 to 3 equivalents, and preferably 1 to 1.5 equivalents for each. Examples of the solvent which can be used include aromatic hydrocarbons such as benzene or toluene, halogenated hydrocarbons such as chloroform or dichloromethane, ethers such as diethyl ether or THF, and amides such as N,N-dimethyl formamide (hereinbelow, referred to as DMF) or dimethyl acetamide. The reaction temperature is usually –30° C. to 40° C., and preferably 0° C. to room temperature. The reaction time is usually 1 to 48 hours, and preferably 1 to 24 hours.

Meanwhile, the compound (4) is either available or can be produced by a known method.

Step 3: Nosyl Deprotection Reaction

The compound (6) can be produced by reacting the compound (5) in the presence of a base and a deprotecting agent, and in the absence of a solvent, or in an inert solvent.

The deprotecting agent which can be used is, for example, primary or secondary organic amines such as n-propyl amine or pyrrolidine; and thiols such as 1-dodecane thiol, thiophenol, or thioglycolic acid. The use amount of the deprotecting agent is, with respect to the compound (5), generally 1 to 5 equivalents, and preferably 1 to 2 equivalents. Examples of the base which can be used include alkali metal carbonate salt, alkali metal hydrogen carbonate salt, alkali metal hydride, alkali metal alkoxide, and tertiary organic amines. Examples of the solvent which can be used include nitriles such as acetonitrile, propionotirile, or butyronitrile, halogenated hydrocarbons such as chloroform or dichloromethane, amides such as DMF or dimethyl acetamide, or a mixture thereof. The reaction temperature is usually −30° C. to 40° C., and preferably 0° C. to room temperature. The reaction time is usually 1 to 48 hours, and preferably 1 to 24 hours.

Step 4: Alkylation

The compound (8) can be produced by reacting the compound (6) and the compound (7) in the presence of a base, and if necessary with an additive, in the absence of a solvent, or in an inert solvent. The use amount of the compound (7) is, with respect to the compound (6), generally 1 to 5 equivalents, and preferably 1 to 3 equivalents. Examples of the base which can be used include alkali metal carbonate salt, alkali metal hydrogen carbonate salt, alkali metal hydride, alkali metal alkoxide, and organic amines such as triethylamine, diisopropylethylamine, or pyridine. Examples of the additive which can be used include a phase transfer catalyst such as alkali metal iodide, tetrabutylammonium salt, or crown ether. Examples of the solvent which can be used include aromatic hydrocarbons such as benzene or toluene, nitriles such as acetonitrile, propionotirile, or butyronitrile, halogenated hydrocarbons such as chloroform or dichloromethane, ketones, ethers such as diethyl ether or THF, alcohols such as methanol, ethanol, or 2-propanol, amides such as DMF or dimethyl acetamide, or a mixture thereof. The reaction temperature is usually room temperature to 150° C., and preferably room temperature to 100° C. The reaction time is usually 5 to 72 hours, and preferably 8 to 48 hours.

Step 5: Tetrazole cyclization

The compound (9) can be produced by, when at least one of $U^1$ and $U^2$ of the compound (8) is a cyano group, a known method for converting a cyano group to a tetrazolyl group, for example, a method of having the reaction in an inert solvent in the presence of an azide compound.

Examples of the azide compound which can be used include azide metal salt, trialkyl tin azide, ammonium azide, and trimethylsilyl azide. For the present step, an additive may be suitably used, if necessary. Examples of the additive which can be used include aluminum chloride, quaternary ammonium salt, magnesium salt, dialkyl tin oxide, and zinc chloride. Examples of the solvent which can be used include aromatic hydrocarbons such as benzene or toluene, halogenated hydrocarbons such as chloroform or dichloromethane, ethers such as diethyl ether or THF, amides such as DMF or dimethyl acetamide, or a mixture thereof. The reaction temperature is usually room temperature to 180° C., and preferably 50° C. to 120° C. The reaction time is usually 5 to 72 hours, and preferably 8 to 48 hours.

Step 6: Hydrolysis

The compound (1) of General Formula (1) can be produced by, when at least one of $Q^1$ and $Q^2$ of the compound (9) is $CO_2R^6$, performing de-esterification of the compound (9).

The de-esterification reaction can be performed typically by a method well known in the field of synthetic organic chemistry, depending on a type of ester group ($CO_2R^6$). For example, by performing the hydrolysis reaction in the presence of a base, the compound of General Formula (1) can be produced.

Examples of the base which can be used include alkali metal carbonate salt, alkali metal hydroxide, alkali earth metal hydroxide, and alkali metal alkoxide. Examples of the solvent which can be used include ethers such as diethyl ether or THF, alcohols such as methanol, ethanol, or 2-propanol, water, or a mixture thereof. Meanwhile, for the present hydrolysis reaction, water is essential. The reaction temperature is usually 0° C. to 150° C., and preferably room temperature to 80° C. The reaction time is usually 1 to 48 hours, and preferably 3 to 24 hours.

Meanwhile, when both $W^1$ and $W^2$ in General Formula (1) are a carboxyl group, Step 5 can be omitted. Further, when both $W^1$ and $W^2$ are a tetrazolyl group, Step 6 can be omitted. Further, by performing a de-esterification reaction of the optically active compounds (8) and (9), the optically active compound of General Formula (1) can be produced. Further, with regard to the compound of General Formula (1), the optically active compound of General Formula (1) can be also produced via HPLC fractionation using a chiral column.

When V is —O—, —CH(CH₃)O—, or —CH₂O—, the compound of General Formula (1) can be produced by obtaining the compound (8) according to the method of the scheme shown below from the compound (11), which is obtained from the compound (10) of the following formula according to the same method as above Step 1 to Step 4

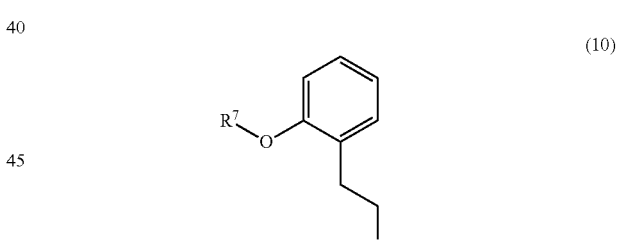

(10)

wherein $R^7$ represents a protecting group for hydroxyl group).

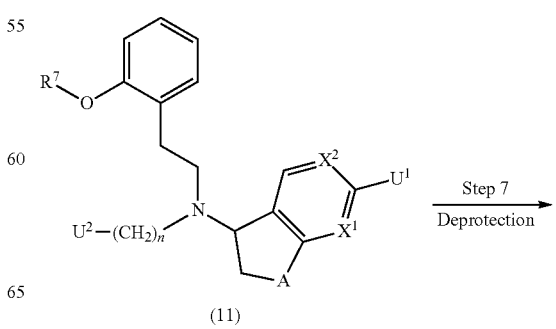

(11)

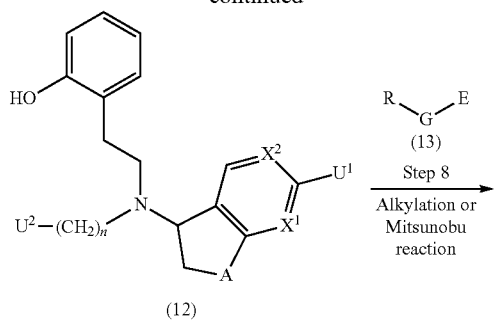

(12)

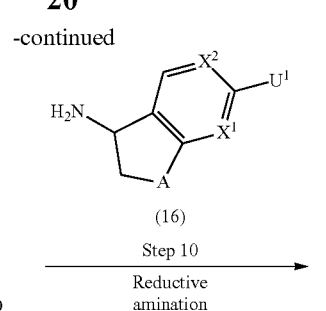

(15)

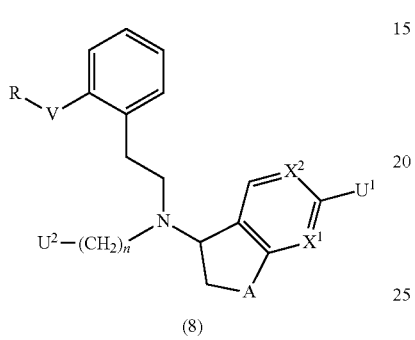

(8)

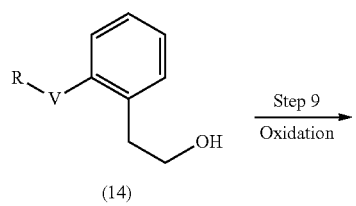

(14)

wherein A, n, $X^1$, $X^2$, R, $U^1$, $U^2$, E and $R^7$ are as defined above, V is —O—, —CH(CH$_3$)O— or —CH$_2$O—, and G is a single bond or a methylene group). Meanwhile, the compound (10) is either commercially available or can be produced by a known method.

Step 7: Deprotection

The compound (12) can be produced by performing deprotection of the compound (11).

The deprotection can be performed typically by a method well known in the field of synthetic organic chemistry (for example, the method disclosed by T. W. Greene, P. G. Wuts, Greene's Protective Groups in Organic Synthesis. Fourth Edition, 2006, John Wiley & Sons, Inc.).

Step 8: Alkylation and Mitsunobu reaction

When E in the compound (13) is a leaving group, the compound (8) can be produced from the compound (12) and the compound (13) according to the same method as Step 4 above.

Further, when E in the compound (13) is a hydroxyl group, the compound (8) can be produced from the compound (12) and the compound (13) according to the same method as Step 2 above.

Further, the compound of General Formula (1) can be also produced by obtaining the compound (6) according to the method of the following scheme.

wherein A, $X^1$, $X^2$, R, V and $U^1$ are as defined above).

Step 9: Oxidation

The compound (15) can be produced by reacting the compound (14) and an oxidizing agent in an inert solvent.

Examples of the oxidizing agent which can be used include a hypervalent iodine compounds such as 1,1,1-triacetoxy-1, 1-dihydro-1,2-benziodoxol-3(1H)-one (DMP) or 1-hydroxy-1,2-benziodoxol-3(1H)-one-1-oxide (IBX); combination of aluminum alkoxide and a hydrogen acceptor such as benzoquinone, benzophenone, acetone, or benzaldehyde; combination of tetrapropylammonium perruthenate (TPAP) or 2,2,6, 6-tetramethyl-1-piperidinyloxy radical (TEMPO) and a co-oxidizing agent such as hypochlorite, hypobromide, or N-chlorosuccinimide; and combination of dimethyl sulfoxide (hereinbelow, referred to as DMSO) and an electrophilic activating reagent such as dicyclohexylcarbodiimide, phosphorus pentoxide, acetic anhydride, or oxalyl chloride. The use amount of the oxidizing agent is, with respect to the compound (14), generally 1 to 10 equivalents, and preferably 1 to 3 equivalents. For the present step, a base such as pyridine or sodium hydrogen carbonate can be added, if necessary. Examples of the solvent which can be used include aromatic hydrocarbons such as benzene or toluene, nitriles such as acetonitrile, propionitrile, or butyronitrile, halogenated hydrocarbons such as chloroform or dichloromethane, ethers such as diethyl ether or THF, esters such as ethyl acetate, propyl acetate, or butyl acetate, amides such as DMF or dimethyl acetamide, sulfoxides such as DMSO or sulfolane, or a mixture thereof. The reaction temperature is usually −30° C. to 100° C., and preferably 0° C. to room temperature. The reaction time is usually 0.5 to 24 hours, and preferably 1 to 8 hours.

Step 10: Reductive amination

The compound (6) can be produced by reacting the compound (15) and the compound (16) in the presence or absence of an acid, and in the absence of a solvent, or in an inert solvent to obtain first a Schiff base followed by reacting it in the presence of a reducing agent.

The use amount of the compound (16) is, with respect to the compound (15), generally 1 to 3 equivalents, and preferably 1 to 1.5 equivalents. Examples of the acid which can be used include inorganic acid such as hydrochloric acid, hydrobromic acid, phosphoric acid, or sulfuric acid, and an organic acid such as formic acid, acetic acid, propinonic acid, methane sulfonic acid, or p-toluene sulfonic acid. Examples of the reducing agent which can be used include a borohydride compound such as borane-tetrahydrofuran complex, sodium borohydride, sodium cyanoborohydride, sodium triacetoxyborohydride; an aluminum hydride compound such as lithium aluminum hydride; and hydrogen. The use amount of the reducing agent is, with respect to the compound (15), generally 1 to 10 equivalents, and preferably 1 to 5 equivalents. Examples of the solvent which can be used include aromatic hydrocarbons such as benzene or toluene, halogenated hydrocarbons such as chloroform or dichloromethane, ethers such as diethyl ether or THF, esters such as ethyl acetate, propyl acetate, or butyl acetate, alcohols such as methanol, ethanol, or 2-propanol, or a mixture thereof. The reaction temperature is usually −78° C. to 150° C., and preferably 0° C. to 60° C. The reaction time is usually 5 minutes to 24 hours, and preferably 30 minutes to 4 hours.

Meanwhile, the compound (16) is either commercially available or can be produced by a known method.

The compound of the present invention which is obtained as described above has sGC activating function with excellent heme-independent property as shown in the following test examples. Thus, the compound of the present invention is useful as a pharmaceutical agent for prevention and treatment of disorders of an animal including human beings that are related with sGC, in particular, various disorders for which the sGC activating function is effective. Examples of the disorders include heart failure, hypertension, pulmonary hypertension, and ischemic heart disease.

When the compound of the present invention is used as a pharmaceutical agent, the administration can be made by either oral administration or parenteral administration. The dosage of the compound of the present invention is appropriately determined according to individual cases in consideration of, for example, the disease or symptom to be treated, the age, body weight or gender of the subject of administration. Conventionally, in the case of oral administration, the dosage of the compound of the present invention for an adult (body weight of about 60 kg) per day is suitably 1 mg to 1000 mg, preferably 3 mg to 300 mg, and more preferably 10 mg to 200 mg, and it is administered once or in 2 to 4 divided doses. Furthermore, in the case of intravenous administration, the dosage for an adult per day is suitably 0.01 mg to 100 mg, preferably 0.01 mg to 50 mg, and more preferably 0.01 mg to 20 mg, per kilogram of the weight, and it is administered once or in multiple divided doses a day.

The pharmaceutical composition of the present invention can be prepared by a general method using at least one kind of the compound of the present invention and a pharmaceutically acceptable additive.

Examples of the pharmaceutical composition of the present invention for oral administration include a tablet, a pill, a capsule, a granule, powder, an emulsion, a solution, a suspension, a syrup, and an elixir. They can be generally prepared as a pharmaceutical composition in which at least one kind of the compound of the present invention and an additive such as pharmaceutically acceptable diluent, an excipient, or a carrier are admixed. It is also possible to contain an additive such as a binder, a disintegrating agent, a lubricating agent, a swelling agent, a swelling aid, a coating agent, a plasticizer, a stabilizing agent, an anti-septic agent, an anti-oxidizing agent, a coloring agent, a dissolution aid, a suspension agent, an emulsifying agent, a sweetening agent, a preservative, a buffer agent, or a wetting agent.

Examples of the pharmaceutical composition of the present invention for parenteral administration include an injection solution, a suppository, an eye drop, an inhaling agent, an ointment, a gel, a crème, and a patch. They can be generally prepared as a pharmaceutical composition in which at least one kind of the compound of the present invention and an additive such as pharmaceutically acceptable diluent, auxiliary agent, or a carrier are admixed. It is also possible to contain an additive such a stabilizing agent, an anti-septic agent, a dissolution aid, a moisturizing agent, a preservative, an anti-oxidizing agent, a flavoring agent, a gelling agent, a neutralizing agent, a buffer agent, an isotonic agent, a surfactant, a coloring agent, a buffering agent, a thickening agent, a wetting agent, a filling agent, an absorption promoter, a suspension agent, or a binder.

Further, as long as it is not against the purpose of the present invention, the pharmaceutical composition containing the compound of the present invention may suitably contain other kind of a pharmaceutically effective component like diuretics.

Hereinbelow, the present invention is specifically described by way of examples, however, the present invention is not limited to them.

Reference Example 1

Methoxymethyl 2-(2-nitrovinyl)phenyl ether

2-Methoxymethoxybenzaldehyde (16.4 g) was suspended in nitromethane (54 mL), added with ammonium acetate (5.95 g), and stirred for 30 minutes at 80° C. After cooling to room temperature, the solvent was evaporated under reduced pressure and the residue was suspended in water and then extracted with ethyl acetate. The organic layer was washed with a saturated aqueous solution of sodium hydrogen carbonate and saturated brine in order and dried over anhydrous sodium sulfate. The solvent was then evaporated under reduced pressure. The residues were purified by diol silica gel column chromatography (5% ethyl acetate/hexane) to obtain the title compound (11.6 g) as a yellow oil.

$^1$H-NMR (CDCl$_3$) δ: 8.22 (1H, d, J=13.6 Hz), 7.83 (1H, d, J=13.6 Hz), 7.50-7.41 (2H, m), 7.23 (1H, dd, J=8.4, 0.9 Hz), 7.07 (1H, ddd, J=8.4, 7.5, 1.1 Hz), 5.33 (2H, s), 3.52 (3H, s).

Reference Example 2

2-(2-Methoxymethoxyphenyl)ethylamine

Lithium aluminum hydride (6.30 g) was suspended in tetrahydrofuran (hereinbelow, THF) (400 mL), added dropwise with a THF solution (100 mL) of Reference Example 1 (11.6 g) under ice cooling, and heated at reflux for 30 minutes. Under ice cooling, sodium sulfate decahydrate (21.4 g) was added in small portions, stirred for 15 minutes at room temperature, and filtered through Celite. The solvent was evaporated under reduced pressure. The residues were purified by silica gel column chromatography (20% methanol/chloroform) to obtain the title compound (6.73 g) as a yellow oil.

$^1$H-NMR (CDCl$_3$) δ: 7.21-7.15 (2H, m), 7.09-7.06 (1H, m), 6.97-6.92 (1H, m), 5.21 (2H, s), 3.48 (3H, s), 2.95 (2H, t, J=6.9 Hz), 2.79 (2H, t, J=6.9 Hz).

Reference Example 3

Methyl 3-mercaptobenzoate

3-Mercaptobenzoic acid (10.0 g) was suspended in methanol (310 mL), added with sulfuric acid (0.3 mL), and stirred for 24 hours under reflux with heating. After cooling to room temperature, the solvent was evaporated under reduced pressure and water was added to residues. After adjusting to pH 8 by using a saturated aqueous solution of sodium hydrogen carbonate, it was extracted with ethyl acetate and dried over anhydrous sodium sulfate. After distilling the solvent under reduced pressure, the residues were purified by silica gel column chromatography (10% ethyl acetate/hexane) to obtain the title compound as a colorless oil.

$^1$H-NMR (CDCl$_3$) δ: 7.95 (1H, dd, J=2.0, 1.5 Hz), 7.82 (1H, ddd, J=7.7, 1.5, 1.3 Hz), 7.45 (1H, ddd, J=7.9, 2.0, 1.3 Hz), 7.31 (1H, dd, J=7.9, 7.7 Hz), 3.91 (3H, s), 3.54 (1H, s).

Reference Example 4

3-(3-Methoxycarbonylphenylsulfanyl)propionic acid

Reference Example 3 (10.3 g) was dissolved in acetone (150 mL), added with potassium carbonate (17.0 g) and 3-bromopropionic acid (10.3 g) under ice cooling, and stirred for 2.5 hours at room temperature. The solvent was evaporated under reduced pressure, and the residues were suspended in water. After adjusting to pH 1 using 6 mol/L hydrochloric acid, it was extracted with ethyl acetate. The organic layer was washed with water and saturated brine in order and dried over anhydrous sodium sulfate. The solvent was then evaporated under reduced pressure. The residues were purified by silica gel column chromatography (50% ethyl acetate/hexane) to obtain the title compound (14.5 g) as a white powder.

$^1$H-NMR (CDCl$_3$) δ: 8.03 (1H, dd, J=1.8, 1.7 Hz), 7.88 (1H, ddd, J=7.9, 1.7, 1.1 Hz), 7.55 (1H, ddd, J=7.7, 1.8, 1.1 Hz), 7.38 (1H, dd, J=7.9, 7.7 Hz), 3.92 (3H, s), 3.22 (2H, t, J=7.3 Hz), 2.70 (2H, t, J=7.3 Hz).

Reference Example 5

Methyl 4-oxothiochromane-7-carboxylate

Reference Example 4 (2.40 g) was suspended in polyphosphoric acid (13 mL) and stirred for 15 minutes at 70° C. After cooling to room temperature, ice and water were added thereto. After extraction with ethyl acetate, the organic layer was washed with a saturated aqueous solution of sodium hydrogen carbonate and saturated brine in order and dried over anhydrous sodium sulfate. The solvent was then evaporated under reduced pressure. The residues were purified by silica gel column chromatography (5% ethyl acetate/hexane) to obtain the title compound (0.36 g) as a colorless oil.

$^1$H-NMR (CDCl$_3$) δ: 8.16 (1H, d, J=8.2 Hz), 7.96 (1H, d, J=1.6 Hz), 7.78 (1H, dd, J=8.2, 1.6 Hz), 3.94 (3H, s), 3.30-3.25 (2H, m), 3.04-3.00 (2H, m).

Reference Example 6

5,6,7,8-Tetrahydroquinolin-5-one N-oxide 5,6,7,8-Tetrahydroquinolin-5-one (7.12 g) was dissolved in dichloromethane (138 mL), added with 3-chloroperbenzoic acid (14.5 g) under ice cooling, and stirred for 4 hours at the same temperature. After adding a saturated aqueous solution of sodium hydrogen carbonate and diluting with chloroform, insoluble was removed by filtration through Celite. After adding 1 mol/L aqueous solution of sodium hydroxide, it was extracted with chloroform and dried over anhydrous sodium sulfate. The solvent was then evaporated under reduced pressure. The residues were suspended in diethyl ether and collected by filtration to obtain the title compound (6.61 g) as a yellow powder.

$^1$H-NMR (CDCl$_3$) δ: 8.44 (1H, dd, J=6.4, 0.9 Hz), 7.87 (1H, dd, J=8.0, 0.9 Hz), 7.32-7.25 (1H, m), 3.24 (2H, t, J=6.2 Hz), 2.74-2.65 (2H, m), 2.28-2.17 (2H, m)

Reference Example 7

2-Cyano-5,6,7,8-tetrahydroquinolin-5-one

Reference Example 6 (6.59 g) was dissolved in dichloromethane (81 mL), added with trimethylsilyl cyanide (17.9 mL) and N, N-dimethylcarbamoyl chloride (8.19 mL) under ice cooling, and stirred for 2.3 hours at room temperature and for 4.5 hours at 30° C. After cooling to room temperature, 2 mol/L aqueous solution of sodium hydroxide was added and stirred vigorously. After that, extraction with chloroform was performed. It was dried over anhydrous sodium sulfate and the solvent was evaporated under reduced pressure. The residues were purified by silica gel column chromatography (4 to 30% ethyl acetate/hexane) to obtain the title compound (6.07 g) as a pale yellow powder.

$^1$H-NMR (CDCl$_3$) δ: 8.40 (1H, d, J=8.0 Hz), 7.68 (1H, d, J=8.0 Hz), 3.21 (2H, t, J=6.3 Hz), 2.79-2.72 (2H, m), 2.31-2.18 (2H, m)

Reference Example 8

5-Oxo-5,6,7,8-tetrahydroquinoline-2-carboxylic acid

Reference Example 7 (6.05 g) was added with conc. hydrochloric acid (70 mL) and stirred for 14 hours under reflux with heating. After cooling to room temperature, conc. hydrochloric acid was evaporated under reduced pressure. The residues were dissolved in a solution of 25% methanol/chloroform, washed with saturated brine, and dried over anhydrous sodium sulfate. The solvent was evaporated under reduced pressure, and the residues were suspended in diisopropyl ether and collected by filtration to obtain the title compound (6.38 g) as a pale yellow powder.

$^1$H-NMR (CDCl$_3$) δ: 8.53 (1H, d, J=8.0 Hz), 8.19 (1H, d, J=8.0 Hz), 3.23 (2H, t, J=6.3 Hz), 2.81-2.75 (2H, m), 2.32-2.21 (2H, m)

Reference Example 9

Methyl 5-oxo-5,6,7,8-tetrahydroquinoline-2-carboxylate

According to the same method as Reference Example 3, the title compound (731 mg) was obtained as a pale yellow powder from Reference Example 8 (980 mg).

$^1$H-NMR (CDCl$_3$) δ: 8.42 (1H, d, J=8.1 Hz), 8.09 (1H, d, J=8.1 Hz), 4.03 (3H, s), 3.27 (2H, t, J=6.0 Hz), 2.78-2.72 (2H, m), 2.30-2.18 (2H, m)

Reference Example 10

2,3-Dihydro-3-oxobenzofuran-6-yl trifluoromethanesulfonate 2,3-Dihydro-6-hydroxy-3-oxobenzofuran (2.00 g) was dissolved in dichloromethane (22 mL), added with pyridine (5.39 mL), and added dropwise with trifluoromethanesulfonic anhydride (2.69 mL) under ice cooling. After stirring at the same temperature for 2 hours, the solvent was evaporated under reduced pressure. The residues were diluted with ethyl acetate, washed with water and saturated brine in order, and dried over anhydrous sodium sulfate. After the solvent was evaporated under reduced pressure, the residues were purified by silica gel column chromatography (5 to 20% ethyl acetate/hexane), suspended in a mixture solution of hexane/diisopropyl ether, and collected by filtration to obtain the title compound (1.84 g) as a yellow powder.

$^1$H-NMR (CDCl$_3$) δ: 7.77 (1H, d, J=8.4 Hz), 7.10 (1H, d, J=2.0 Hz), 7.02 (1H, dd, J=8.4, 2.0 Hz), 4.73 (2H, s)

Reference Example 11

2,3-Dihydro-3-hydroxybenzofuran-6-yl trifluoromethanesulfonate

Reference Example 10 (940 mg) was dissolved in THF (15 mL), added with sodium borohydride (146 mg) in several divided portions under ice cooling, and stirred at the same temperature for 1.5 hours. Under ice cooling, a saturated aqueous solution of ammonium chloride was added followed by extraction with ethyl acetate. The organic layer was washed with saturated brine and dried over anhydrous sodium sulfate, and the solvent was evaporated under reduced pressure. The residues were purified by silica gel column chromatography (6 to 35% ethyl acetate/hexane) to obtain the title compound (785 mg) as a yellow oil.

$^1$H-NMR (CDCl$_3$) δ: 7.47 (1H, d, J=8.2 Hz), 6.86 (1H, dd, J=8.2, 2.2 Hz), 6.80 (1H, d, J=2.2 Hz), 5.40 (1H, ddd, J=6.8, 6.8, 2.8 Hz), 4.66 (1H, dd, J=10.9, 6.8 Hz), 4.53 (1H, dd, J=10.9, 2.8 Hz), 2.01 (1H, d, J=6.8 Hz).

Reference Example 12

Methyl 2,3-dihydro-3-hydroxybenzofuran-6-carboxylate

Reference Example 11 (155 mg) was dissolved in DMF (3.0 mL), added with methanol (0.40 mL), triethylamine (0.38 mL), 1,3-bis(diphenylphosphino)propane (11.2 mg), and palladium acetate (II) (6.10 mg), and stirred in a carbon monoxide atmosphere under ordinary pressure at for 3 hours. After cooling to room temperature, it was diluted with water and extracted with diethyl ether. The organic layer was washed with water and saturated brine in order and dried over anhydrous sodium sulfate. The solvent was evaporated under reduced pressure. The residues were purified by silica gel column chromatography (33% ethyl acetate/hexane) to obtain the title compound (75.0 mg) as a light pink powder.

$^1$H-NMR (CDCl$_3$) δ: 7.66 (1H, dd, J=7.7, 1.5 Hz), 7.52 (1H, d, J=1.5 Hz), 7.47 (1H, d, J=7.7 Hz), 5.41 (1H, ddd, J=6.8, 6.8, 2.9 Hz), 4.62 (1H, dd, J=10.8, 6.8 Hz), 4.50 (1H, dd, J=10.8, 2.9 Hz), 3.91 (3H, s), 2.05 (1H, d, J=6.8 Hz)

Reference Example 13

4-Oxoisochromane-7-yl trifluoromethanesulfonate

According to the same method as Reference Example 10, the title compound (1.70 g) was obtained as a white powder from 7-hydroxyisochroman-4-one (1.00 g).

$^1$H-NMR (CDCl$_3$) δ: 8.16 (1H, d, J=8.6 Hz), 7.32 (1H, dd, J=8.6, 2.4 Hz), 7.18 (1H, d, J=2.4 Hz), 4.93 (2H, s), 4.40 (2H, s).

Reference Example 14

Methyl 4-oxoisochromane-7-carboxylate

According to the same method as Reference Example 12, the title compound (588 mg) was obtained as a white powder from Reference Example 13 (1.50 g).

$^1$H-NMR (CDCl$_3$) δ: 8.13-8.04 (2H, m), 7.92 (1H, s), 4.94 (2H, s), 4.41 (2H, s), 3.96 (3H, s).

Reference Example 15

Methyl 5-hydroxy-6,7,8,9-tetrahydro-5H-benzocycloheptene-2-carboxylate

According to the same method as Reference Example 11, the title compound (526 mg) was obtained as a white powder from methyl 5-oxo-6,7,8,9-tetrahydro-5H-benzocycloheptene-2-carboxylate (523 mg).

$^1$H-NMR (CDCl$_3$) δ: 7.88 (1H, dd, J=8.1, 1.6 Hz), 7.77 (1H, d, J=1.6 Hz), 7.56 (1H, d, J=8.1 Hz), 5.01-4.96 (1H, m), 3.90 (3H, s), 2.99-2.91 (1H, m), 2.79-2.71 (1H, m), 2.08-1.97 (2H, m), 1.89 (1H, d, J=4.0 Hz), 1.85-1.68 (3H, m), 1.46-1.33 (1H, m).

Compounds of Reference Examples 16 to 18 which have been produced according to the same method as Reference Example 15 by using the compound of Reference Examples 5, 9 and 14 are shown in Table 1.

TABLE 1

| Reference Example | Structural formula | $^1$H-NMR |
|---|---|---|
| 16 | (thiochroman-4-ol methyl ester structure) | (CDCl$_3$) δ: 7.82 (1H, d, J = 1.8 Hz), 7.70 (1H, dd, J = 8.1, 1.8 Hz), 7.42 (1H, d, J = 8.1 Hz), 4.83 (1H, ddd, J = 8.8, 5.0, 3.3 Hz), 3.90 (3H, s), 3.30 (1H, ddd, J = 12.7, 11.0, 3.3 Hz), 2.93 (1H, ddd, J = 12.7, 6.1, 3.7 Hz), 2.34 (1H, dddd, J = 13.9, 8.8, 6.1, 3.3 Hz), 2.10 (1H, dddd, J = 13.9, 11.0, 3.7, 3.3 Hz), 1.94 (1H, d, J = 5.0 Hz). |
| 17 | (tetrahydroquinoline-ol methyl ester structure) | (CDCl$_3$) δ: 7.99 (1H, d, J = 8.1 Hz), 7.95 (1H, d, J = 8.1 Hz), 4.91-4.82 (1H, m), 3.99 (3H, s), 3.18-2.93 (2H, m), 2.23-2.00 (2H, m), 1.96 (1H, d, J = 6.4 Hz), 1.93-1.77 (2H, m). |
| 18 | (isochroman-4-ol methyl ester structure) | (CDCl$_3$) δ: 7.93 (1H, d, J = 8.0 Hz), 7.70 (1H, s), 7.53 (1H, d, J = 8.0 Hz), 4.82 (1H, d, J = 15.3 Hz), 4.70 (1H, d, J = 15.3 Hz), 4.63-4.56 (1H, m), 4.09 (1H, dd, J = 12.0, 3.2 Hz), 3.94-3.87 (1H, m), 3.92 (3H, s), 2.46 (1H, d, J = 9.3 Hz). |

Reference Example 19

4-(Phenylsulfanylmethyl)benzyl alcohol

Methyl 4-(phenylsulfanylmethyl)benzoate (1.07 g) was dissolved in THF (14 mL), added with lithium aluminum hydride (200 mg) in small portions under ice cooling, and stirred for 40 minutes at the same temperature. Under ice cooling, sodium sulfate decahydrate was added in small portions and filtered through Celite. The solvent was evaporated under reduced pressure. The residues were suspended in hexane and collected by filtration to obtain the title compound (910 mg) as a white powder.

$^1$H-NMR (DMSO-D$_6$) 7.34-7.12 (9H, m), 5.10 (1H, t, J=5.7 Hz), 4.44 (2H, d, J=5.7 Hz), 4.21 (2H, s)

Reference Example 20

N-[4-(Tetrahydro-2H-pyran-2-yloxymethyl)benzyl]-N-phenyl-2-nitrobenzenesulfonamide N-Phenyl-2-nitrobenzenesulfone amide (1.95 g) was dissolved in DMF (15 mL), added with a DMF (3 mL) solution of potassium carbonate (1.16 g) and 2-(4-chloromethylbenzyloxyl)tetrahydro-2H-pyrane (2.02 g) under ice cooling and stirred for 18 hours at 40° C. After cooling to room temperature, the solvent was evaporated under reduced pressure. The residues were suspended in water and extracted with ethyl acetate. The organic layer was washed with water and saturated brine in order and dried over anhydrous sodium sulfate. The solvent was then evaporated under reduced pressure. The residues were purified by silica gel column chromatography (33% ethyl acetate/hexane) to obtain the title compound (3.29 g) as a yellow oil.

$^1$H-NMR (CDCl$_3$) δ: 7.66-7.64 (2H, m), 7.54-7.42 (2H, m), 7.27-7.17 (7H, m), 7.12-7.06 (2H, m), 4.95 (2H, s), 4.73 (1H, d, J=12.1 Hz), 4.68-4.66 (1H, m), 4.45 (1H, d, J=12.1 Hz), 3.92-3.85 (1H, m), 3.54-3.49 (1H, m), 1.89-1.51 (6H, m).

Reference Example 21

N-(4-Hydroxymethylbenzyl)-N-phenyl-2-nitrobenzenesulfonamide

Reference Example 20 (3.37 g) was dissolved in methanol (35 mL), added with p-toluenesulfonic acid monohydrate (133 mg), and stirred for 30 minutes at room temperature. The solvent was evaporated under reduced pressure and the residues were dissolved in ethyl acetate. The organic layer was washed with a saturated aqueous solution of sodium hydrogen carbonate and saturated brine in order and dried over anhydrous sodium sulfate. The solvent was then evaporated under reduced pressure. The residues were purified by silica gel column chromatography (50% ethyl acetate/hexane) to obtain the title compound (2.57 g) as a pale yellow powder.

$^1$H-NMR (CDCl$_3$) δ: 7.66-7.65 (2H, m), 7.54-7.43 (2H, m), 7.26-7.17 (7H, m), 7.10-7.06 (2H, m), 4.95 (2H, s), 4.64 (2H, d, J=5.1 Hz), 1.63 (1H, t, J=5.1 Hz).

Reference Example 22

4-(3-Methyl-1-butyn-1-yl)benzyl alcohol

4-Iodobenzyl alcohol (1.00 g) was dissolved in DMF (17 mL), added with copper (1) iodide (97.7 mg), triethylamine (0.89 mL), and 3-methyl-1-butyne (1.27 mL), and stirred for 10 minutes in argon atmosphere. Subsequently, it was added with bis(triphenylphosphine)palladium (II) chloride (300 mg) and stirred for 4.3 hours at room temperature in argon atmosphere. After filtration through Celite, it was washed with ethyl acetate and the solvent was evaporated under reduced pressure. The residues were purified by silica gel column chromatography (6 to 40% ethyl acetate/hexane) to obtain the title compound as a yellow oil.

$^1$H-NMR (CDCl$_3$) δ: 7.38 (2H, d, J=8.3 Hz), 7.27 (2H, d, J=8.3 Hz), 4.67 (2H, d, J=5.5 Hz), 2.85-2.70 (1H, m), 1.66 (1H, t, J=5.5 Hz), 1.26 (6H, d, J=7.0 Hz).

Compounds of Reference Examples 23 to 24, which have been produced by using the corresponding materials according to the same method as Reference Example 22, are shown in Table 2.

TABLE 2

| Reference Example | Structural formula | $^1$H-NMR |
|---|---|---|
| 23 | (cyclopropyl-C≡C-C$_6$H$_4$-CH$_2$OH) | (CDCl$_3$) δ: 7.36 (2H, d, J = 8.3 Hz), 7.26 (2H, d, J = 8.3 Hz), 4.67 (2H, d, J = 4.9 Hz), 1.66 (1H, br s), 1.50-1.39 (1H, m), 0.91-0.76 (4H, m). |
| 24 | (cyclohexyl-C≡C-C$_6$H$_4$-CH$_2$OH) | (CDCl$_3$) δ: 7.39 (2H, d, J = 8.2 Hz), 7.27 (2H, d, J = 8.2 Hz), 4.67 (2H, s), 2.64-2.53 (1H, m), 1.94-1.82 (2H, m), 1.82-1.69 (2H, m), 1.68-1.45 (3H, m), 1.44-1.29 (3H, m). |

Reference Example 25

4-((E)-2-Cyclohexylvinyl)benzyl alcohol

4-Iodobenzyl alcohol (2.34 g) was dissolved in DMF (40 mL), added with vinylcyclohexane (1.32 g), triethylamine (1.81 mL), and bis(triphenylphosphine)palladium (II) chloride (700 mg), and stirred for 23 hours at 80° C. After cooling to room temperature, the solvent was evaporated under reduced pressure, and the residues were purified by silica gel column chromatography (8 to 30% ethyl acetate/hexane) to obtain the title compound (672 mg) as a yellow solid.
$^1$H-NMR (CDCl$_3$) δ: 7.34-7.19 (4H, m), 6.29 (1H, d, J=16.0 Hz), 6.13 (1H, dd, J=16.0, 6.8 Hz), 4.67-4.56 (3H, m), 2.15-2.00 (1H, m), 1.82-1.51 (4H, m), 1.37-1.04 (6H, m)

Reference Example 26

4-(2-Cyclohexylethyl)benzyl alcohol

Reference Example 25 (283 mg) was dissolved in methanol (7.0 mL), added with palladium-fibroin (57.0 mg), and stirred in a hydrogen atmosphere under ordinary pressure at room temperature for 45 minutes. After filtration through Celite, it was washed with methanol and the solvent was evaporated under reduced pressure. The residues were purified by silica gel column chromatography (5 to 35% ethyl acetate/hexane) to obtain the title compound (206 mg) as a yellow powder.
$^1$H-NMR (CDCl$_3$) δ: 7.27 (2H, d, J=8.1 Hz), 7.17 (2H, d, J=8.1 Hz), 4.66 (2H, d, J=5.9 Hz), 2.66-2.57 (2H, m), 1.82-1.60 (5H, m), 1.57-1.44 (3H, m), 1.32-1.10 (4H, m), 1.01-0.85 (2H, m)

Reference Example 27

Methyl trans-4-((E)-2-phenylvinyl)cyclohexane carboxylate

According to the same method as Reference Example 25, the title compound (326 mg) was obtained as a brown solid from methyl trans-4-vinylcyclohexane carboxylate (492 mg).
$^1$H-NMR (CDCl$_3$) δ: 7.39-7.12 (5H, m), 6.36 (1H, d, J=15.9 Hz), 6.14 (1H, dd, J=15.9, 7.0 Hz), 3.68 (3H, s), 2.35-2.21 (1H, m), 2.19-1.99 (3H, m), 1.97-1.87 (2H, m), 1.60-1.43 (2H, m), 1.30-1.14 (2H, m)

Reference Example 28 trans-4-((E)-2-Phenylvinyl)cyclohexylmethyl alcohol

According to the same method as Reference Example 19, the title compound (99.0 mg) was obtained as a white powder from Reference Example 27 (120 mg).
$^1$H-NMR (CDCl$_3$) δ: 7.38-7.22 (4H, m), 7.21-7.14 (1H, m), 6.36 (1H, d, J=16.0 Hz), 6.16 (1H, dd, J=16.0, 7.0 Hz), 3.48 (2H, d, J=6.2 Hz), 2.17-2.01 (1H, m), 1.95-1.79 (4H, m), 1.64-1.31 (2H, m), 1.30-1.15 (2H, m), 1.12-0.96 (2H, m)

Reference Example 29

Methyl trans-4-(2-phenylethyl)cyclohexane carboxylate

Reference Example 27 (200 mg) was dissolved in methanol (5.0 mL), added with 5% palladium-carbon (80.0 mg), and stirred in a hydrogen atmosphere under 3 atm at room temperature for 7.3 hours. After filtration through Celite, it was washed with methanol and the solvent was evaporated under reduced pressure. The residues were diluted with ethyl acetate, washed with saturated brine, and dried over anhydrous sodium sulfate. The solvent was evaporated under reduced pressure, and the residues were purified by silica gel column chromatography (5% ethyl acetate/hexane) to obtain the title compound (192 mg) as a colorless oil.
$^1$H-NMR (CDCl$_3$) δ: 7.31-7.23 (2H, m), 7.21-7.11 (3H, m), 3.66 (3H, s), 2.66-2.58 (2H, m), 2.25 (1H, tt, J=12.3, 3.5 Hz), 2.03-1.93 (2H, m), 1.92-1.83 (2H, m), 1.57-1.20 (5H, m), 0.97 (2H, ddd, J=16.3, 13.4, 3.5 Hz)

Reference Example 30 trans-4-(2-Phenylethyl)cyclohexylmethyl alcohol

According to the same method as Reference Example 19, the title compound (166 mg) was obtained as a colorless oil from Reference Example 29 (190 mg).
$^1$H-NMR (CDCl$_3$) δ: 7.31-7.23 (2H, m), 7.21-7.12 (3H, m), 3.45 (2H, d, J=6.4 Hz), 2.66-2.59 (2H, m), 1.91-1.74 (4H, m), 1.60-1.16 (5H, m), 1.06-0.82 (4H, m).

Reference Example 31

Methyl cis-4-((E)-2-phenylvinyl)cyclohexane carboxylate

Benzyltriphenylphosphonium bromide (2.94 g) was dissolved in THF (23.0 mL), added at −20° C. with potassium tert-butoxide (1.07 g) in small portions, and stirred for 1 hour at the same temperature. Subsequently, a THF (6.0 mL) solution of methyl cis-4-formylcyclohexane carboxylate (1.00 g) was added dropwise over 35 minutes, and stirred for 1.6 hours at the same temperature. After raising the temperature to room temperature, it was stirred after adding water and extracted with toluene. The organic layer was washed with water and saturated brine in order. After drying over anhydrous sodium sulfate, the solvent was evaporated under reduced pressure. The residues were purified by silica gel column chromatography (9% ethyl acetate/hexane) to obtain the title compound (268 mg) as a colorless oil.
$^1$H-NMR (CDCl$_3$) δ: 7.37-7.15 (5H, m), 6.37 (1H, d, J=16.6 Hz), 6.22 (1H, dd, J=16.6, 6.6 Hz), 3.69 (3H, s), 2.62-2.50 (1H, m), 2.38-2.24 (1H, m), 2.10-2.00 (3H, m), 1.76-1.42 (5H, m)

Reference Example 32

Methyl cis-4-(2-phenylethyl)cyclohexane carboxylate

According to the same method as Reference Example 29, the title compound (248 mg) was obtained as a colorless oil from Reference Example 31 (268 mg).
$^1$H-NMR (CDCl$_3$) δ: 7.31-7.23 (2H, m), 7.20-7.13 (3H, m), 3.68 (3H, s), 2.64-2.48 (3H, m), 2.05-1.92 (2H, m), 1.67-1.23 (9H, m)

Reference Example 33 cis-4-(2-Phenylethyl)cyclohexylmethyl alcohol

According to the same method as Reference Example 19, the title compound (208 mg) was obtained as a colorless oil from Reference Example 32 (248 mg).

¹H-NMR (CDCl₃) δ: 7.31-7.24 (2H, m), 7.21-7.14 (3H, m), 3.54 (2H, t, J=5.3 Hz), 2.64-2.56 (2H, m), 1.72-1.32 (12H, m), 1.25-1.18 (1H, m)

Reference Example 34

6-Thiochromanecarbaldehyde

6-Bromo-thiochromane (1.00 g) was dissolved in THF (15.0 mL), added dropwise with 2.69 mol/L n-butyl lithium/hexane solution (3.24 mL) at −78° C., and stirred for 1 hour at the same temperature. After adding DMF (0.71 mL) at the same temperature, it was stirred for 16 hours while raising the temperature to room temperature. A saturated aqueous solution of ammonium chloride was added, and after extraction with ethyl acetate, the organic layer was washed with saturated brine. After drying over anhydrous sodium sulfate, the solvent was evaporated under reduced pressure and the residues were purified by silica gel column chromatography (2 to 15% ethyl acetate/hexane) to obtain the title compound (342 mg) as a colorless oil.
¹H-NMR (CDCl₃) δ: 9.85 (1H, s), 7.57-7.48 (2H, m), 7.21 (1H, d, J=8.1 Hz), 3.12-3.05 (2H, m), 2.89 (2H, t, J=6.1 Hz), 2.20-2.10 (2H, m)

Reference Example 35

6-Thiochromanemethyl alcohol

Reference Example 34 (340 mg) was dissolved in methanol (10 mL), added with sodium borohydride (91.2 mg) in several divided portions under ice cooling, and stirred at the same temperature for 1 hour. Under ice cooling, a saturated aqueous solution of ammonium chloride was added followed by stirring. The solvent was evaporated under reduced pressure. After dilution with ethyl acetate, it was washed with water and saturated brine in order. After drying over anhydrous sodium sulfate, the solvent was evaporated under reduced pressure, and the residues were purified by silica gel column chromatography (6 to 50% ethyl acetate/hexane) to obtain the title compound as a colorless oil.
¹H-NMR (CDCl₃) δ: 7.11-7.01 (3H, m), 4.58 (2H, d, J=5.1 Hz), 3.06-2.98 (2H, m), 2.81 (2H, t, J=6.1 Hz), 2.17-2.05 (2H, m)

Reference Example 36

1-Oxo-6-phenylethynyl-1,2,3,4-tetrahydronaphthalene

According to the same method as Reference Example 22, the title compound (1.10 g) was obtained as a yellow powder from 5-oxo-5,6,7,8-tetrahydronaphthalen-2-yl trifluoromethanesulfonate (1.47 g).

¹H-NMR (CDCl₃) δ: 8.01 (1H, d, J=7.9 Hz), 7.56-7.51 (2H, m), 7.46-7.34 (5H, m), 2.96 (2H, t, J=6.0 Hz), 2.67 (2H, t, J=6.6 Hz), 2.15 (2H, tt, J=6.6, 6.0 Hz).

Reference Example 37

1-Hydroxy-6-phenylethynyl-1,2,3,4-tetrahydronaphthalene

According to the same method as Reference Example 11, the title compound (485 mg) was obtained as a white powder from Reference Example 36 (493 mg).
¹H-NMR (CDCl₃) δ: 7.58-7.48 (2H, m), 7.43-7.29 (6H, m), 4.79-4.75 (1H, m), 2.87-2.66 (2H, m), 2.08-1.73 (4H, m), 1.59 (1H, bRS).

Reference Example 38

1-Hydroxy-6-(2-phenylethyl)-1,2,3,4-tetrahydronaphthalene

According to the same method as Reference Example 26, the title compound (423 mg) was obtained as a colorless oil from Reference Example 37 (482 mg).
¹H-NMR (CDCl₃) δ: 7.37-7.17 (6H, m), 7.05 (1H, dd, J=7.7, 1.6 Hz), 6.95 (1H, d, J=1.6 Hz), 4.80-4.75 (1H, m), 2.95-2.64 (6H, m), 2.01-1.72 (4H, m), 1.63 (1H, d, J=6.2 Hz).

Reference Example 39

4-(Phenylsulfanylmethyl)benzyl chloride

Reference Example 19 (77.0 mg) was dissolved in dichloromethane (2.0 mL), added with thionyl chloride (30 μL), and stirred for 1.8 hours. The solvent and reagents were evaporated under reduced pressure to obtain the crude product of the title compound as white amorphous.
¹H-NMR (CDCl₃) δ: 7.34-7.14 (9H, m), 4.56 (2H, s), 4.10 (2H, s)

Compounds of Reference Examples 40 to 46, which have been produced by using the corresponding materials according to the same method as Reference Example 39, are shown in Table 3.

TABLE 3

| Reference Example | Structural formula | ¹H-NMR |
|---|---|---|
| 40 | (structure) | (CDCl₃) δ: 7.67-7.64 (2H, m), 7.54-7.43 (2H, m), 7.30-7.18 (7H, m), 7.11-7.07 (2H, m), 4.96 (2H, s), 4.53 (2H, s). |

TABLE 3-continued

| Reference Example | Structural formula | $^1$H-NMR |
|---|---|---|
| 41 | | (CDCl$_3$) δ: 7.37 (2H, d, J = 8.1 Hz), 7.29 (2H, d, J = 8.1 Hz), 4.56 (2H, s), 2.85-2.70 (1H, m), 1.26 (6H, d, J = 7.0 Hz). |
| 42 | | (CDCl$_3$) δ: 7.35 (2H, d, J = 8.2 Hz), 7.28 (2H, d, J = 8.2 Hz), 4.55 (2H, s), 1.50-1.39 (1H, m), 0.92-0.76 (4H, m). |
| 43 | | (CDCl$_3$) δ: 7.38 (2H, d, J = 8.4 Hz), 7.29 (2H, d, J = 8.4 Hz), 4.56 (2H, s), 2.58 (1H, tt, J = 9.1, 3.8 Hz), 1.93-1.82 (2H, m), 1.82-1.69 (2H, m), 1.61-1.46 (3H, m), 1.43-1.28 (3H, m). |
| 44 | | (CDCl$_3$) δ: 7.40-7.27 (4H, m), 6.33 (1H, d, J = 16.0 Hz), 6.19 (1H, dd, J = 16.0, 6.6 Hz), 4.57 (2H, s), 2.23-2.04 (1H, m), 1.93-1.62 (6H, m), 1.43-1.07 (4H, m). |
| 45 | | (CDCl$_3$) δ: 7.29 (2H, d, J = 8.3 Hz), 7.16 (2H, d, J = 8.3 Hz), 4.57 (2H, s), 2.65-2.57 (2H, m), 1.81-1.58 (5H, m), 1.57-1.44 (2H, m), 1.35-1.06 (4H, m), 1.02-0.83 (2H, m). |
| 46 | | (CDCl$_3$) δ: 7.08-7.06 (2H, m), 7.04 (1H, d, J = 1.3 Hz), 4.51 (2H, s), 3.07-2.99 (2H, m), 2.81 (2H, t, J = 6.1 Hz), 2.17-2.06 (2H, m). |

Reference Example 47

2-{2-[(E)-2-[4-((E)-2-Phenylvinyl)phenyl]vinyl]phenyl}ethanol

According to the same method as Reference Example 25, the title compound (4.80 g) was obtained as a yellow solid from 2-(2-bromophenyl)ethyl alcohol (3.42 g) and 4-vinyl-trans-stilbene (4.21 g).

$^1$H-NMR (DMSO-D$_6$) δ: 7.69-7.60 (7H, m), 7.50 (1H, d, J=16.2 Hz), 7.41-7.35 (2H, m), 7.29-7.20 (6H, m), 7.12 (1H, d, J=16.2 Hz), 4.73 (1H, t, J=5.7 Hz), 3.57 (2H, td, J=7.0, 5.7 Hz), 2.93 (2H, t, J=7.0 Hz).

Reference Example 48

2-{2-[2-[4-(2-Phenylethyl)phenyl]ethyl]phenyl}ethanol

According to the same method as Reference Example 29, the title compound (4.56 g) was obtained as a colorless oil from Reference Example 47 (4.80 g).

$^1$H-NMR (DMSO-D$_6$) δ: 7.36-7.22 (4H, m), 7.20-7.08 (9H, m), 4.69 (1H, t, J=5.5 Hz), 3.55 (2H, td, J=7.1, 5.5 Hz), 2.86-2.80 (4H, m), 2.84 (2H, t, J=7.1 Hz), 2.79-2.74 (2H, m), 2.75 (2H, t, J=6.3 Hz).

Reference Example 49

2-{2-[2-[4-(2-Phenylethyl)phenyl]ethyl]phenyl}acetaldehyde

Reference Example 48 (496 mg) was dissolved in DMSO (10 mL), added with IBX (840 mg), and stirred for 1.5 hours at room temperature. It was added with ethyl acetate and water in order and stirred for 1 hour at room temperature. The precipitates were filtered and washed with ethyl acetate. After liquid fractionation, the organic layer was washed with saturated brine and dried over anhydrous sodium sulfate. After that, the solvent was evaporated under reduced pressure. The residues were purified by silica gel column chromatography (10 to 30% ethyl acetate/hexane) to obtain the title compound (422 mg) as a colorless oil.

$^1$H-NMR (DMSO-D6) δ: 9.62 (1H, t, J=1.7 Hz), 7.27-7.22 (5H, m), 7.20-7.15 (4H, m), 7.13-7.07 (4H, m), 3.77 (2H, d, J=1.7 Hz), 2.83 (4H, s), 2.74-2.72 (4H, m).

Reference Example 50

Methyl 5-[2-(2-{2-[4-(2-phenylethyl)phenyl]ethyl}phenyl)ethylamino]-5,6,7,8-tetrahydronaphthalene-2-carboxylate In a argon atmosphere, methyl 5-amino-5,6,7,8-tetrahydronaphthalene-2-carboxylate hydrochloride (311 mg) was dissolved in dichloromethane (26 mL), added with triethylamine (0.18 mL), and stirred for 5 minutes at room temperature. Reference Example 49 (422 mg) and acetic acid (0.11 mL) were added in order and stirred for 10 minutes at the same temperature. Subsequently, sodium triacetoxyborohydride (681 mg) was added under ice cooling followed by stirring for 2 hours at room temperature. A saturated aqueous solution of sodium hydrogen carbonate was added, and extracted with ethyl acetate and dried over anhydrous sodium sulfate. The solvent was evaporated under reduced pressure. The residues were purified by silica gel column chromatography (30 to 70% ethyl acetate/hexane) to obtain the title compound (607 mg) as a colorless oil.

$^1$H-NMR (DMSO-D$_6$) δ: 7.68-7.63 (2H, m), 7.50 (1H, d, J=8.4 Hz), 7.29-7.08 (13H, m), 3.80 (3H, s), 3.73 (1H, bRS), 2.85-2.79 (7H, m), 2.76-2.75 (8H, m), 1.93-1.56 (4H, m).

Reference Example 51

N-[2-(2-Methoxymethoxyphenyl)ethyl]-2-nitrobenzenesulfonamide

Reference Example 2 (6.72 g) was dissolved in dichloromethane (186 mL), added under ice cooling with triethylamine (5.67 mL) and 2-nitrobenzenesulfonyl chloride (10.1 g), and stirred for 1 hour at the same temperature. The solvent was evaporated under reduced pressure. The residues were suspended in ethyl acetate, washed with water and saturated brine in order, and dried over anhydrous sodium sulfate. The solvent was evaporated under reduced pressure and the residues were purified by silica gel column chromatography (20% ethyl acetate/hexane) to obtain the title compound (11.0 g) as a yellow oil.

$^1$H-NMR (CDCl$_3$) δ: 8.10-8.05 (1H, m), 7.83-7.79 (1H, m), 7.72-7.66 (2H, m), 7.18-7.12 (1H, m), 7.04-7.01 (2H, m), 6.86 (1H, ddd, J=8.6, 7.5, 1.3 Hz), 5.51 (1H, t, J=5.5 Hz), 5.19 (2H, s), 3.46 (3H, s), 3.39 (2H, td, J=6.9, 5.5 Hz), 2.87 (2H, t, J=6.9 Hz).

Reference Example 52

N-{2-[2-[4-(2-Phenylethyl)benzyloxy]phenyl]ethyl}-2-nitrobenzenesulfonamide

According to the same method as Reference Example 51, the title compound (2.47 g) was obtained as a yellow oil from 2-{2-[4-(2-phenylethyl)benzyloxy]phenyl}ethylamine (1.83 g).

$^1$H-NMR (CDCl$_3$) δ: 7.97 (1H, dd, J=7.6, 1.7 Hz), 7.76 (1H, dd, J 7.3, 1.8 Hz), 7.66-7.55 (2H, m), 7.37-7.12 (10H, m), 7.01 (1H, dd, J=7.3, 1.6 Hz), 6.86-6.78 (2H, m), 5.43 (1H, t, J=5.7 Hz), 5.00 (2H, s), 3.40 (2H, td, J=6.8, 5.7 Hz), 2.94 (4H, s), 2.86 (2H, t, J=6.8 Hz).

Reference Example 53

Methyl 1-{N-[2-(2-methoxymethoxyphenyl)ethyl]-(2-nitrobenzenesulfonamide)}indane-5-carboxylate Reference Example 51 (733 mg) was dissolved in toluene (10 mL), added under ice cooling with methyl 1-hydroxyindane-5-carboxylate (577 mg), tri-n-butylphosphine (0.75 mL) and 1,1'-azobis(N,N-dimethylformamide) (517 mg), and stirred for 14.5 hours at room temperature. The solvent was evaporated under reduced pressure. The residues were dissolved again in ethyl acetate. It was washed with water and saturated brine in order, and dried over anhydrous sodium sulfate. The solvent was evaporated under reduced pressure and the residues were purified by silica gel column chromatography (20% ethyl acetate/hexane) to obtain the title compound as a yellow oil.

$^1$H-NMR (CDCl$_3$) δ: 8.19-8.16 (1H, m), 7.92 (1H, s), 7.86-7.83 (1H, m), 7.74-7.66 (3H, m), 7.29-7.25 (1H, m), 7.14-7.08 (1H, m), 6.97-6.93 (2H, m), 6.85 (1H, ddd, J=8.4, 7.4, 1.1 Hz), 5.66-5.61 (1H, m), 5.00 (1H, d, J=6.8 Hz), 4.95 (1H, d, J=6.8 Hz), 3.90 (3H, s), 3.38-3.19 (2H, m), 3.27 (3H, s), 3.13-2.78 (3H, m), 2.67-2.49 (2H, m), 2.23-2.11 (1H, m).

Compounds of Reference Examples 54 to 61, which have been produced by using the corresponding compound (4) and the compound of Reference Example 51 or 52 according to the same method as Reference Example 53, are shown in Table 4 and Table 5.

TABLE 4

| Reference Example | Structural formula | ¹H-NMR |
|---|---|---|
| 54 | | (CDCl$_3$) δ: 8.18-8.15 (1H, m), 7.77-7.64 (5H, m), 7.35 (1H, d, J = 8.2 Hz), 7.15-7.09 (1H, m), 7.03 (1H, dd, J = 7.3, 1.6 Hz), 6.96 (1H, d, J = 7.5 Hz), 6.87 (1H, ddd, J = 8.3, 7.3, 0.9 Hz), 5.29 (1H, dd, J = 9.9, 6.0 Hz), 5.04 (1H, d, J = 6.8 Hz), 5.00 (1H, d, J = 6.8 Hz), 3.89 (3H, s), 3.53-3.42 (1H, m), 3.32-3.19 (1H, m), 3.28 (3H, s), 2.92-2.73 (4H, m), 2.27-2.17 (1H, m), 2.09-1.84 (3H, m). |
| 55 | | (CDCl$_3$) δ: 8.02 (1H, dd, J = 8.0, 1.2 Hz), 7.69-7.52 (5H, m), 7.32-7.10 (11H, m), 7.04 (1H, dd, J = 7.4, 1.7 Hz), 6.86-6.80 (2H, m), 5.24-5.19 (1H, m), 4.94 (1H, d, J = 11.5 Hz), 4.87 (1H, d, J = 11.5 Hz), 3.86 (3H, s), 3.57-3.46 (1H, m), 3.22-3.12 (1H, m), 2.94 (4H, s), 2.88-2.62 (3H, m), 2.51-2.40 (1H, m), 2.10-1.99 (1H, m), 1.93-1.71 (3H, m). |
| 56 | | (CDCl$_3$) δ: 7.97 (1H, dd, J = 7.5, 1.3 Hz), 7.73 (1H, d, J = 1.8 Hz), 7.61-7.47 (4H, m), 7.21-7.13 (2H, m), 7.07-7.03 (2H, m), 6.94 (1H, ddd, J = 8.4, 7.3, 1.1 Hz), 5.46-5.43 (1H, m), 5.17 (2H, s), 4.09-3.98 (1H, m), 3.86 (3H, s), 3.53-3.42 (1H, m), 3.40 (3H, s), 3.06-3.00 (2H, m), 2.95-2.91 (2H, m), 2.44-2.40 (1H, m), 2.03-1.78 (4H, m), 1.40-1.30 (1H, m). |
| 57 | | (CDCl$_3$) δ: 8.04 (1H, d, J = 8.4 Hz), 7.72-7.64 (2H, m), 7.59-7.52 (1H, m), 7.47-7.42 (2H, m), 7.32-7.10 (11H, m), 6.99 (1H, dd, J = 7.6, 1.5 Hz), 6.87-6.80 (2H, m), 5.36 (1H, dd, J = 10.7, 6.1 Hz), 4.94 (1H, d, J = 11.4 Hz), 4.90 (1H, d, J = 11.4 Hz), 4.15-4.07 (2H, m), 3.85 (3H, s), 3.61-3.46 (1H, m), 3.15-3.02 (1H, m), 2.94 (4H, s), 2.85-2.67 (2H, m), 2.30-2.08 (2H, m). |

TABLE 4-continued

| Reference Example | Structural formula | ¹H-NMR |
|---|---|---|
| 58 | | (CDCl₃) δ: 8.01 (1H, dd, J = 8.1, 0.9 Hz), 7.75-7.49 (6H, m), 7.31-7.11 (10H, m), 7.00 (1H, dd, J = 7.7, 1.7 Hz), 6.87-6.80 (2H, m), 5.22 (1H, dd, J = 11.2, 4.3 Hz), 4.97 (1H, d, J = 11.5 Hz), 4.92 (1H, d, J = 11.5 Hz), 3.85 (3H, s), 3.67-3.55 (1H, m), 3.40-3.16 (3H, m), 2.96-2.67 (6H, m), 2.46-2.10 (2H, m). |

TABLE 5

| Reference Example | Structural formula | ¹H-NMR |
|---|---|---|
| 59 | | (CDCl₃) δ: 8.02 (1H, dd, J = 8.1, 1.3 Hz), 7.85 (1H, d, J = 8.1 Hz), 7.80 (1H, dd, J = 8.1, 0.5 Hz), 7.72-7.63 (2H, m), 7.56 (1H, ddd, J = 8.1, 6.6, 2.2 Hz), 7.32-7.16 (9H, m), 7.13 (1H, dd, J = 8.1, 1.3 Hz), 7.01 (1H, dd, J = 8.1, 1.3 Hz), 6.88-6.80 (2H, m), 5.30-5.21 (1H, m), 4.93 (1H, d, J = 11.2 Hz), 4.87 (1H, d, J = 11.2 Hz), 3.95 (3H, s), 3.51 (1H, ddd, J = 14.6, 11.5, 5.2 Hz), 3.15 (1H, ddd, J = 14.6, 11.5, 5.2 Hz), 3.04-2.87 (1H, m), 2.94 (4H, s), 2.79-2.59 (3H, m), 2.13-2.00 (1H, m), 1.92-174 (3H, m). |
| 60 | | (CDCl₃) δ: 7.84 (1H, d, J = 7.5 Hz), 7.68-7.59 (3H, m), 7.48 (1H, d, J = 1.1 Hz), 7.44-7.37 (2H, m), 7.32-7.14 (9H, m), 7.12-7.05 (1H, m), 6.80-6.73 (2H, m), 6.69 (1H, dd, J = 7.8, 1.7 Hz), 5.84 (1H, dd, J = 8.8, 3.5 Hz), 4.94 (2H, s), 4.68 (1H, dd, J = 11.2, 8.8 Hz), 4.43 (1H, dd, J = 11.2, 3.5 Hz), 3.87 (3H, s), 3.22 (2H, t, J = 8.2 Hz), 2.97-2.77 (1H, m), 2.92 (4H, s), 2.49-2.34 (1H, m). |
| 61 | | (CDCl₃) δ: 7.91-7.83 (2H, m), 7.68-7.62 (3H, m), 7.50 (1H, d, J = 8.2 Hz), 7.45-7.38 (1H, m), 7.32-7.07 (10H, m), 6.91 (1H, dd, J = 7.3, 1.7 Hz), 6.84-6.75 (2H, m), 5.21-5.17 (1H, m), 4.97 (1H, d, J = 11.6 Hz), 4.90 (1H, d, J = 11.6 Hz), 4.58 (2H, s), 4.21-4.01 (2H, m), 3.90 (3H, s), 3.79-3.69 (1H, m), 3.25-3.15 (1H, m), 2.97-2.79 (5H, m), 2.58-2.50 (1H, m). |

Reference Example 62

Methyl 1-[2-(2-methoxymethoxyphenyl)ethylamino]indane-5-carboxylate

Reference Example 53 (1.08 g) was dissolved in DMF (10 mL), added under ice cooling with thiophenol (0.41 mL) and potassium carbonate (553 mg) and stirred for 18 hours at room temperature. After dilution with water, extracted with diethyl ether. The organic layer was washed with water and saturated brine in order, and dried over anhydrous sodium sulfate. The solvent was evaporated under reduced pressure and the residues were purified by amine silica gel column chromatography (67% ethyl acetate/hexane) to obtain the title compound (638 mg) as a yellow oil.

$^1$H-NMR (CDCl$_3$) δ: 7.88-7.85 (2H, m), 7.32 (1H, d, J=7.7 Hz), 7.20-7.15 (2H, m), 7.08 (1H, dd, J=8.6, 1.1 Hz), 6.95 (1H, ddd, J=8.4, 7.5, 1.1 Hz), 5.20 (2H, s), 4.30 (1H, t, J=7.0 Hz), 3.90 (3H, s), 3.45 (3H, s), 3.05-2.77 (6H, m), 2.49-2.38 (1H, m), 1.91-1.79 (1H, m).

Compounds of Reference Examples 63 to 70, which have been produced by using the compound of Reference Examples 54 to 61 according to the same method as Reference Example 62, are shown in Table 6. Meanwhile, Reference Examples 66, 67, 68 and 70 were isolated as a hydrochloride salt.

TABLE 6

| Reference Example | Structural formula | $^1$H-NMR |
|---|---|---|
| 63 | | (CDCl$_3$) δ: 7.77-7.75 (2H, m), 7.33 (1H, d, J = 8.6 Hz), 7.20-7.15 (2H, m), 7.09-7.06 (1H, m), 6.97-6.92 (1H, m), 5.18 (2H, s), 3.89 (3H, s), 3.82-3.80 (1H, m), 3.44 (3H, s), 3.02-2.69 (6H, m), 1.99-1.66 (4H, m). |
| 64 | | (CDCl$_3$) δ: 7.74-7.72 (2H, m), 7.32-7.16 (12H, m), 6.93-6.88 (2H, m), 5.03 (2H, s), 3.88 (3H, s), 3.78 (1H, t, J = 5.0 Hz), 3.04-2.66 (10H, m), 1.95-1.63 (4H, m). |
| 65 | | (CDCl$_3$) δ: 7.80 (1H, dd, J = 8.0, 1.7 Hz), 7.74 (1H, d, J = 1.7 Hz), 7.34 (1H, d, J = 8.0 Hz), 7.19-7.14 (2H, m), 7.07-7.04 (1H, m), 6.93 (1H, ddd, J = 8.4, 7.3, 1.1 Hz), 5.15 (2H, s), 3.91-3.88 (1H, m), 3.89 (3H, s), 3.40 (3H, s), 2.94-2.71 (6H, m), 1.94-1.38 (6H, m). |
| 66 | | (DMSO-D$_6$) δ: 7.74 (1H, d, J = 8.1 Hz), 7.47 (1H, dd, J = 8.1, 1.7 Hz), 7.39-7.05 (13H, m), 6.92 (1H, t, J = 7.3 Hz), 5.07 (2H, s), 4.64-4.54 (1H, m), 4.44-4.18 (2H, m), 3.82 (3H, s), 3.46-3.00 (4H, m), 2.86 (4H, s), 2.40-2.10 (2H, m). |

TABLE 6-continued

| Reference Example | Structural formula | ¹H-NMR |
|---|---|---|
| 67 | 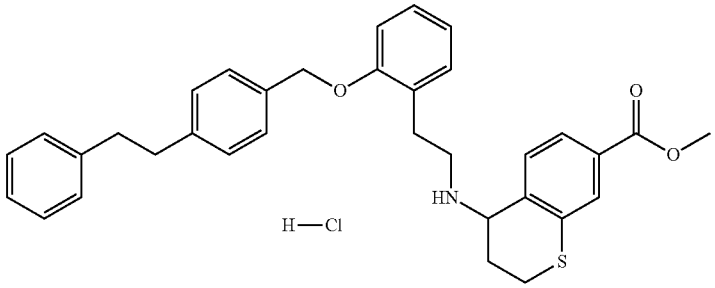 [SMILES: COC(=O)c1ccc2c(c1)SCCC2NCCc1ccccc1OCc1ccc(CCc2ccccc2)cc1 ; Cl] | (DMSO-D$_6$) δ: 7.71 (1H, s), 7.66-7.57 (2H, m), 7.40-7.04 (12H, m), 6.91 (1H, t, J = 7.3 Hz), 5.05 (2H, s), 4.66-4.55 (1H, m), 3.82 (3H, s), 3.35-2.65 (11H, m), 2.10-1.93 (1H, m). |
| 68 | 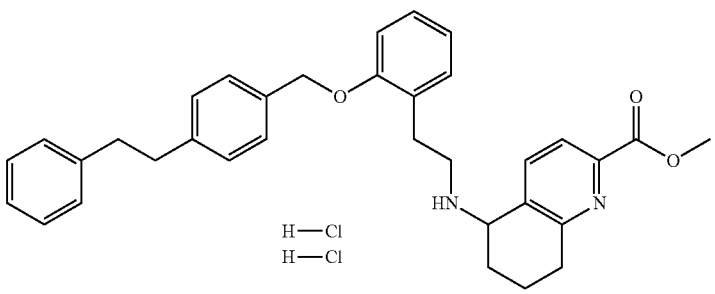 | (DMSO-D$_6$) δ: 8.24 (1H, d, J = 7.5 Hz), 7.85 (1H, d, J = 8.1 Hz), 7.36 (2H, d, J = 8.1 Hz), 7.31-7.12 (9H, m), 7.08 (1H, d, J = 8.1 Hz), 6.91 (1H, t, J = 7.5 Hz), 5.07 (2H, s), 4.68-4.56 (1H, br m), 3.86 (3H, s), 3.20-2.75 (6H, m), 2.87 (4H, s), 2.18-1.91 (3H, m), 1.86-1.70 (1H, m). |
| 69 | 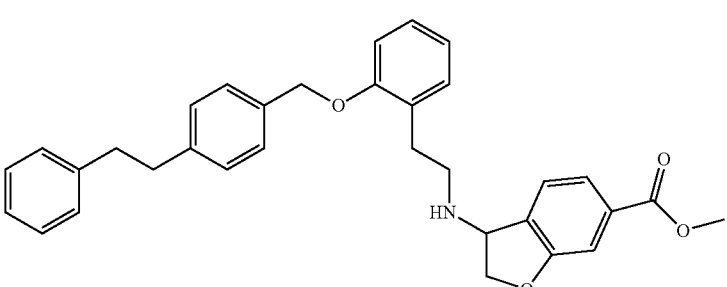 | (CDCl$_3$) δ: 7.56 (1H, dd, J = 7.7, 1.3 Hz), 7.44 (1H, d, J = 1.3 Hz), 7.32-7.24 (5H, m), 7.22-7.13 (7H, m), 6.93-6.87 (2H, m), 5.02 (2H, s), 4.56-4.45 (2H, m), 4.32 (1H, dd, J = 7.8, 2.5 Hz), 3.88 (3H, s), 3.03-2.82 (4H, m), 2.92 (4H, s). |
| 70 | 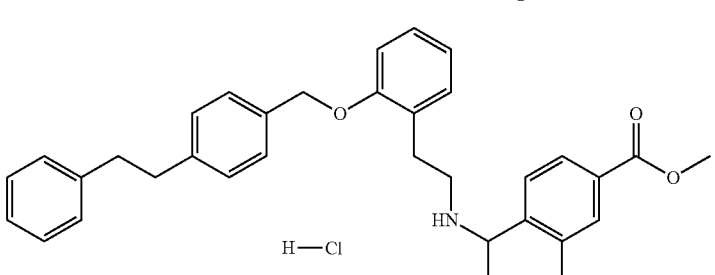 | (DMSO-D$_6$) δ: 7.95-7.72 (3H, m), 7.30-7.14 (11H, m), 7.05 (1H, d, J = 8.2 Hz), 6.90 (1H, t, J = 7.5 Hz), 5.04 (2H, s), 4.96 (1H, d, J = 15.9 Hz), 4.74 (1H, d, J = 15.9 Hz), 4.55-4.44 (2H, m), 3.89-3.80 (1H, m), 3.83 (3H, s), 3.20-2.95 (4H, m), 2.86 (4H, s). |

Reference Example 71

Methyl 1-{N-(4-Methoxycarbonylbutyl)-N-[2-(2-methoxymethoxyphenyl)ethyl]amino}indane-5-carboxylate Reference Example 62 (636 mg) was dissolved in DMF (9.0 mL), added with potassium carbonate (495 mg) and methyl 5-bromovalerate (0.51 mL) and heated for 18.5 hours at 95° C. After cooling to room temperature, the solvent was evaporated under reduced pressure. The residues were suspended in water and extracted with ethyl acetate. The organic layer was washed with water and saturated brine in order, and dried over anhydrous sodium sulfate. The solvent was evaporated under reduced pressure and the residues were purified by silica gel column chromatography (17% ethyl acetate/hexane) to obtain the title compound (568 mg) as a yellow oil.

¹H-NMR (CDCl$_3$) δ: 7.84-7.82 (2H, m), 7.27-7.24 (1H, m), 7.17-7.07 (2H, m), 7.01 (1H, dd, J=8.2, 1.0 Hz), 6.90 (1H, ddd, J=8.4, 7.3, 1.1 Hz), 5.07 (2H, s), 4.57 (1H, t, J=8.0 Hz), 3.90 (3H, s), 3.66 (3H, s), 3.35 (3H, s), 2.97-2.56 (6H, m), 2.52 (2H, t, J=6.9 Hz), 2.29 (2H, t, J=7.2 Hz), 2.23-2.13 (1H, m), 2.02-1.89 (1H, m), 1.74-1.48 (4H, m).

Compounds of Reference Examples 72 to 81, which have been produced by using the compound of Reference Example 50 and Reference Examples 63 to 70 according to the same method as Reference Example 71, are shown in Table 7 and Table 8.

TABLE 7

| Reference Example | Structural formula | ¹H-NMR |
|---|---|---|
| 72 | | (CDCl₃) δ: 7.75-7.70 (3H, m), 7.16-7.06 (2H, m), 7.00 (1H, dd, J = 8.3, 0.9 Hz), 6.89 (1H, ddd, J = 8.6, 7.3, 1.3 Hz), 5.04 (2H, s), 3.98 (1H, dd, J = 9.5, 4.8 Hz), 3.90 (3H, s), 3.66 (3H, s), 3.34 (3H, s), 2.86-2.50 (8H, m), 2.29 (2H, t, J = 7.3 Hz), 2.09-1.97 (2H, m), 1.76-1.46 (6H, m). |
| 73 | | (CDCl₃) δ: 7.71-7.64 (3H, m), 7.31-7.08 (11H, m), 6.91-6.85 (2H, m), 4.93 (2H, s), 3.98-3.92 (1H, m), 3.88 (3H, s), 3.63 (3H, s), 2.92-2.85 (6H, m), 2.76-2.63 (6H, m), 2.43 (2H, t, J = 7.1 Hz), 2.20 (2H, t, J = 7.3 Hz), 2.00-1.90 (2H, m), 1.62-1.37 (4H, m). |
| 74 | | (CDCl₃) δ: 7.79 (1H, dd, J = 7.9, 1.8 Hz), 7.75-7.72 (1H, m), 7.35 (1H, d, J = 7.9 Hz), 7.15-7.10 (1H, m), 7.04-7.00 (2H, m), 6.88 (1H, ddd, J = 8.6, 7.4, 1.3 Hz), 5.14 (1H, d, J = 6.8 Hz), 5.11 (1H, d, J = 6.8 Hz), 4.20-4.13 (1H, m), 3.90 (3H, s), 3.65 (3H, s), 3.42 (3H, s), 2.81-2.47 (7H, m), 2.39-2.33 (1H, m), 2.29 (2H, t, J = 7.1 Hz), 1.90-1.53 (10H, m). |
| 75 | | (CDCl₃) δ: 8.05 (1H, s), 7.51-7.43 (2H, m), 7.39 (1H, d, J = 1.6 Hz), 7.32-7.08 (10H, m), 6.91-6.85 (2H, m), 4.93 (2H, s), 4.21-4.14 (2H, m), 4.07 (1H, t, J = 8.0 Hz), 3.87 (3H, s), 3.64 (3H, s), 2.96-2.83 (5H, m), 2.78-2.55 (3H, m), 2.50-2.30 (4H, m), 2.20 (2H, t, J = 7.3 Hz), 1.95-1.85 (2H, m), 1.76-1.35 (2H, m). |
| 76 | | (DMSO-D₆) δ: 8.16 (1H, s), 7.61-7.55 (2H, m), 7.48 (1H, dd, J = 8.2, 1.8 Hz), 7.29-7.07 (10H, m), 6.98 (1H, d, J = 7.4 Hz), 6.84 (1H, ddd, J = 8.7, 7.4, 1.2 Hz), 4.98 (2H, s), 3.96-3.89 (1H, m), 3.82 (3H, s), 3.56 (3H, s), 3.10-2.87 (5H, m), 2.81-2.62 (4H, m), 1.99-1.85 (1H, m), 1.71-1.55 (6H, m), 1.54-1.34 (4H, m). |

TABLE 7-continued

| Reference Example | Structural formula | ¹H-NMR |
|---|---|---|
| 77 | | (CDCl₃) δ: 7.92 (1H, d, J = 8.1 Hz), 7.77 (1H, d, J = 8.1 Hz), 7.32-7.24 (2H, m), 7.24-7.13 (8H, m), 7.08 (1H, dd, J = 7.6, 1.4 Hz), 6.92-6.84 (2H, m), 4.91 (2H, s), 4.00-3.93 (1H, m), 3.96 (3H, s), 3.64 (3H, s), 3.06-2.81 (3H, m), 2.92 (4H, s), 2.78-2.59 (3H, m), 2.51-2.35 (2H, m), 2.21 (2H, t, J = 7.2 Hz), 2.06-1.97 (2H, m), 1.69-1.35 (6H, m). |

TABLE 8

| 78 | | (CDCl₃) δ: 7.52 (1H, dd, J = 7.8, 1.3 Hz), 7.38 (1H, d, J = 1.3 Hz), 7.32-7.23 (4H, m), 7.22-7.13 (7H, m), 7.09 (1H, dd, J = 7.6, 1.3 Hz), 6.91-6.84 (2H, m), 4.98 (2H, s), 4.69 (1H, dd, J = 8.6, 4.6 Hz), 4.42-4.30 (2H, m), 3.87 (3H, s), 3.64 (3H, s), 2.94-2.60 (4H, m), 2.90 (4H, s), 2.49-2.37 (1H, m), 2.37-2.25 (1H, m), 2.17 (2H, t, J = 7.5 Hz), 1.57-1.31 (4H, m). |
| 79 | | (DMSO-D₆) δ: 7.70 (1H, dd, J = 8.1, 1.8 Hz), 7.61 (1H, d, J = 1.8 Hz), 7.47 (1H, d, J = 8.1 Hz), 7.27-7.06 (11H, m), 6.96 (1H, dd, J = 8.1, 0.9 Hz), 6.83 (1H, ddd, J = 8.5, 7.4, 0.9 Hz), 4.99 (1H, d, J = 12.5 Hz), 4.94 (1H, d, J = 12.5 Hz), 4.69 (1H, d, J = 15.5 Hz), 4.58 (1H, d, J = 15.5 Hz), 3.94-3.81 (3H, m), 3.83 (3H, s), 3.56 (3H, s), 2.89 (4H, s), 2.80-2.49 (6H, m), 2.15 (2H, t, J = 7.1 Hz), 1.55-1.32 (4H, m). |
| 80 | | (DMSO-D₆) δ: 7.71 (1H, d, J = 8.4 Hz), 7.61-7.58 (2H, m), 7.28-7.02 (13H, m), 4.11-3.98 (1H, m), 4.01 (2H, q, J = 7.1 Hz), 3.80 (3H, s), 2.83-2.33 (14H, m), 2.24 (2H, t, J = 6.9 Hz), 2.05-1.85 (2H, m), 1.59-1.47 (8H, m), 1.13 (3H, t, J = 7.1 Hz). |

TABLE 8-continued

| 81 | 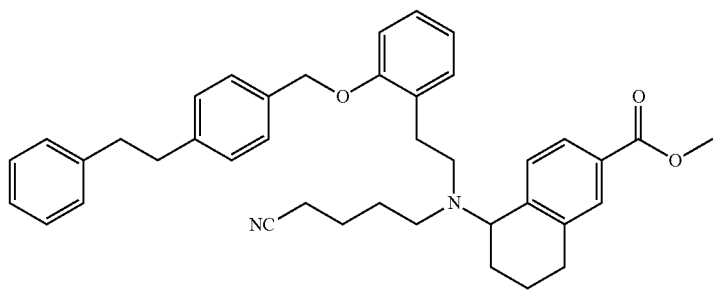 | (CDCl₃) δ: 7.73-7.70 (2H, m), 7.60 (1H, d, J = 7.7 Hz), 7.32-7.09 (11H, m), 6.91-6.87 (2H, m), 4.94 (2H, s), 3.98-3.96 (1H, m), 3.88 (3H, s), 2.94-2.83 (5H, m), 2.77-2.66 (5H, m), 2.47-2.33 (2H, m), 2.11 (2H, t, J = 6.9 Hz), 2.06-1.83 (4H, m), 1.61-1.42 (4H, m). |

Reference Example 82

Methyl 1-{N-(4-methoxycarbonylbutyl)-N-[2-(2-hydroxyphenyl)ethyl]amino}indane-5-carboxylate Reference Example 71 (564 mg) was dissolved in THF (5.5 mL) and methanol (0.5 mL), added with conc. hydrochloric acid (0.6 mL) and stirred for 22 hours at room temperature. The solvent was evaporated under reduced pressure, and the residues were diluted with water and adjusted to pH 8 using a saturated aqueous solution of sodium hydrogen carbonate under ice cooling. After extraction with ethyl acetate, the organic layer was washed with saturated brine and dried over anhydrous sodium sulfate. The solvent was evaporated under reduced pressure, and the residues were purified by silica gel column chromatography (20% ethyl acetate/hexane) to obtain the title compound (304 mg) as a yellow oil.

¹H-NMR (CDCl₃) δ: 12.19 (1H, s), 7.86-7.81 (2H, m), 7.53 (1H, d, J=8.1 Hz), 7.14 (1H, ddd, J=9.7, 8.1, 1.9 Hz), 6.96-6.91 (2H, m), 6.74 (1H, ddd, J=8.4, 7.2, 1.3 Hz), 4.76 (1H, t, J=7.4 Hz), 3.89 (3H, s), 3.62 (3H, s), 3.04-2.54 (7H, m), 2.43-2.22 (4H, m), 2.10-1.98 (1H, m), 1.61-1.51 (4H, m).

Compounds of Reference Examples 83 and 84, which have been produced by using the compound of Reference Examples 72 and 74 according to the same method as Reference Example 82, are shown in Table 9.

TABLE 9

| Reference Example | Structural formula | ¹H-NMR |
|---|---|---|
| 83 | | (CDCl₃) δ: 11.47 (1H, s), 7.73-7.64 (3H, m), 7.16-7.10 (1H, m), 6.93-6.90 (2H, m), 6.73 (1H, ddd, J = 8.6, 7.3, 1.3 Hz), 4.32-4.27 (1H, m), 3.88 (3H, s), 3.63 (3H, s), 2.96-2.62 (7H, m), 2.51-2.42 (1H, m), 2.27 (2H, t, J = 7.1 Hz), 2.16-2.09 (1H, m), 2.01-1.96 (1H, m), 1.76-1.54 (6H, m). |
| 84 | | (CDCl₃) δ: 11.25 (1H, s), 7.86 (1H, d, J = 8.1 Hz), 7.79 (1H, d, J = 1.8 Hz), 7.30-7.25 (1H, m), 7.14-7.08 (1H, m), 6.97-6.96 (1H, m), 6.85 (1H, d, J = 8.1 Hz), 6.77-6.72 (1H, m), 4.14 (1H, t, J = 8.6 Hz), 3.90 (3H, s), 3.64 (3H, s), 3.08-2.59 (8H, m), 2.28 (2H, t, J = 6.9 Hz), 2.06-1.38 (10H, m). |

Reference Example 85

Methyl 1-{N-(4-methoxycarbonylbutyl)-N-[2-[2-[4-(2-phenylethyl)benzyloxy]phenyl]ethyl] amino}indane-5-carboxylate Reference Example 82 (298 mg) was dissolved in acetonitrile (2.8 mL), added with 4-(2-phenylethyl)benzyl chloride (194 mg) and potassium carbonate (145 mg), and stirred for 18 hours under reflux with heating. After cooling to room temperature, the solvent was evaporated under reduced pressure and the residues were suspended in water followed by extraction with ethyl acetate. The organic layer was washed with saturated brine and dried over anhydrous sodium sulfate. The solvent was evaporated under reduced pressure, and the residues were purified by silica gel column chromatography (17% ethyl acetate/hexane) to obtain the title compound (393 mg) as a yellow oil.

$^1$H-NMR (CDCl$_3$) δ: 7.81-7.78 (2H, m), 7.31-7.09 (12H, m), 6.90-6.85 (2H, m), 4.97 (1H, d, J=13.2 Hz), 4.93 (1H, d, J=13.2 Hz), 4.51 (1H, t, J=8.1 Hz), 3.88 (3H, s), 3.64 (3H, s), 2.94-2.82 (6H, m), 2.76-2.59 (4H, m), 2.42 (2H, t, J=6.9 Hz), 2.21 (2H, t, J=7.3 Hz), 2.14-2.06 (1H, m), 1.97-1.84 (1H, m), 1.65-1.39 (4H, m).

Compounds of Reference Examples 86 to 108, which have been produced by using the corresponding compound (13) and the compound of Reference Example 83 or 84 according to the same method as Reference Example 85, are shown in Table 10 to Table 13.

TABLE 10

| Reference Example | Structural formula | $^1$H-NMR |
| --- | --- | --- |
| 86 |  | (CDCl$_3$) δ: 7.72-7.64 (3H, m), 7.32-7.08 (11H, m), 6.90-6.85 (2H, m), 4.92 (2H, s), 3.98-3.93 (1H, m), 3.88 (3H, s), 3.63 (3H, s), 2.92-2.85 (5H, m), 2.76-2.58 (5H, m), 2.43 (2H, t, J = 6.9 Hz), 2.20 (2H, t, J = 7.4 Hz), 2.02-1.89 (2H, m), 1.64-1.36 (6H, m). |
| 87 |  | (CDCl$_3$) δ: 7.76-7.71 (2H, m), 7.31-7.11 (11H, m), 7.03 (1H, d, J = 6.6 Hz), 6.88-6.83 (2H, m), 4.99 (2H, s), 3.88 (3H, s), 3.82-3.80 (1H, m), 3.62 (3H, s), 3.22-3.15 (1H, m), 2.92-2.70 (9H, m), 2.60-2.42 (3H, m), 2.17 (2H, t, J = 7.1 Hz), 1.98-1.38 (9H, m). |
| 88 |  | (CDCl$_3$) δ: 7.68-7.60 (3H, m), 7.30-7.08 (11H, m), 6.91-6.81 (2H, m), 4.88 (1H, d, J = 11.5 Hz), 4.84 (1H, d, J = 11.5 Hz), 3.93-3.91 (1H, m), 3.88 (3H, s), 3.63 (3H, s), 2.98-2.82 (5H, m), 2.69-2.57 (5H, m), 2.37 (2H, t, J = 6.8 Hz), 2.16 (2H, t, J = 7.4 Hz), 1.91-1.86 (2H, m), 1.60-1.31 (6H, m). |

TABLE 10-continued

| Reference Example | Structural formula | ¹H-NMR |
|---|---|---|
| 89 | | (CDCl$_3$) δ: 7.70-7.63 (3H, m), 7.30-7.08 (11H, m), 6.90-6.84 (2H, m), 4.92 (2H, s), 3.94-3.92 (1H, m), 3.87 (3H, s), 3.63 (3H, s), 2.93-2.86 (5H, m), 2.73-2.62 (5H, m), 2.43 (2H, t, J = 7.0 Hz), 2.18 (2H, t, J = 7.4 Hz), 2.01-1.88 (2H, m), 1.63-1.36 (6H, m). |
| 90 | | (CDCl$_3$) δ: 7.72-7.63 (3H, m), 7.38-7.28 (5H, m), 7.19-7.12 (1H, m), 7.10 (1H, dd, J = 7.5, 1.3 Hz), 6.90-6.84 (2H, m), 4.95 (2H, s), 4.00-3.91 (1H, br m), 3.88 (3H, s), 3.64 (3H, s), 2.95-2.83 (1H, m), 2.79-2.55 (5H, m), 2.44 (2H, t, J = 7.0 Hz), 2.20 (2H, t, J = 7.3 Hz), 2.03-1.87 (2H, m), 1.67-1.35 (6H, m). |
| 91 | | (CDCl$_3$) δ: 7.69-7.64 (3H, m), 7.42-7.36 (2H, m), 7.28-7.20 (2H, m), 7.19-7.09 (2H, m), 6.93-6.82 (2H, m), 5.05 (2H, s), 3.98-3.93 (1H, m), 3.88 (3H, s), 3.64 (3H, s), 2.96-2.87 (1H, m), 2.79-2.62 (5H, m), 2.47 (2H, t, J = 6.9 Hz), 2.22 (2H, t, J = 7.4 Hz), 2.04-1.92 (2H, m), 1.64-1.38 (6H, m). |
| 92 | | (CDCl$_3$) δ: 7.75-7.61 (3H, m), 7.48-7.19 (6H, m), 7.18-7.12 (1H, m), 7.09 (1H, dd, J = 7.7, 1.9 Hz), 6.99-6.81 (5H, m), 5.06 (2H, s), 4.88 (2H, s), 3.98-3.86 (1H, m), 3.88 (3H, s), 3.63 (3H, s), 2.94-2.80 (1H, m), 2.79-2.56 (5H, m), 2.42 (2H, t, J = 6.8 Hz), 2.20 (2H, t, J = 7.4 Hz), 2.02-1.86 (2H, m), 1.61-1.33 (6H, m). |

TABLE 11
| 93 | 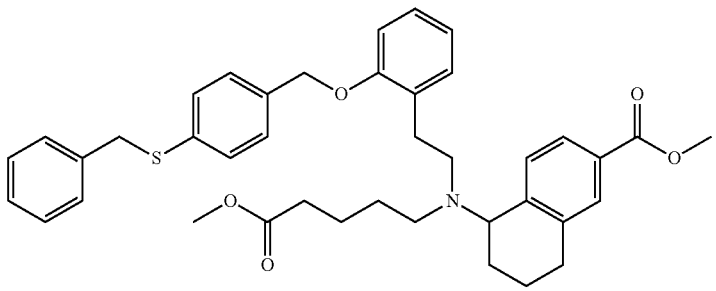 [SMILES: COC(=O)CCCCN(CCc1ccccc1OCc1ccc(CCc2ccccc2)cc1)C1CCSc2cc(C(=O)OC)ccc21] | (CDCl$_3$) δ: 7.73-7.60 (3H, m), 7.35-7.05 (11H, m), 6.87 (1H, ddd, J = 8.3, 7.5, 1.1 Hz), 6.82 (1H, d, J = 8.3 Hz), 4.89 (2H, s), 4.12 (2H, s), 3.97-3.92 (1H, m), 3.88 (3H, s), 3.64 (3H, s), 2.93-2.80 (1H, m), 2.78-2.53 (5H, m), 2.44 (2H, t, J = 7.0 Hz), 2.21 (2H, t, J = 7.3 Hz), 2.03-1.87 (2H, m), 1.67-1.34 (6H, m). |
|---|---|---|
| 94 | 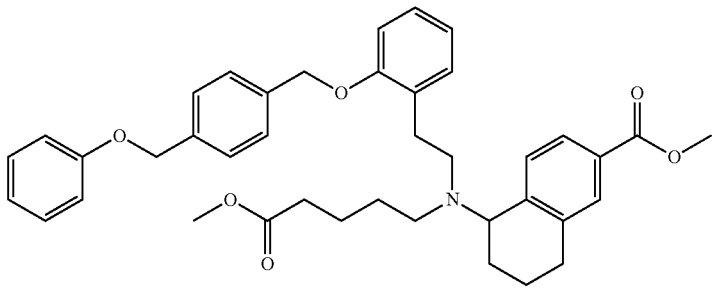 [SMILES: COC(=O)CCCCN(CCc1ccccc1OCc1ccc(CSc2ccccc2)cc1)C1CCCc2cc(C(=O)OC)ccc21] | (CDCl$_3$) δ: 7.72-7.62 (3H, m), 7.40 (2H, d, J = 8.2 Hz), 7.35-7.25 (4H, m), 7.15 (1H, ddd, J = 9.3, 7.5, 1.6 Hz), 7.10 (1H, dd, J = 7.5, 1.6 Hz), 7.01-6.82 (5H, m), 5.06 (2H, s), 4.96 (2H, s), 3.99-3.90 (1H, m), 3.87 (3H, s), 3.63 (3H, s), 2.95-2.82 (1H, m), 2.79-2.55 (5H, m), 2.44 (2H, t, J = 7.0 Hz), 2.20 (2H, t, J = 7.4 Hz), 2.03-1.87 (2H, m), 1.65-1.35 (6H, m). |
| 95 | 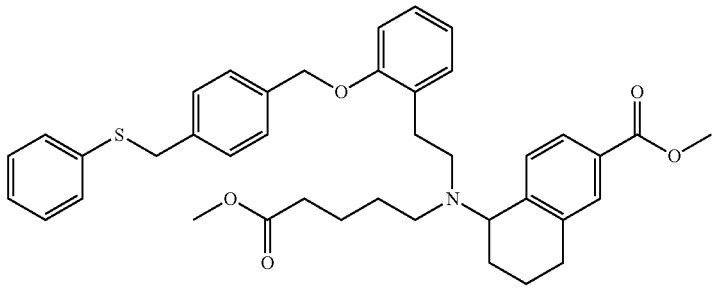 | (CDCl$_3$) δ: 7.71-7.61 (3H, m), 7.35-7.07 (11H, m), 6.91-6.80 (2H, m), 4.91 (2H, s), 4.12 (2H, s), 3.96-3.88 (1H, m), 3.88 (3H, s), 3.64 (3H, s), 2.93-2.82 (1H, m), 2.77-2.58 (5H, m), 2.43 (2H, t, J = 7.0 Hz), 2.20 (2H, t, J = 7.0 Hz), 2.03-1.87 (2H, m), 1.66-1.35 (6H, m). |
| 96 | 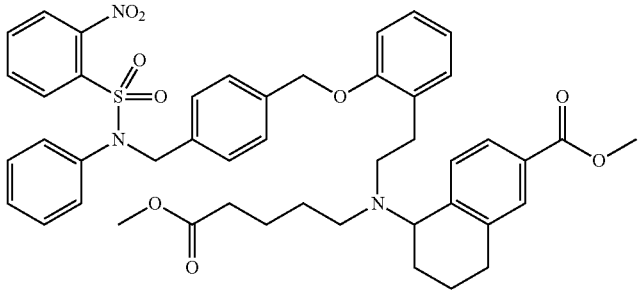 [SMILES: COC(=O)CCCCN(CCc1ccccc1OCc1ccc(CN(c2ccccc2)S(=O)(=O)c2ccccc2[N+](=O)[O-])cc1)C1CCCc2cc(C(=O)OC)ccc21] | (CDCl$_3$) δ: 7.68-7.60 (5H, m), 7.54-7.43 (2H, m), 7.26-7.07 (11H, m), 6.89-6.79 (2H, m), 4.96 (2H, s), 4.89 (2H, s), 3.97-3.90 (1H, m), 3.88 (3H, s), 3.64 (3H, s), 2.91-2.82 (1H, m), 2.70-2.59 (5H, m), 2.43 (2H, t, J = 6.9 Hz), 2.19 (2H, t, J = 7.3 Hz), 1.99-1.90 (2H, m), 1.61-1.37 (6H, m). |
| 97 | 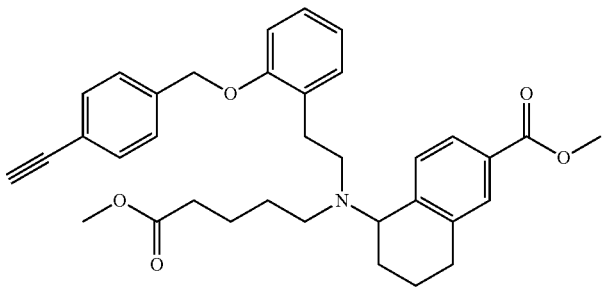 [SMILES: C#Cc1ccc(COc2ccccc2CCN(CCCCC(=O)OC)C2CCCc3cc(C(=O)OC)ccc32)cc1] | (CDCl$_3$) δ: 7.71-7.60 (3H, m), 7.45 (2H, d, J = 8.2 Hz), 7.29-7.22 (2H, m), 7.19-7.07 (2H, m), 6.88 (1H, ddd, J = 8.3, 7.3, 0.9 Hz), 6.81 (1H, d, J = 8.0 Hz), 4.94 (2H, s), 3.99-3.91 (1H, m), 3.88 (3H, s), 3.65 (3H, s), 3.08 (1H, s), 2.93-2.80 (1H, m), 2.79-2.55 (5H, m), 2.46 (2H, t, J = 6.9 Hz), 2.22 (2H, t, J = 7.3 Hz), 2.02-1.90 (2H, m), 1.69-1.36 (6H, m). |

TABLE 11-continued

| 98 | 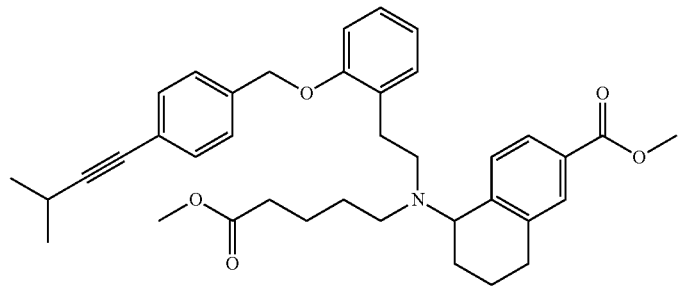 [SMILES: COC(=O)CCCCN(CCc1ccccc1OCc1ccc(C#CC(C)C)cc1)C1CCCc2cc(C(=O)OC)ccc21] | (CDCl₃) δ: 7.71-7.61 (3H, m), 7.34 (2H, d, J = 8.1 Hz), 7.20 (2H, d, J = 8.1 Hz), 7.18-7.07 (2H, m), 6.87 (1H, ddd, J = 8.0, 7.4, 0.8 Hz), 6.81 (1H, d, J = 8.0 Hz), 4.91 (2H, s), 3.98-3.90 (1H, m), 3.88 (3H, s), 3.65 (3H, s), 2.93-2.57 (7H, m), 2.45 (2H, t, J = 6.9 Hz), 2.22 (2H, t, J = 7.4 Hz), 2.02-1.90 (2H, m), 1.68-1.36 (6H, m), 1.27 (6H, d, J = 6.6 Hz). |

TABLE 12

| 99 | 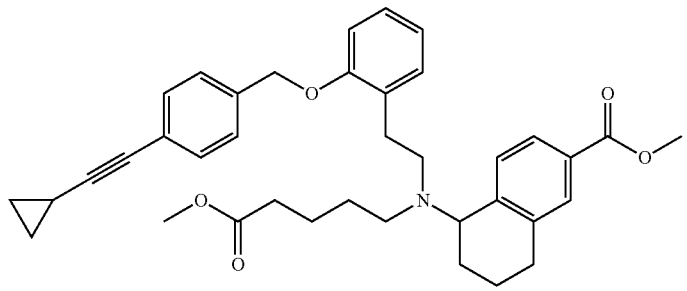 [SMILES: COC(=O)CCCCN(CCc1ccccc1OCc1ccc(C#CC2CC2)cc1)C1CCCc2cc(C(=O)OC)ccc21] | (CDCl₃) δ: 7.71-7.61 (3H, m), 7.33 (2H, d, J = 8.3 Hz), 7.19 (2H, d, J = 8.3 Hz), 7.17-7.07 (2H, m), 6.87 (1H, ddd, J = 8.3, 7.5, 0.9 Hz), 6.81 (1H, d, J = 8.3 Hz), 4.91 (2H, s), 3.98-3.90 (1H, m), 3.88 (3H, s), 3.65 (3H, s), 2.93-2.81 (1H, m), 2.78-2.54 (5H, m), 2.44 (2H, t, J = 7.0 Hz), 2.22 (2H, t, J = 7.5 Hz), 2.02-1.89 (2H, m), 1.68-1.34 (7H, m), 0.91-0.78 (4H, m). |
| 100 | 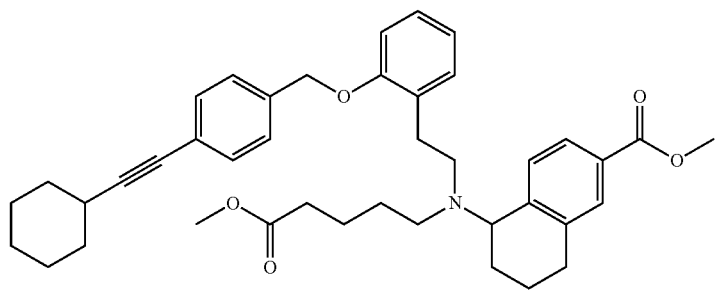 [SMILES: COC(=O)CCCCN(CCc1ccccc1OCc1ccc(C#CC2CCCCC2)cc1)C1CCCc2cc(C(=O)OC)ccc21] | (CDCl₃) δ: 7.71-7.60 (3H, m), 7.35 (2H, d, J = 8.3 Hz), 7.20 (2H, d, J = 8.3 Hz), 7.17-7.07 (2H, m), 6.87 (1H, ddd, J = 8.3, 7.5, 1.0 Hz), 6.81 (1H, dd, J = 8.3, 0.8 Hz), 4.91 (2H, s), 3.99-3.91 (1H, m), 3.88 (3H, s), 3.65 (3H, s), 2.94-2.80 (1H, m), 2.78-2.52 (5H, m), 2.44 (2H, t, J = 6.9 Hz), 2.22 (2H, t, J = 7.4 Hz), 2.02-1.83 (4H, m), 1.82-1.69 (2H, m), 1.65-1.30 (13H, m). |
| 101 | 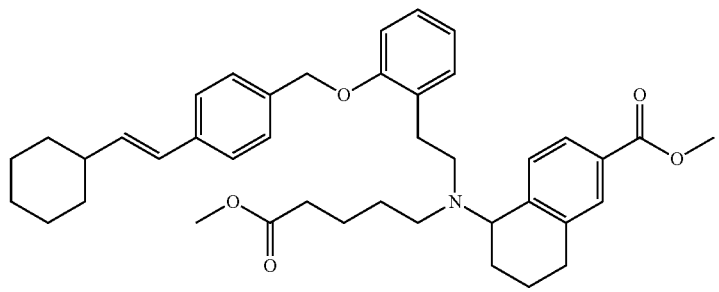 [SMILES: COC(=O)CCCCN(CCc1ccccc1OCc1ccc(/C=C/C2CCCCC2)cc1)C1CCCc2cc(C(=O)OC)ccc21] | (CDCl₃) δ: 7.72-7.63 (3H, m), 7.33-7.19 (4H, m), 7.17-7.07 (2H, m), 6.89-6.82 (2H, m), 6.33 (1H, d, J = 15.9 Hz), 6.17 (1H, dd, J = 15.9, 6.8 Hz), 4.92 (2H, s), 3.98-3.87 (1H, m), 3.88 (3H, s), 3.64 (3H, s), 2.95-2.82 (1H, m), 2.78-2.55 (5H, m), 2.43 (2H, t, J = 6.9 Hz), 2.23-2.08 (1H, m), 2.20 (2H, t, J = 7.3 Hz), 2.01-1.87 (2H, m), 1.86-1.09 (16H, m). |
| 102 | 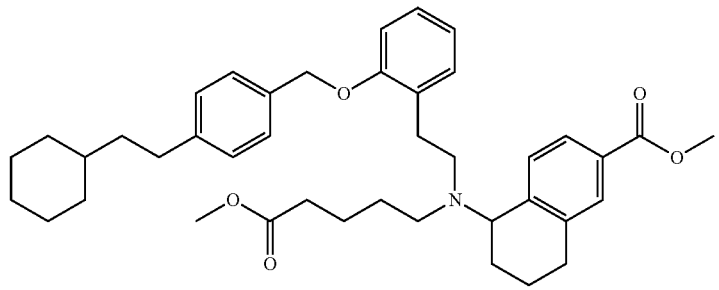 [SMILES: COC(=O)CCCCN(CCc1ccccc1OCc1ccc(CCC2CCCCC2)cc1)C1CCCc2cc(C(=O)OC)ccc21] | (CDCl₃) δ: 7.72-7.63 (3H, m), 7.28-7.07 (6H, m), 6.90-6.83 (2H, m), 4.91 (2H, s), 3.99-3.91 (1H, m), 3.88 (3H, s), 3.64 (3H, s), 2.96-2.83 (1H, m), 2.76-2.56 (7H, m), 2.42 (2H, t, J = 6.9 Hz), 2.20 (2H, t, J = 7.3 Hz), 2.02-1.86 (2H, m), 1.83-1.35 (13H, m), 1.33-1.11 (4H, m), 1.02-0.86 (2H, m). |

TABLE 12-continued
| 103 | 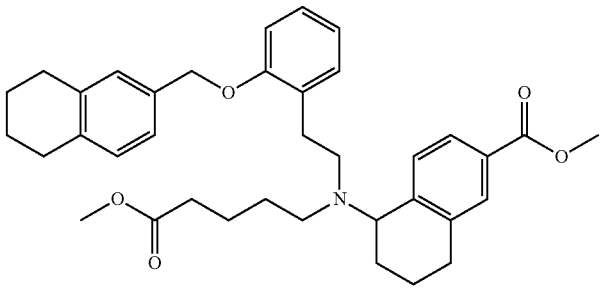 [SMILES: COC(=O)CCCCN(CCc1ccccc1OCc1ccc2c(c1)CCCC2)C1CCCc2cc(C(=O)OC)ccc21] | (CDCl₃) δ: 7.72-7.62 (3H, m), 7.18-7.12 (1H, m), 7.09 (1H, dd, J = 7.7, 1.8 Hz), 7.04-6.98 (3H, m), 6.90-6.82 (2H, m), 4.87 (2H, s), 3.99-3.91 (1H, m), 3.88 (3H, s), 3.64 (3H, s), 2.95-2.83 (1H, m), 2.79-2.59 (9H, m), 2.43 (2H, t, J = 6.9 Hz), 2.19 (2H, t, J = 7.5 Hz), 2.02-1.87 (2H, m), 1.82-1.75 (4H, m), 1.65-1.35 (6H, m). |
| --- | --- | --- |
| 104 | 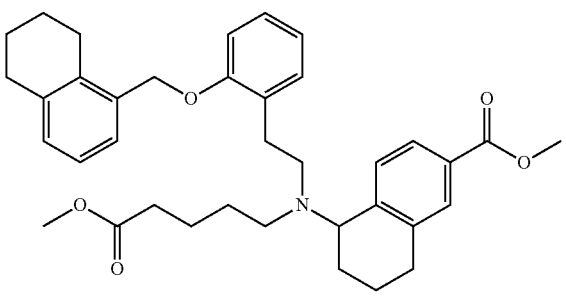 [SMILES: COC(=O)CCCCN(CCc1ccccc1OCc1cccc2c1CCCC2)C1CCCc2cc(C(=O)OC)ccc21] | (CDCl₃) δ: 7.73-7.61 (3H, m), 7.22-7.01 (5H, m), 6.93-6.83 (2H, m), 4.90 (2H, s), 3.97-3.86 (1H, m), 3.89 (3H, s), 3.64 (3H, s), 2.96-2.56 (10H, m), 2.40 (2H, t, J = 7.0 Hz), 2.18 (2H, t, J = 7.3 Hz), 2.00-1.70 (6H, m), 1.63-1.32 (6H, m). |
TABLE 13
| 105 | 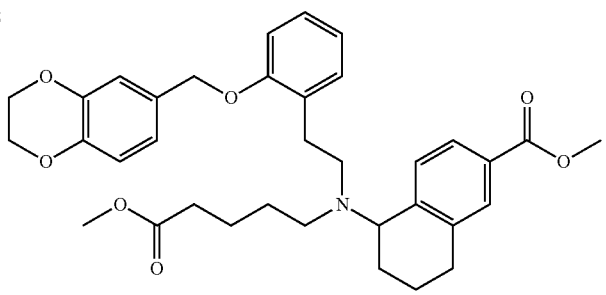 [SMILES: COC(=O)CCCCN(CCc1ccccc1OCc1ccc2c(c1)OCCO2)C1CCCc2cc(C(=O)OC)ccc21] | (CDCl₃) δ: 7.72-7.62 (3H, m), 7.15 (1H, ddd, J = 9.4, 7.7, 1.7 Hz), 7.08 (1H, dd, J = 7.2, 1.7 Hz), 6.89-6.74 (5H, m), 4.83 (2H, s), 4.25 (4H, s), 4.00-3.91 (1H, m), 3.88 (3H, s), 3.64 (3H, s), 2.93-2.81 (1H, m), 2.78-2.57 (5H, m), 2.44 (2H, t, J = 6.8 Hz), 2.21 (2H, t, J = 7.3 Hz), 2.06-1.89 (2H, m), 1.61-1.36 (6H, m). |
| --- | --- | --- |
| 106 | 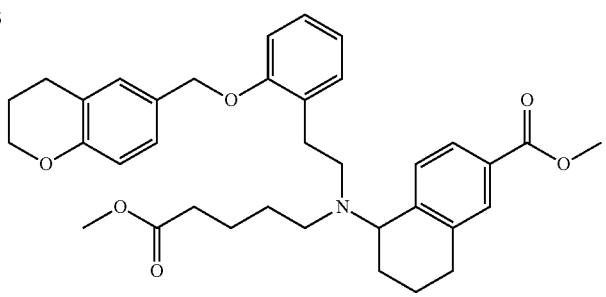 | (CDCl₃) δ: 7.73-7.61 (3H, m), 7.19-7.12 (1H, m), 7.09 (1H, dd, J = 7.8, 1.9 Hz), 7.05-6.95 (2H, m), 6.90-6.82 (2H, m), 6.75 (1H, d, J = 7.7 Hz) 4.82 (2H, s), 4.20-4.15 (2H, m), 3.98-3.91 (1H, m), 3.88 (3H, s), 3.64 (3H, s), 2.92-2.57 (8H, m), 2.42 (2H, t, J = 6.9 Hz), 2.19 (2H, t, J = 7.2 Hz), 2.05-1.88 (4H, m), 1.63-1.34 (6H, m). |
| 107 | 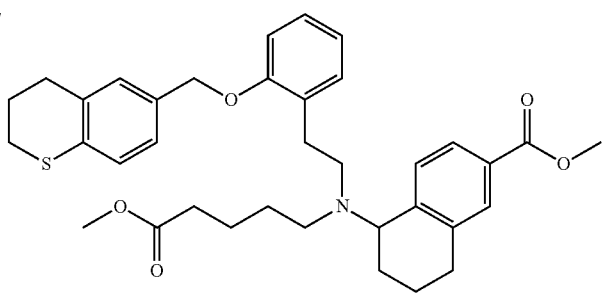 | (CDCl₃) δ: 7.72-7.61 (3H, m), 7.15 (1H, ddd, J = 9.5, 7.7, 1.7 Hz), 7.09 (1H, dd, J = 7.3, 1.7 Hz), 7.06-6.93 (3H, m), 6.90-6.81 (2H, m), 4.83 (2H, s), 3.99-3.90 (1H, m), 3.88 (3H, s), 3.64 (3H, s), 3.06-2.95 (2H, m), 2.93-2.80 (1H, m), 2.79-2.57 (7H, m), 2.43 (2H, t, J = 7.0 Hz), 2.20 (2H, t, J = 7.3 Hz), 2.15-2.05 (2H, m), 2.02-1.87 (2H, m), 1.66-1.33 (6H, m). |

TABLE 13-continued

| | | |
|---|---|---|
| 108 | 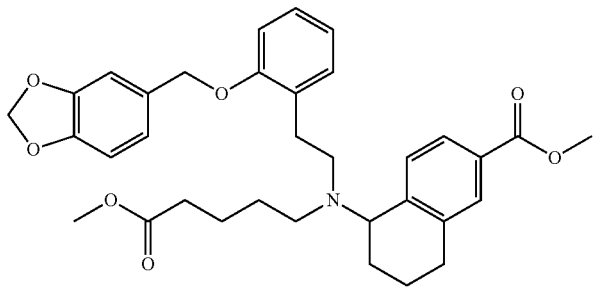 [SMILES: COC(=O)CCCCN(CCc1ccccc1OCc1ccc2c(c1)OCO2)C1CCCc2cc(C(=O)OC)ccc21] | (CDCl$_3$) δ: 7.73-7.61 (3H, m), 7.15 (1H, ddd, J = 9.4, 7.5, 1.7 Hz), 7.09 (1H, dd, J = 7.5, 1.7 Hz), 6.91-6.81 (2H, m), 6.78-6.74 (3H, m), 5.96 (2H, s), 4.84 (2H, s), 4.01-3.91 (1H, m), 3.88 (3H, s), 3.64 (3H, s), 2.93-2.80 (1H, m), 2.77-2.56 (5H, m), 2.45 (2H, t, J = 7.0 Hz), 2.21 (2H, t, J = 7.3 Hz), 2.07-1.90 (2H, m), 1.68-1.36 (6H, m). |

Reference Example 109

Methyl 5-{N-(4-methoxycarbonylbutyl)-N-[2-[2-[trans-4-((E)-2-phenylvinyl)cyclohexylmethoxy]phenyl]ethyl]amino}-5,6,7,8-tetrahydronaphthalene-2-carboxylate According to the same method as Reference Example 53, the title compound (132 mg) was obtained as a yellow oil from Reference Example 83 (175 mg) and Reference Example 28 (95.0 mg).

$^1$H-NMR (CDCl3) δ: 7.76-7.63 (3H, m), 7.39-7.23 (4H, m), 7.23-7.10 (2H, m), 7.07 (1H, dd, J=7.3, 1.6 Hz), 6.84 (1H, ddd, J=8.4, 7.3, 1.1 Hz), 6.77 (1H, dd, J=8.3, 1.1 Hz), 6.37 (1H, d, J=16.1 Hz), 6.17 (1H, dd, J=16.1, 7.0 Hz), 4.05-3.95 (1H, m), 3.89 (3H, s), 3.73-3.65 (2H, m), 3.64 (3H, s), 2.94-2.59 (6H, m), 2.51 (2H, t, J=7.0 Hz), 2.27 (2H, t, J=7.5 Hz), 2.15-1.95 (3H, m), 1.95-1.83 (3H, m), 1.76-1.38 (8H, m), 1.33-1.03 (4H, m).

Compounds of Reference Examples 110 to 115, which have been produced by using the corresponding compound (13) and the compound of Reference Example 83 according to the same method as Reference Example 109, are shown in Table 14.

TABLE 14

| Reference Example | Structural formula | $^1$H-NMR |
|---|---|---|
| 110 | | (CDCl$_3$) δ: 7.74-7.64 (3H, m), 7.32-7.23 (2H, m), 7.22-7.09 (4H, m), 7.06 (1H, dd, J = 7.5, 1.5 Hz), 6.83 (1H, ddd, J = 8.2, 7.5, 0.9 Hz), 6.76 (1H, dd, J = 8.2, 0.8 Hz), 4.03-3.95 (1H, m), 3.88 (3H, s), 3.67-3.62 (2H, m), 3.64 (3H, s), 2.93-2.58 (8H, m), 2.50 (2H, t, J = 7.0 Hz), 2.26 (2H, t, J = 7.1 Hz), 2.10-1.95 (2H, m), 1.89-1.79 (2H, m), 1.72-1.41 (12H, m), 1.08-0.92 (4H, m). |
| 111 | | (CDCl$_3$) δ: 7.73-7.61 (3H, m), 7.31-7.23 (2H, m), 7.21-7.11 (4H, m), 7.06 (1H, dd, J = 7.3, 1.8 Hz), 6.83 (1H, ddd, J = 8.5, 7.3, 1.0 Hz), 6.78 (1H, dd, J = 8.3, 1.0 Hz), 4.02-3.94 (1H, m), 3.87 (3H, s), 3.80-3.68 (2H, m), 3.65 (3H, s), 2.91-2.54 (8H, m), 2.49 (2H, t, J = 7.0 Hz), 2.26 (2H, t, J = 7.3 Hz), 2.13-1.94 (3H, br m), 1.93-1.79 (1H, br m), 1.74-1.21 (16H, m). |

TABLE 14-continued

| Reference Example | Structural formula | ¹H-NMR |
|---|---|---|
| 112 | | (CDCl₃) δ: 7.76-7.63 (3H, m), 7.20-7.12 (1H, m), 7.09 (1H, dd, J = 7.5, 1.3 Hz), 6.92-6.83 (2H, m), 6.61 (1H, s), 5.02 (1H, d, J = 11.8 Hz), 4.97 (1H, d, J = 11.8 Hz), 4.02-3.93 (1H, m), 3.89 (3H, s), 3.64 (3H, s), 2.80-2.49 (10H, m), 2.43 (2H, t, J = 6.8 Hz), 2.21 (2H, t, J = 7.2 Hz), 2.10-1.90 (2H, m), 1.89-1.71 (5H, m), 1.69-1.35 (5H, m). |
| 113 | | (CDCl₃) δ: 7.76-7.62 (4H, m), 7.19-7.01 (4H, m), 6.89-6.73 (3H, m), 4.04-3.95 (1H, m), 3.90-3.81 (2H, m), 3.89 (3H, s), 3.65 (3H, s), 2.92-2.43 (12H, m), 2.27 (2H, t, J = 7.4 Hz), 2.12-1.94 (4H, m), 1.74-1.35 (7H, m). |
| 114 | | (CDCl₃) δ: 7.68-7.59 (3H, m), 7.32-6.84 (12H, m), 5.31-5.29 (1H, m), 3.88 (3H, s), 3.85-3.83 (1H, m), 3.64, 3.62 (3H, each s), 2.90-2.48 (13H, m), 2.38-2.32 (2H, m), 2.21-2.13 (2H, m), 1.95-1.35 (11H, m). |
| 115 | | (CDCl₃) δ: 7.75-7.67 (3H, m), 7.42-7.36 (2H, m), 7.33-7.27 (3H, m), 7.18 (1H, ddd, J = 8.0, 7.5, 1.7 Hz), 7.09 (1H, dd, J = 7.5, 1.7 Hz), 6.99 (1H, d, J = 8.0 Hz), 6.89 (1H, ddd, J = 8.4, 7.5, 1.1 Hz), 4.81 (2H, s), 4.05-3.96 (1H, m), 3.88 (3H, s), 3.64 (3H, s), 2.94-2.82 (1H, m), 2.80-2.59 (5H, m), 2.50 (2H, t, J = 6.7 Hz), 2.24 (2H, t, J = 7.3 Hz), 2.11-1.90 (2H, m), 1.73-1.41 (6H, m). |

Reference Example 116

Methyl 5-{N-(4-methoxycarbonylbutyl)-N-[2-[2-[4-(2-phenylaminomethyl)benzyloxy]phenyl]ethyl]amino}-5,6,7,8-tetrahydronaphthalene-2-carboxylate According to the same method as Reference Example 62, the title compound was obtained as a yellow oil from Reference Example 96 (172 mg).

$^1$H-NMR (CDCl3) δ: 7.69-7.60 (3H, m), 7.35-7.08 (8H, m), 6.89-6.84 (2H, m), 6.74-6.64 (3H, m), 4.94 (2H, s), 4.33 (2H, s), 3.97-3.91 (1H, m), 3.87 (3H, s), 3.64 (3H, s), 2.90-2.60 (6H, m), 2.44 (2H, t, J=7.0 Hz), 2.19 (2H, t, J=7.3 Hz), 2.00-1.91 (2H, m), 1.63-1.38 (7H, m).

Reference Example 117

Methyl 5-{N-[4-(1H-tetrazol-5-yl)butyl]-N-[2-[2-[4-(2-phenylethyl)benzyloxy]phenyl]ethyl]amino}-5,6,7,8-tetrahydronaphthalene-2-carboxylate Reference Example 81 (102 mg) was suspended in toluene (5.0 mL), added with trimethyl tin azide (175 mg), and stirred for 44 hours under reflux with heating. After cooling to room temperature, the solvent was evaporated under reduced pressure. The residues were dissolved in methanol (2 mL) and stirred for 15 minutes at room temperature. Subsequently, the solvent was evaporated under reduced pressure, and the residues were purified by silica gel column chromatography (2% methanol/chloroform) to obtain the title compound (84 mg) as yellow amorphous.

$^1$H-NMR (CDCl3) δ: 7.70-7.69 (3H, m), 7.30-7.06 (11H, m), 6.91-6.83 (2H, m), 4.92 (2H, s), 4.26 (1H, dd, J=8.8, 5.9 Hz), 4.11 (1H, s), 3.87 (3H, s), 2.98-2.69 (12H, m), 2.54 (2H, t, J=6.1 Hz), 2.02-1.84 (2H, m), 1.75-1.48 (6H, m).

Reference Example 118

8-Oxo-5,6,7,8-tetrahydroisoquinoline-3-yl trifluoromethanesulfonate

According to the same method as Reference Example 10, the title compound (1.53 g) was obtained as a yellow oil from 5,6,7,8-tetrahydroisoquinoline-3,8-dione (970 mg).

$^1$H-NMR (CDCl3) δ: 8.96 (1H, s), 7.07 (1H, s), 3.05 (2H, t, J=6.1 Hz), 2.76-2.70 (2H, m), 2.26-2.16 (2H, m).

Reference Example 119

3-Cyano-8-oxo-5,6,7,8-tetrahydroisoquinoline

Reference Example 118 (1.53 g) was dissolved in DMF (12 mL), added with zinc cyanide (487 mg) and tetrakis(triphenylphosphine)palladium (0) (299 mg) under argon atmosphere, and stirred for 3 hours at 80° C. After filtration through Celite, it was diluted with ethyl acetate and washed with saturated brine. After drying over anhydrous sodium sulfate, the solvent was evaporated under reduced pressure and the residues were purified by silica gel column chromatography (8 to 16% ethyl acetate/hexane), suspended in a mixture solvent of hexane/diisopropyl ether, and collected by filtration to obtain the title compound (680 mg) as a white powder.

$^1$H-NMR (CDCl$_3$) δ: 9.20 (1H, s), 7.64-7.62 (1H, m), 3.03 (2H, t, J=6.0 Hz), 2.79-2.72 (2H, m), 2.28-2.18 (2H, m).

Reference Example 120

8-Oxo-5,6,7,8-tetrahydroisoquinoline-3-carboxylic acid

According to the same method as Reference Example 8, the title compound (685 mg) was obtained as a white powder from Reference Example 119 (672 mg).

$^1$H-NMR (CDCl$_3$) δ: 9.14 (1H, s), 8.15 (1H, s), 3.10 (2H, t, J=6.0 Hz), 2.81-2.73 (2H, m), 2.29-2.19 (2H, m).

Reference Example 121

Methyl 8-oxo-5,6,7,8-tetrahydroisoquinoline-3-carboxylate

Reference Example 120 (540 mg) was dissolved in chloroform (14 mL), and added under ice cooling with a diethyl ether solution of diazomethane until the completion of the reaction. Acetic acid was added until the reaction solution becomes colorless, and the solvent was evaporated under reduced pressure. The residues were purified by silica gel column chromatography (8 to 80% ethyl acetate/hexane) to obtain the title compound (360 mg) as a white powder.

$^1$H-NMR (CDCl$_3$) δ: 9.24 (1H, s), 8.06-8.04 (1H, m), 4.03 (3H, s), 3.05 (2H, t, J=6.1 Hz), 2.78-2.70 (2H, m), 2.27-2.16 (2H, m).

Reference Example 122

Methyl 8-hydroxy-5,6,7,8-tetrahydroisoquinoline-3-carboxylate

According to the same method as Reference Example 11, the title compound (448 mg) was quantitatively obtained from Reference Example 121 (432 mg).

$^1$H-NMR (CDCl$_3$) δ: 8.78 (1H, s), 7.88 (1H, s), 4.96-4.86 (1H, m), 4.00 (3H, s), 2.96-2.70 (2H, m), 2.15-1.76 (5H, m).

Compounds of Reference Examples 123 and 124, which have been produced by using the corresponding compound (4) and the compound of Reference Example 51 according to the same method as Reference Example 53, are shown in Table 15.

TABLE 15

| Reference Example | Structural formula | ¹H-NMR |
|---|---|---|
| 123 | | (CDCl₃) δ: 8.23-8.20 (1H, m), 7.80-7.65 (3H, m), 7.47-7.43 (2H, m), 7.20 (1H, dd, J = 8.6, 1.1 Hz), 7.13 (1H, ddd, J = 9.3, 8.3, 1.7 Hz), 7.04-6.95 (2H, m), 6.87 (1H, ddd, J = 8.3, 7.3, 1.1 Hz), 5.43 (1H, dd, J = 10.8, 6.0 Hz), 5.08 (1H, d, J = 6.8 Hz), 5.02 (1H, d, J = 6.8 Hz), 4.44 (1H, dt, J = 11.5, 3.7 Hz), 4.27 (1H, td, J = 11.5, 2.1 Hz), 3.87 (3H, s), 3.57-3.43 (1H, m), 3.28 (3H, s), 3.21-3.08 (1H, m), 2.90-2.72 (2H, m), 2.55-2.26 (2H, m). |
| 124 | | (CDCl3) δ: 8.45 (1H, s), 8.21-8.15 (1H, m), 7.86 (1H, s), 7.77-7.64 (3H, m), 7.18-7.09 (1H, m), 7.04 (1H, dd, J = 7.4, 1.6 Hz), 6.96 (1H, d, J = 8.2 Hz), 6.88 (1H, ddd, J = 8.2, 7.4, 1.1 Hz), 5.36 (1H, dd, J = 10.1, 5.9 Hz), 5.04 (1H, d, J = 6.8 Hz), 5.02 (1H, d, J = 6.8 Hz), 3.96 (3H, s), 3.58-3.41 (1H, m), 3.31 (3H, s), 3.27-3.13 (1H, m), 3.00-2.76 (4H, m), 2.42-2.28 (1H, m), 2.20-1.83 (3H, m). |

Compounds of Reference Examples 125 and 126, which have been produced by using the compound of Reference Examples 123 and 124 according to the same method as Reference Example 62, are shown in Table 16.

TABLE 16

| Reference Example | Structural formula | ¹H-NMR |
|---|---|---|
| 125 | | (CDCl₃) δ: 7.53-7.44 (2H, m), 7.23-7.16 (3H, m), 7.08 (1H, dd, J = 8.7, 1.2 Hz), 6.95 (1H, ddd, J = 8.6, 7.4, 1.2 Hz), 5.19 (2H, s), 4.34-4.16 (2H, m), 3.88 (3H, s), 3.83 (1H, t, J = 4.6 Hz), 3.44 (3H, s), 3.02-2.84 (4H, m), 2.10-1.90 (2H, m). |
| 126 | | (CDCl₃) δ: 8.63 (1H, s), 7.84 (1H, s), 7.21-7.13 (2H, m), 7.09-7.04 (1H, m), 6.97-6.90 (1H, m), 5.20 (1H, d, J = 6.8 Hz), 5.18 (1H, d, J = 6.8 Hz), 3.98 (3H, s), 3.88 (1H, t, J = 4.9 Hz), 3.45 (3H, s), 3.05-2.67 (6H, m), 2.05-1.81 (3H, m), 1.81-1.69 (1H, m). |

Compounds of Reference Examples 127 and 128, which have been produced by using the compound of Reference Examples 125 and 126 according to the same method as Reference Example 71, are shown in Table 17.

TABLE 17

| Reference Example | Structural formula | ¹H-NMR |
|---|---|---|
| 127 | | (CDCl$_3$) δ: 7.56 (1H, d, J = 8.2 Hz), 7.49 (1H, dd, J = 8.2, 1.6 Hz), 7.40 (1H, d, J = 1.6 Hz), 7.18-6.97 (3H, m), 6.90 (1H, ddd, J = 8.5, 7.3, 1.2 Hz), 5.04 (2H, s), 4.38 (1H, td, J = 7.4, 3.7 Hz), 4.20-4.05 (2H, m), 3.89 (3H, s), 3.67 (3H, s), 3.34 (3H, s), 2.90-2.48 (6H, m), 2.30 (2H, t, J = 7.3 Hz), 2.07-1.92 (2H, m), 1.76-1.44 (4H, m). |
| 128 | | (CDCl$_3$) δ: 9.03 (1H, s), 7.80 (1H, s), 7.17-7.05 (2H, m), 7.01 (1H, dd, J = 8.2, 1.2 Hz), 6.89 (1H, ddd, J = 8.6, 7.4, 1.2 Hz), 5.09 (2H, s), 4.12-4.02 (1H, m), 4.00 (3H, s), 3.65 (3H, s), 3.38 (3H, s), 2.92-2.44 (8H, m), 2.28 (2H, t, J = 7.2 Hz), 2.16-1.98 (2H, m), 1.79-1.42 (6H, m). |

Compounds of Reference Examples 129 and 130, which have been produced by using the compound of Reference Examples 127 and 128 according to the same method as Reference Example 82, are shown in Table 18.

TABLE 18

| Reference Example | Structural formula | ¹H-NMR |
|---|---|---|
| 129 | | (CDCl$_3$) δ: 11.03 (1H, s), 7.55 (1H, d, J = 7.8 Hz), 7.49-7.43 (2H, m), 7.14 (1H, ddd, J = 9.6, 8.0, 1.7 Hz), 6.96-6.89 (2H, m), 6.75 (1H, ddd, J = 8.0, 7.6, 1.7 Hz), 4.38-4.30 (2H, m), 4.13-4.02 (1H, m), 3.88 (3H, s), 3.63 (3H, s), 2.96-2.63 (5H, m), 2.53-2.40 (1H, m), 2.27 (2H, t, J = 6.9 Hz), 2.17-2.03 (2H, m), 1.68-1.50 (4H, m). |
| 130 | | (CDCl$_3$) δ: 10.17 (1H, br s), 8.91 (1H, s), 7.84 (1H, s), 7.14-7.06 (1H, m), 6.95 (1H, dd, J = 7.5, 1.5 Hz), 6.86 (1H, dd, J = 8.0, 1.3 Hz), 6.75 (1H, ddd, J = 8.7, 7.5, 1.3 Hz), 4.30-4.22 (1H, m), 3.99 (3H, s), 3.63 (3H, s), 2.93-2.85 (2H, m), 2.84-2.75 (4H, m), 2.61-2.50 (2H, m), 2.26 (2H, t, J = 7.0 Hz), 2.22-2.07 (1H, m), 2.07-1.94 (1H, m), 1.82-1.66 (2H, m), 1.65-1.45 (4H, m). |

Compounds of Reference Examples 131 to 139, which have been produced by using the corresponding compound (13) and the compound of Reference Example 82, Reference Example 83, Reference Example 129 or 130 according to the same method as Reference Example 85, are shown in Table 19 to Table 20.

TABLE 19

| Reference Example | Structural formula | ¹H-NMR |
|---|---|---|
| 131 | | (CDCl$_3$) δ: 8.94 (1H, s), 7.76 (1H, s), 7.32-7.24 (2H, m), 7.24-7.08 (9H, m), 6.90-6.83 (2H, m), 4.97 (2H, s), 4.06-3.99 (1H, m), 3.98 (3H, s), 3.62 (3H, s), 2.93-2.84 (1H, m), 2.91 (4H, s), 2.79-2.65 (5H, m), 2.46-2.31 (2H, m), 2.19 (2H, t, J = 7.2 Hz), 2.07-1.88 (2H, m), 1.63-1.31 (6H, m). |
| 132 | | (CDCl$_3$) δ: 7.73-7.60 (3H, m), 7.36 (2H, d, J = 8.3 Hz), 7.28-7.08 (4H, m), 6.92-6.80 (2H, m), 4.93 (2H, s), 4.00-3.93 (1H, m), 3.88 (3H, s), 3.64 (3H, s), 2.97-2.82 (1H, m), 2.76-2.60 (5H, m), 2.42 (2H, t, J = 6.8 Hz), 2.20 (2H, t, J = 7.3 Hz), 2.03-1.89 (2H, m), 1.65-1.38 (6H, m), 1.32 (9H, s). |
| 133 | | (CDCl$_3$) δ: 7.68-7.63 (3H, m), 7.37-7.25 (3H, m), 7.19-7.08 (3H, m), 6.89-6.86 (2H, m), 4.98 (1H, d, J = 11.5 Hz), 4.93 (1H, d, J = 11.5 Hz), 3.97-3.94 (1H, m), 3.88 (3H, s), 3.63 (3H, s), 2.93-2.89 (1H, m), 2.68-2.65 (5H, m), 2.42 (2H, t, J = 6.8 Hz), 2.18 (2H, t, J = 7.3 Hz), 1.98-1.90 (2H, m), 1.58-1.37 (6H, m), 1.31 (9H, s). |
| 134 | | (CDCl$_3$) δ: 7.71-7.64 (3H, m), 7.20-7.01 (6H, m), 6.89-6.84 (2H, m), 4.90 (2H, s), 3.95-3.92 (1H, m), 3.88 (3H, s), 3.64 (3H, s), 2.90-2.85 (1H, m), 2.72-2.57 (5H, m), 2.42 (2H, t, J = 6.9 Hz), 2.20 (2H, t, J = 7.4 Hz), 2.00-1.84 (3H, m), 1.59-1.38 (6H, m), 0.99-0.93 (2H, m), 0.71-0.65 (2H, m). |
| 135 | | (CDCl$_3$) δ: 7.70-7.66 (3H, m), 7.19-7.12 (6H, m), 6.88-6.86 (2H, m), 4.92 (2H, s), 3.98-3.94 (1H, m), 3.89 (3H, s), 3.65 (3H, s), 2.93-2.87 (2H, m), 2.76-2.61 (5H, m), 2.42 (2H, t, J = 6.9 Hz), 2.20 (2H, t, J = 7.3 Hz), 1.99-1.91 (2H, m), 1.61-1.40 (6H, m), 1.25 (6H, d, J = 7.0 Hz). |

TABLE 19-continued

| Reference Example | Structural formula | $^1$H-NMR |
|---|---|---|
| 136 | | (CDCl3) δ: 7.72-7.62 (3H, m), 7.20-7.05 (5H, m), 6.90-6.83 (2H, m), 4.91 (2H, s), 4.00-3.91 (1H, m), 3.88 (3H, s), 3.64 (3H, s), 2.95-2.82 (5H, m), 2.76-2.60 (5H, m), 2.42 (2H, t, J = 7.0 Hz), 2.19 (2H, t, J = 7.4 Hz), 2.13-1.87 (4H, m), 1.64-1.34 (6H, m). |

TABLE 20

| | | |
|---|---|---|
| 137 | | (CDCl$_3$) δ: 7.84-7.74 (2H, m), 7.28-6.82 (8H, m), 4.92 (1H, d, J = 11.5 Hz), 4.87 (1H, d, J = 11.5 Hz), 4.51 (1H, t, J = 8.1 Hz), 3.89 (3H, s), 3.64 (3H, s), 2.97-2.56 (9H, m), 2.49-2.36 (3H, m), 2.24-2.14 (2H, m), 2.14-1.68 (8H, m), 1.62-1.37 (2H, m). |
| 138 | | (CDCl$_3$) δ: 7.50-7.33 (3H, m), 7.28-6.92 (5H, m), 6.90-6.84 (2H, m), 4.87 (2H, s), 4.30-4.20 (1H, m), 4.06 (1H, t, J = 7.9 Hz), 3.96-3.82 (1H, m), 3.87 (3H, s), 3.64 (3H, s), 2.96-2.60 (9H, m), 2.46-2.31 (2H, m), 2.19 (2H, t, J = 7.3 Hz), 1.95-1.70 (7H, m), 1.62-1.32 (2H, m) |
| 139 | | (CDCl$_3$) δ: 7.49-7.32 (9H, m), 7.30-7.07 (3H, m), 6.97-6.84 (4H, m), 5.06 (2H, s), 4.88 (2H, s), 4.26 (1H, td, J = 7.5, 3.7 Hz), 4.05 (1H, t, J = 7.9 Hz), 3.98-3.84 (1H, m), 3.87 (3H, s), 3.64 (3H, s), 2.92-2.80 (1H, m), 2.76-2.53 (3H, m), 2.48-2.32 (2H, m), 2.20 (2H, t, J = 7.3 Hz), 1.94-1.84 (2H, m), 1.63-1.33 (4H, m). |

Compounds of Reference Examples 140 and 141, which have been produced by using the corresponding compound (13) and the compound of Reference Example 83 according to the same method as Reference Example 109, are shown in Table 21.

TABLE 21

| Reference Example | Structural formula | ¹H-NMR |
|---|---|---|
| 140 | | (CDCl$_3$) δ: 7.82-7.68 (3H, m), 7.35-7.12 (4H, m), 7.08-6.96 (2H, m), 6.81-7.73 (1H, m), 6.65 (1H, dd, J = 7.3, 5.7 Hz), 5.26-5.13 (1H, m), 4.07-3.97 (1H, m), 3.89, 3.88 (3H, each s), 3.65 (3H, s), 3.00-2.85 (1H, m), 2.80-2.48 (7H, m), 2.31-2.24 (2H, m), 2.12-1.95 (2H, m), 1.74-1.44 (9H, m), 1.30, 1.28 (9H, each s). |
| 141 | | (CDCl$_3$) δ: 7.82-7.68 (3H, m), 7.35-7.12 (4H, m), 7.08-6.96 (2H, m), 6.81-6.74 (1H, m), 6.65 (1H, dd, J = 7.3, 5.5 Hz), 5.26-5.13 (1H, m), 4.07-3.97 (1H, m), 3.89, 3.88 (3H, each s), 3.65 (3H, s), 3.00-2.85 (1H, m), 2.80-2.48 (7H, m), 2.31-2.24 (2H, m), 2.12-1.95 (2H, m), 1.74-1.44 (9H, m), 1.30, 1.28 (9H, each s). |

Example 1

1-{N-(4-Carboxybutyl)-N-[2-[2-[4-(2-phenylethyl)benzyloxy]phenyl]ethyl]amino}indane-5-carboxylic acid Reference Example 85 (391 mg) was dissolved in THF (1.0 mL) and methanol (2.1 mL), added with 2.5 mol/L aqueous solution of sodium hydroxide (1.0 mL), and stirred for 1.5 hours at 50° C. After cooling to room temperature, the solvent was evaporated under reduced pressure. The residues were dissolved again in water. The pH was adjusted to 4 with 2 mol/L hydrochloric acid, and it was extracted with chloroform and dried over anhydrous sodium sulfate. The solvent was evaporated under reduced pressure, and the residues were purified by silica gel column chromatography (10% to 20% methanol/chloroform) to obtain the title compound as colorless amorphous.

¹H-NMR (CD$_3$OD) δ: 7.92-7.87 (2H, m), 7.50 (1H, d, J=7.9 Hz), 7.30-7.09 (11H, m), 7.03 (1H, d, J=7.5 Hz), 6.90 (1H, ddd, J=8.2, 7.3, 0.7 Hz), 5.11 (1H, dd, J=8.2, 4.9 Hz), 4.99 (2H, s), 3.19-2.82 (12H, m), 2.41-2.14 (4H, m), 1.78-1.46 (4H, m).

ESI-MS Found: m/z 592 (M+H)$^+$

Compounds of Examples 2 to 49, which have been produced by using the corresponding compound of Reference example according to the same method as Example 1, are shown in Table 22 to Table 32.

TABLE 22

| Example | Structural formula | ¹H-NMR | ESI-MS (M + H)$^+$ |
|---|---|---|---|
| 2 | | (CD$_3$OD) δ: 7.78-7.75 (2H, m), 7.52-7.49 (1H, m), 7.26-7.10 (11H, m), 6.99 (1H, d, J = 7.5 Hz), 6.88 (1H, ddd, J = 8.2, 7.5, 0.9 Hz), 4.97 (1H, d, J = 11.5 Hz), 4.92 (1H, d, J = 11.5 Hz), 4.67-4.59 (1H, m), 3.06-2.73 (13H, m), 2.23 (2H, t, J = 6.9 Hz), 2.13-2.05 (1H, m), 1.93-1.50 (6H, m). | 606 |

TABLE 22-continued

| Example | Structural formula | $^1$H-NMR | ESI-MS (M + H)$^+$ |
|---|---|---|---|
| 3 | | (CD$_3$OD) δ: 7.78-7.73 (2H, m), 7.32-7.28 (3H, m), 7.23-7.06 (9H, m), 7.00 (1H, d, J = 7.5 Hz), 6.86 (1H, ddd, J = 8.2, 7.5, 0.9 Hz), 4.98 (2H, s), 4.22 (1H, d, J = 6.6 Hz), 3.13-2.63 (12H, m), 2.16 (2H, t, J = 7.1 Hz), 1.92-1.40 (10H, m). | 620 |
| 4 | | (DMSO-D$_6$) δ: 7.43 (1H, d, J = 8.1 Hz), 7.34 (1H, dd, J = 8.1, 1.6 Hz), 7.29-7.07 (12H, m), 6.98 (1H, dd, J = 8.2, 1.2 Hz), 6.84 (1H, ddd, J = 8.2, 7.5, 1.2 Hz), 5.00 (1H, d, J = 11.9 Hz), 4.95 (1H, d, J = 11.9 Hz), 4.30-4.21 (1H, m), 4.11-3.98 (2H, m), 3.05-2.57 (10H, m), 2.13 (2H, t, J = 7.1 Hz), 2.00-1.80 (2H, m), 1.57-1.36 (4H, m). | 608 |
| 5 | | (DMSO-D$_6$) δ: 7.58 (2H, d, J = 8.6 Hz), 7.48 (1H, dd, J = 8.0, 1.8 Hz), 1.29-1.01 (11H, m), 6.98 (1H, dd, J = 8.2, 1.2 Hz), 6.84 (1H, ddd, J = 8.5, 7.4, 1.2 Hz), 4.98 (2H, s), 3.99-3.88 (1H, m), 3.10-2.93 (2H, m), 2.90 (4H, s), 2.83-2.63 (4H, m), 2.58-2.42 (2H, m), 2.28-2.08 (3H, m), 2.01-1.85 (1H, m), 1.58-1.35 (4H, m). | 624 |
| 6 | | (DMSO-D$_6$) δ: 7.89 (1H, d, J = 8.1 Hz), 7.72 (1H, d, J = 8.1 Hz), 7.30-7.03 (11H, m), 6.97 (1H, d, J = 8.1 Hz), 6.83 (1H, t, J = 7.3 Hz), 4.97 (1H, d, J = 11.9 Hz), 4.92 (1H, d, J = 11.9 Hz), 4.01-3.88 (1H, m), 2.89 (4H, s), 2.86-2.56 (6H, m), 2.48-2.37 (2H, m), 2.11 (2H, t, J = 6.9 Hz), 1.99-1.81 (2H, m), 1.65-1.31 (6H, m). | 607 |

TABLE 23
| | | | |
|---|---|---|---|
| 7 | 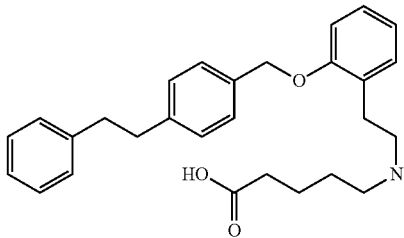 | (CD₃OD) δ: 7.52 (1H, dd, J = 7.7, 1.5Hz), 7.34-7.11 (12H, m), 7.08 (1H, dd, J = 7.5, 1.5 Hz), 6.96 (1H, dd, J = 6.3, 1.0 Hz), 6.85 (1H, ddd, J = 8.2, 7.7, 1.0 Hz), 4.95 (2H, s), 4.81 (1H, dd, J = 8.3, 3.7 Hz), 4.48 (1H, dd, J = 10.6, 3.7 Hz), 4.33 (1H, dd, J = 10.6, 8.3 Hz), 2.89-2.69 (8H, m), 2.63-2.51 (1H, m), 2.50-2.38 (1H, m), 2.15 (2H, t, J = 6.7 Hz), 1.50-1.40 (4H, m). | 594 |
| 8 | 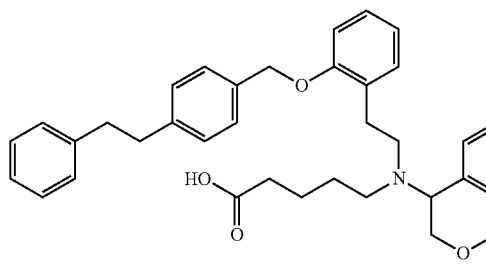 | (DMSO-D₆) δ: 7.70 (1H, d, J = 8.1 Hz), 7.60 (1H, s), 7.46 (1H, d, J = 8.1 Hz), 7.29-7.05 (11H, m), 6.96 (1H, dd, J = 8.0, 1.1 Hz), 6.83 (1H, ddd, J = 8.3, 7.3, 1.1 Hz), 4.99 (1H, d, J = 12.2 Hz), 4.94 (1H, d, J = 12.2 Hz), 4.68 (1H, d, J = 15.0 Hz), 4.57 (1H, d, J = 15.0 Hz), 3.95-3.78 (3H, m), 3.00-2.42 (10H, m), 2.10 (2H, t, J = 7.1 Hz), 1.54-1.36 (4H, m). | 608 |
| 9 | 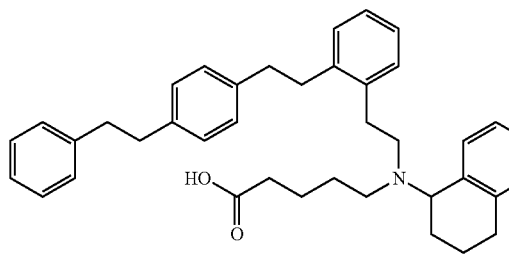 | (DMSO-D₆) δ: 7.70 (1H, d, J = 8.8 Hz), 7.62-7.57 (2H, m), 7.21-7.08 (13H, m), 4.02-3.92 (1H, m), 2.88-2.62 (12H, m), 2.46-2.39 (4H, m), 2.19 (2H, t, J = 6.7 Hz), 1.99-1.89 (2H, m), 1.57-1.49 (6H, m). | 604 |
| 10 | 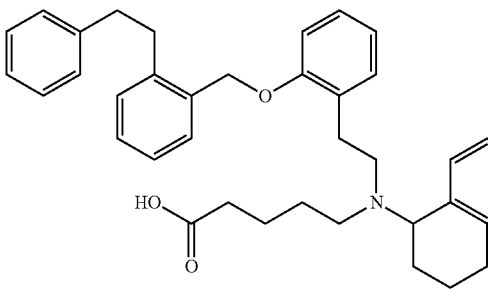 | (CD₃OD) δ: 7.68-7.65 (2H, m), 7.49 (1H, d, J = 8.4 Hz), 7.30-7.01 (11H, m), 6.93-6.85 (2H, m), 4.84 (1H, d, J = 11.0 Hz), 4.79 (1H, d, J = 11.0 Hz), 4.31-4.28 (1H, m), 2.96-2.63 (12H, m), 2.15 (2H, t, J = 6.4 Hz), 1.98-1.80 (2H, m), 1.59-1.46 (6H, m). | 606 |
| 11 | 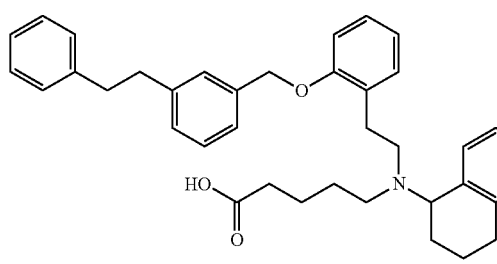 | (CD₃OD) δ: 7.73-7.71 (2H, m), 7.54-7.51 (1H, m), 7.27-7.09 (11H, m), 6.96-6.84 (2H, m), 4.93 (1H, d, J = 11.7 Hz), 4.90 (1H, d, J = 11.7 Hz), 4.52-4.47 (1H, m), 2.98-2.69 (12H, m), 2.20 (2H, t, J = 6.7 Hz), 2.09-2.00 (1H, m), 1.91-1.82 (1H, m), 1.76-1.45 (6H, m). | 606 |

TABLE 24
| | | | |
|---|---|---|---|
| 12 | 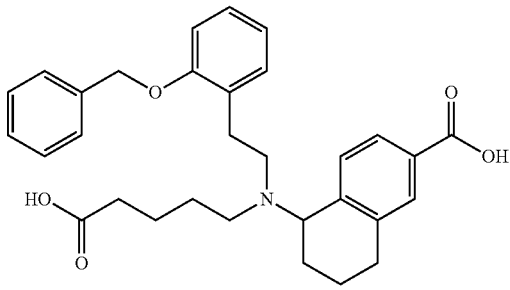 [SMILES: O=C(O)CCCCN(CCc1ccccc1OCc1ccccc1)C1CCCc2cc(C(=O)O)ccc21] | (CD₃OD) δ: 7.83-7.77 (2H, m), 7.62-7.50 (1H, m), 7.38-7.31 (5H, m), 7.22 (1H, t, J = 7.9 Hz), 7.13 (1H, d, J = 6.0 Hz), 7.00 (1H, d, J = 8.2 Hz), 6.89 (1H, t, J = 7.2 Hz), 4.99 (2H, s), 4.87-4.79 (1H, m), 3.15-2.77 (8H, m), 2.25 (2H, t, J = 7.0 Hz), 2.17-2.08 (1H, m), 1.92-1.47 (7H, m). | 502 |
| 13 | 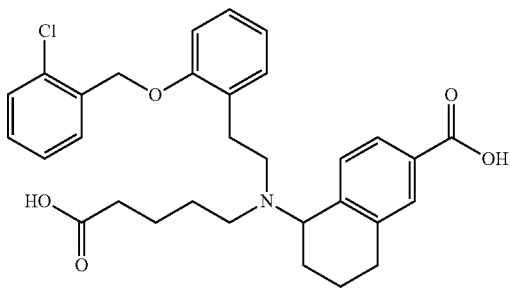 [SMILES: O=C(O)CCCCN(CCc1ccccc1OCc1ccccc1Cl)C1CCCc2cc(C(=O)O)ccc21] | (CD₃OD) δ: 7.70-7.65 (2H, m), 7.53 (1H, d, J = 8.8 Hz), 7.44-7.39 (2H, m), 7.36-7.25 (2H, m), 7.23-7.16 (1H, m), 7.11 (1H, dd, J = 7.3, 1.5 Hz), 6.95 (1H, d, J = 8.1 Hz), 6.88 (1H, ddd, J = 7.8, 7.3, 0.6 Hz), 5.06 (1H, d, J = 12.0 Hz), 5.01 (1H, d, J = 12.0 Hz), 4.42-4.33 (1H, m), 2.98-2.71 (8H, m), 2.20 (2H, t, J = 6.7 Hz), 2.09-2.00 (1H, m), 1.94-1.86 (1H, m), 1.74-1.53 (6H, m). | 536 |
| 14 | 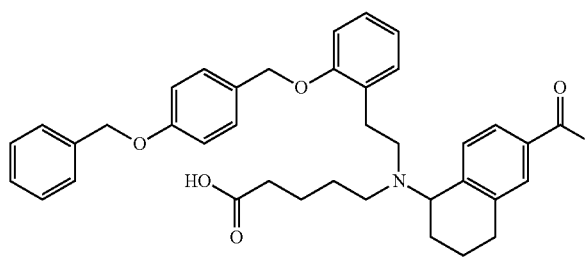 | (CDCl₃) δ: 7.82-7.70 (3H, m), 7.47-7.21 (7H, m), 7.20-7.09 (2H, m), 6.97-6.83 (4H, m), 5.05 (2H, s), 4.89 2H, s), 4.08-3.99 (1H, m), 2.97-2.84 (1H, m), 2.83-2.64 (5H, m), 2.42 (2H, t, J = 6.8 Hz), 2.22 (2H, t, J = 7.0 Hz), 2.03-1.82 (2H, m), 1.66-1.32 (6H, m). | 608 |
| 15 | 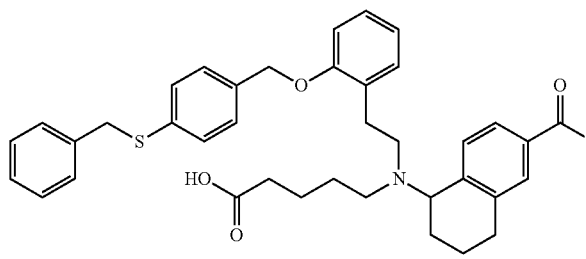 | (CD₃OD) δ: 7.74-7.67 (2H, m), 7.55-7.48 (1H, m), 7.35-7.06 (11H, m), 6.93 (1H, d, J = 7.5 Hz), 6.86 (1H, ddd, J = 8.2, 7.5, 0.9 Hz), 4.91 (1H, d, J = 11.5 Hz), 4.86 (1H, d, J = 11.5 Hz), 4.43-4.33 (1H, m), 4.14 (2H, s), 3.00-2.63 (8H, m), 2.21 (2H, t, J = 7.0 Hz), 2.08-1.95 (1H, m), 1.93-1.80 (1H, m), 1.73-1.44 (6H, m). | 624 |
| 16 | 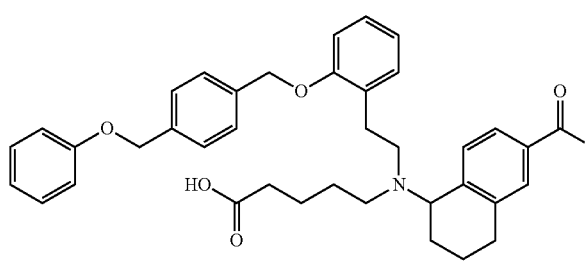 | (CD₃OD) δ: 7.73-7.68 (2H, m), 7.52 (1H, d, J = 8.6 Hz), 7.43 (2H, d, J = 8.4 Hz), 7.34 (2H, d, J = 8.4 Hz), 7.30-7.14 (3H, m), 7.10 (1H, dd, J = 7.5, 1.6 Hz), 7.01-6.94 (3H, m), 6.94-6.83 (2H, m), 5.07 (2H, s), 4.98 (1H, d, J = 11.5 Hz), 4.93 (1H, d, J = 11.5 Hz), 4.45-4.35 (1H, m), 3.02-2.63 (8H, m), 2.19 (2H, t, J = 6.6 Hz), 2.10-1.79 (2H, m), 1.75-1.41 (6H, m). | 608 |

TABLE 25

| 17 | 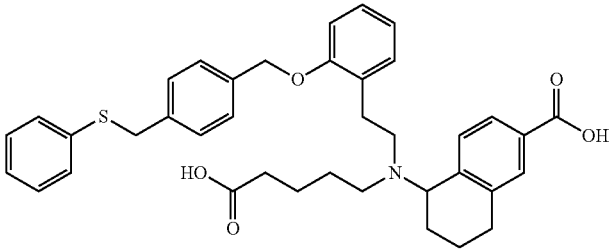 [SMILES: O=C(O)CCCCN(CCc1ccccc1OCc1ccc(CSc2ccccc2)cc1)C1CCCc2cc(C(=O)O)ccc21] | (CD$_3$OD) δ: 7.74-7.66 (2H, m), 7.51 (1H, d, J = 8.6 Hz), 7.35-7.06 (11H, m), 6.95 (1H, d, J = 7.5 Hz), 6.86 (1H, ddd, J = 8.2, 7.5, 0.9 Hz), 4.95-4.86 (2H, m), 4.48-4.40 (1H, m), 4.14 (2H, s), 3.03-2.60 (8H, m), 2.21 (2H, t, J = 6.5 Hz), 2.10-1.81 (2H, m), 1.81-1.42 (6H, m). | 624 |
| --- | --- | --- | --- |
| 18 | 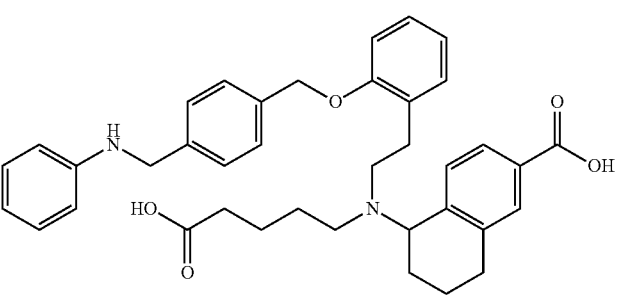 [SMILES: O=C(O)CCCCN(CCc1ccccc1OCc1ccc(CNc2ccccc2)cc1)C1CCCc2cc(C(=O)O)ccc21] | (CD$_3$OD) δ: 7.70-7.68 (2H, m), 7.50 (1H, d, J = 8.4 Hz), 7.36 (2H, d, J = 8.4 Hz), 7.27 (2H, d, J = 8.4 Hz), 7.21-7.15 (1H, m), 7.10-7.01 (3H, m), 6.96 (1H, d, J = 8.3 Hz), 6.86 (1H, ddd, J = 8.4, 7.5, 1.1 Hz), 6.63-6.54 (3H, m), 4.95 (1H, d, J = 11.4 Hz), 4.90 (1H, d, J = 11.4 Hz), 4.38-4.32 (1H, m), 4.32 (2H, s), 2.94-2.66 (8H, m), 2.19 (2H, t, J = 6.6 Hz), 2.04-1.99 (1H, m), 1.88-1.85 (1H, m), 1.66-1.52 (6H, m). | 607 |
| 19 | 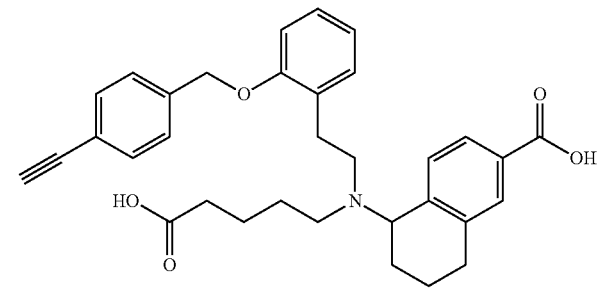 [SMILES: C#Cc1ccc(COc2ccccc2CCN(CCCCC(=O)O)C2CCCc3cc(C(=O)O)ccc32)cc1] | (CD$_3$OD) δ: 7.71-7.66 (2H, m), 7.52 (1H, d, J = 8.6 Hz), 7.43 (2H, d, J = 8.1 Hz), 7.29 (2H, d, J = 8.1 Hz), 7.21-7.14 (1H, m), 7.11 (1H, dd, J = 7.3, 1.6 Hz), 6.93 (1H, d, J = 7.8 Hz), 6.90-6.83 (1H, m), 4.97 (1H, d, J = 11.9 Hz), 4.92 (1H, d, J = 11.9 Hz), 4.40-4.32 (1H, m), 3.48 (1H, s), 2.99-2.66 (8H, m), 2.22 (2H, t, J = 6.4 Hz), 2.11-1.85 (2H, m), 1.76-1.46 (6H, m). | 526 |
| 20 | 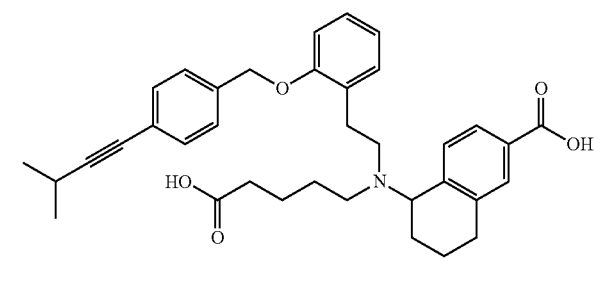 [SMILES: CC(C)C#Cc1ccc(COc2ccccc2CCN(CCCCC(=O)O)C2CCCc3cc(C(=O)O)ccc32)cc1] | (CD$_3$OD) δ: 7.62-7.57 (2H, m), 7.42 (1H, d, J = 8.8 Hz), 7.22 (2H, d, J = 8.3 Hz), 7.15 (2H, d, J = 8.3 Hz), 7.12-7.05 (1H, m), 7.01 (1H, dd, J = 7.5, 1.8 Hz), 6.85 (1H, dd, J = 8.4, 0.7 Hz), 6.77 (1H, ddd, J = 8.4, 7.5, 1.0 Hz), 4.85 (1H, d, J = 11.6 Hz), 4.80 (1H, d, J = 11.6 Hz), 4.31-4.21 (1H, m), 2.90-2.55 (9H, m), 2.13 (2H, t, J = 6.3 Hz), 2.01-1.74 (2H, m), 1.66-1.34 (6H, m), 1.16 (6H, d, J = 7.0 Hz). | 568 |

TABLE 26

| 21 | 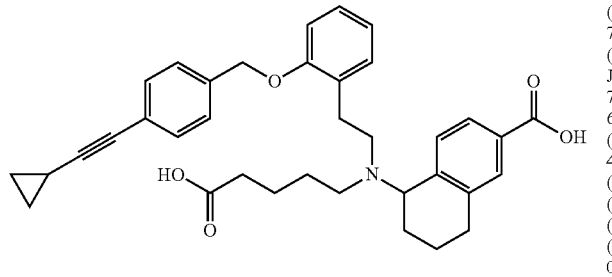 | (CD$_3$OD) δ: 7.75-7.70 (2H, m), 7.51 (1H, d, J = 8.8 Hz), 7.30 (2H, d, J = 8.3 Hz), 7.24 (2H, d, J = 8.3 Hz), 7.22-7.15 (1H, m), 7.11 (1H, dd, J = 7.6, 1.6 Hz), 6.95 (1H, d, J = 8.2 Hz), 6.88 (1H, ddd, J = 8.2, 7.6, 0.9 Hz), 4.96 (1H, d, J = 12.0 Hz), 4.91 (1H, d, J = 12.0 Hz), 4.50-4.47 (1H, m), 3.08-2.62 (8H, m), 2.24 (2H, t, J = 6.5 Hz), 2.14-1.83 (2H, m), 1.80-1.36 (7H, m), 0.94-0.66 (4H, m). | 566 |
| --- | --- | --- | --- |

TABLE 26-continued

| 22 | 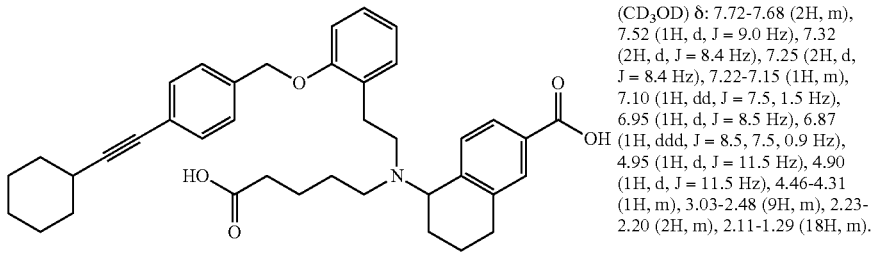 | (CD$_3$OD) δ: 7.72-7.68 (2H, m), 7.52 (1H, d, J = 9.0 Hz), 7.32 (2H, d, J = 8.4 Hz), 7.25 (2H, d, J = 8.4 Hz), 7.22-7.15 (1H, m), 7.10 (1H, dd, J = 7.5, 1.5 Hz), 6.95 (1H, d, J = 8.5 Hz), 6.87 (1H, ddd, J = 8.5, 7.5, 0.9 Hz), 4.95 (1H, d, J = 11.5 Hz), 4.90 (1H, d, J = 11.5 Hz), 4.46-4.31 (1H, m), 3.03-2.48 (9H, m), 2.23-2.20 (2H, m), 2.11-1.29 (18H, m). | 608 |
| --- | --- | --- | --- |
| 23 | 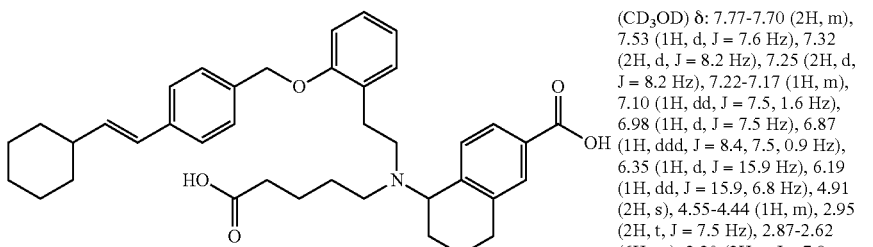 | (CD$_3$OD) δ: 7.77-7.70 (2H, m), 7.53 (1H, d, J = 7.6 Hz), 7.32 (2H, d, J = 8.2 Hz), 7.25 (2H, d, J = 8.2 Hz), 7.22-7.17 (1H, m), 7.10 (1H, dd, J = 7.5, 1.6 Hz), 6.98 (1H, d, J = 7.5 Hz), 6.87 (1H, ddd, J = 8.4, 7.5, 0.9 Hz), 6.35 (1H, d, J = 15.9 Hz), 6.19 (1H, dd, J = 15.9, 6.8 Hz), 4.91 (2H, s), 4.55-4.44 (1H, m), 2.95 (2H, t, J = 7.5 Hz), 2.87-2.62 (6H, m), 2.20 (2H, t, J = 7.8 Hz), 2.17-1.95 (2H, m), 1.94-1.09 (17H, m). | 610 |
| 24 | 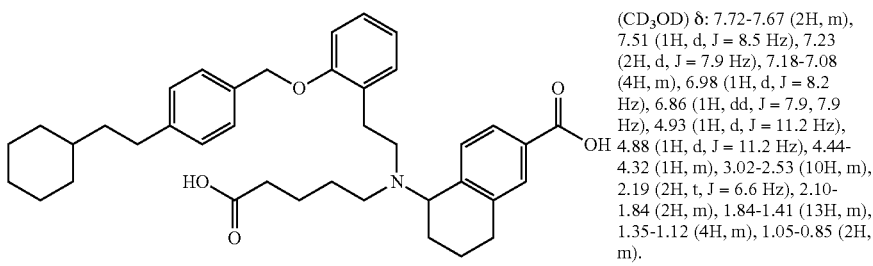 | (CD$_3$OD) δ: 7.72-7.67 (2H, m), 7.51 (1H, d, J = 8.5 Hz), 7.23 (2H, d, J = 7.9 Hz), 7.18-7.08 (4H, m), 6.98 (1H, d, J = 8.2 Hz), 6.86 (1H, dd, J = 7.9, 7.9 Hz), 4.93 (1H, d, J = 11.2 Hz), 4.88 (1H, d, J = 11.2 Hz), 4.44-4.32 (1H, m), 3.02-2.53 (10H, m), 2.19 (2H, t, J = 6.6 Hz), 2.10-1.84 (2H, m), 1.84-1.41 (13H, m), 1.35-1.12 (4H, m), 1.05-0.85 (2H, m). | 612 |

TABLE 27

| 25 | 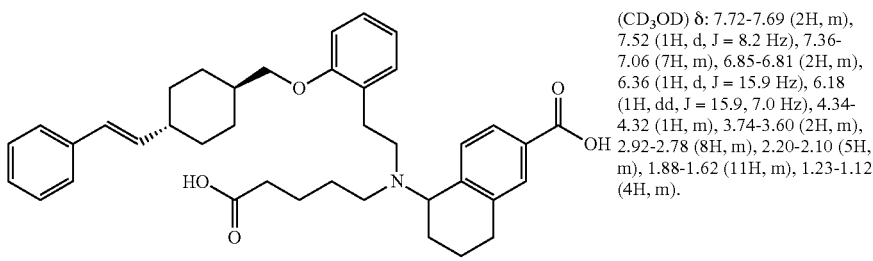 | (CD$_3$OD) δ: 7.72-7.69 (2H, m), 7.52 (1H, d, J = 8.2 Hz), 7.36-7.06 (7H, m), 6.85-6.81 (2H, m), 6.36 (1H, d, J = 15.9 Hz), 6.18 (1H, dd, J = 15.9, 7.0 Hz), 4.34-4.32 (1H, m), 3.74-3.60 (2H, m), 2.92-2.78 (8H, m), 2.20-2.10 (5H, m), 1.88-1.62 (11H, m), 1.23-1.12 (4H, m). | 610 |
| --- | --- | --- | --- |
| 26 | 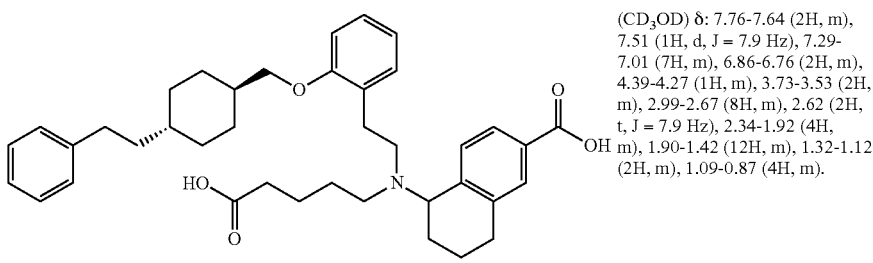 | (CD$_3$OD) δ: 7.76-7.64 (2H, m), 7.51 (1H, d, J = 7.9 Hz), 7.29-7.01 (7H, m), 6.86-6.76 (2H, m), 4.39-4.27 (1H, m), 3.73-3.53 (2H, m), 2.99-2.67 (8H, m), 2.62 (2H, t, J = 7.9 Hz), 2.34-1.92 (4H, m), 1.90-1.42 (12H, m), 1.32-1.12 (2H, m), 1.09-0.87 (4H, m). | 612 |

TABLE 27-continued

| 27 | 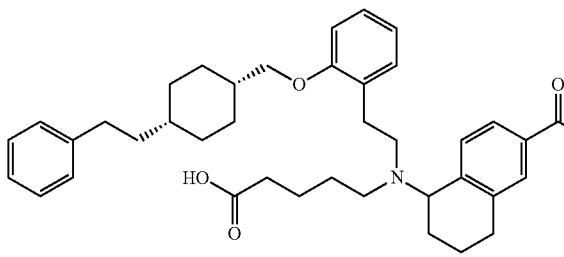 | (CD₃OD) δ: 7.69 (1H, d, J = 1.6 Hz), 7.62 (1H, dd, J = 8.0, 1.6 Hz), 7.40 (1H, d, J = 8.0 Hz), 7.29-7.04 (7H, m), 6.87-6.79 (2H, m), 4.29-4.25 (1H, m), 3.76 (1H, dd, J = 9.0, 6.6 Hz), 3.65 (1H, dd, J = 9.0, 7.3 Hz), 2.92-2.68 (8H, m), 2.62-2.56 (2H, m), 2.32-2.22 (2H, m), 2.19-1.93 (2H, m), 1.85-1.26 (18H, m). | 612 |
|---|---|---|---|
| 28 | 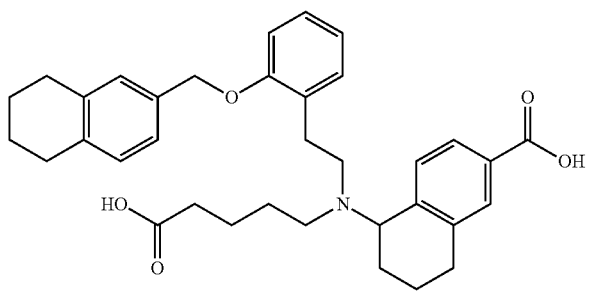 [SMILES: O=C(O)CCCCN(CCc1ccccc1OCc1ccc2c(c1)CCCC2)C1CCCc2cc(C(=O)O)ccc21] | (CD₃OD) δ: 7.70-7.69 (2H, m), 7.51 (1H, d, J = 8.8 Hz), 7.18 (1H, ddd, J = 9.3, 8.1, 1.8 Hz), 7.09 (1H, dd, J = 7.5, 1.8 Hz), 7.05-6.93 (4H, m), 6.85 (1H, ddd, J = 8.2, 7.5, 0.9 Hz), 4.91-4.78 (2H, m), 4.44-4.35 (1H, m), 3.01-2.63 (12H, m), 2.17 (2H, t, J = 6.6 Hz), 2.09-1.82 (2H, m), 1.80-1.75 (2H, m), 1.74-1.43 (8H, m). | 556 |
| 29 | 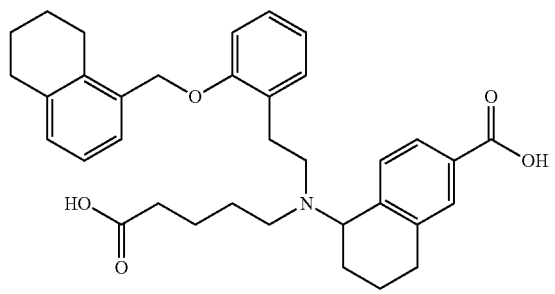 [SMILES: O=C(O)CCCCN(CCc1ccccc1OCc1cccc2c1CCCC2)C1CCCc2cc(C(=O)O)ccc21] | (DMSO-D₆) δ: 7.62-7.56 (2H, m), 7.50 (1H, d, J = 8.0 Hz), 7.18-7.10 (2H, m), 7.10-6.98 (4H, m), 6.83 (1H, ddd, J = 8.2, 7.3, 0.9 Hz), 4.96 (1H, d, J = 12.0 Hz), 4.92 (1H, d, J = 12.0 Hz), 3.89 (1H, dd, J = 8.6, 5.3 Hz), 2.85-2.55 (10H, m), 2.39 (2H, t, J = 6.4 Hz), 2.04 (2H, t, J = 7.2 Hz), 1.94-1.64 (6H, m), 1.59-1.29 (6H, m). | 556 |

TABLE 28

| 30 | 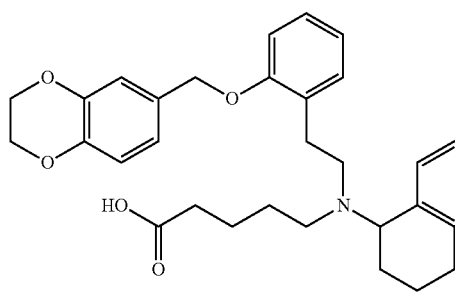 | (CD₃OD) δ: 7.74-7.68 (2H, m), 7.52 (1H, d, J = 8.6 Hz), 7.21-7.14 (1H, m), 7.08 (1H, dd, J = 7.5, 1.6 Hz), 6.94 (1H, dd, J = 7.5, 1.0 Hz), 6.85 (1H, ddd, J = 8.4, 7.5, 1.1 Hz), 6.81-6.77 (3H, m), 4.88-4.78 (2H, m), 4.49-4.37 (1H, m), 4.21 (4H, s), 3.04-2.66 (8H, m), 2.21 (2H, t, J = 6.6 Hz), 2.14-2.01 (1H, m), 1.99-1.85 (1H, m), 1.78-1.55 (6H, m). | 560 |
|---|---|---|---|
| 31 | 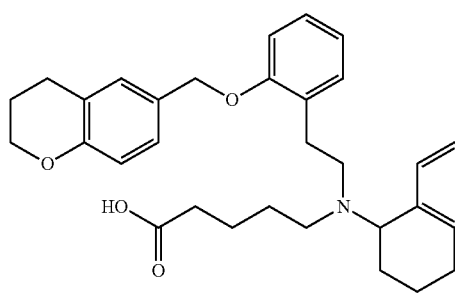 | (CD₃OD) δ: 7.72-7.69 (2H, m), 7.51 (1H, d, J = 8.8 Hz), 7.22-7.15 (1H, m), 7.09 (1H, dd, J = 7.5, 1.6 Hz), 7.05-6.95 (3H, m), 6.85 (1H, ddd, J = 8.4, 7.5, 1.0 Hz), 6.69 (1H, d, J = 7.5 Hz), 4.83 (2H, s), 4.46-4.35 (1H, m), 4.17-4.11 (2H, m), 2.97-2.65 (10H, m), 2.19 (2H, t, J = 6.6 Hz), 2.10-1.82 (4H, m), 1.77-1.39 (6H, m). | 558 |

TABLE 28-continued
| 32 | 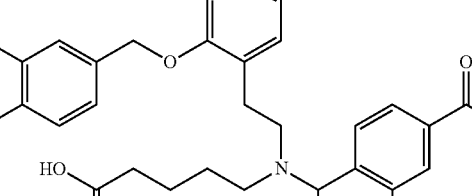 | (CD₃OD) δ: 7.77-7.68 (2H, m), 7.52 (1H, d, J = 8.8 Hz), 7.19 (1H, ddd, J = 8.3, 7.5, 1.6 Hz), 7.10 (1H, dd, J = 7.5, 1.6 Hz), 7.05-6.93 (4H, m), 6.86 (1H, ddd, J = 8.4, 7.5, 0.9 Hz), 4.84 (2H, s), 4.49-4.40 (1H, m), 3.04-2.64 (12H, m), 2.20 (2H, t, J = 6.6 Hz), 2.11-1.95 (3H, m), 1.95-1.81 (1H, m), 1.76-1.40 (6H, m). | 574 |
| --- | --- | --- | --- |
| 33 | 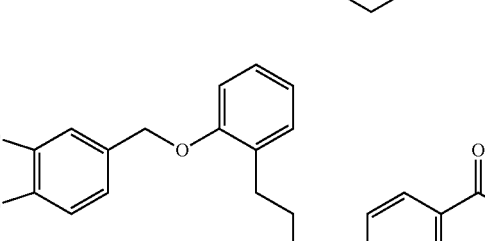 | (CD₃OD) δ: 7.72-7.67 (2H, m), 7.51 (1H, d, J = 7.5 Hz), 7.18 (1H, ddd, J = 8.0, 7.5, 1.6 Hz), 7.09 (1H, dd, J = 7.5, 1.6 Hz), 6.95 (1H, d, J = 7.5 Hz), 6.86 (1H, ddd, J = 8.4, 7.5, 0.9 Hz), 6.83-6.75 (3H, m), 5.94 (2H, s), 4.88-4.80 (2H, m), 4.47-4.38 (1H, m), 3.01-2.67 (8H, m), 2.21 (2H, t, J = 6.6 Hz), 2.14-2.01 (1H, m), 1.99-1.87 (1H, m), 1.79-1.46 (6H, m). | 546 |
TABLE 29
| 34 | 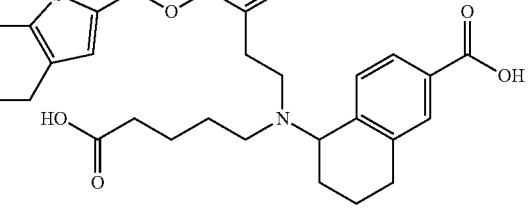 | (CD₃OD) δ: 7.78-7.69 (2H, m), 7.53 (1H, d, J = 8.6 Hz), 7.19 (1H, ddd, J = 8.2, 7.5, 1.7 Hz), 7.09 (1H, dd, J = 7.5, 1.7 Hz), 6.99 (1H, dd, J = 8.2, 1.0 Hz), 6.87 (1H, ddd, J = 8.4, 7.5, 1.0 Hz), 6.67 (1H, s), 5.05 (1H, d, J = 11.7 Hz), 5.00 (1H, d, J = 11.7 Hz), 4.55-4.45 (1H, m), 3.00-2.86 (3H, m), 2.85-2.72 (5H, m), 2.69 (2H, t, J = 5.6 Hz), 2.54 (2H, t, J = 5.6 Hz), 2.21 (2H, t, J = 6.8 Hz), 2.17-2.05 (1H, m), 2.01-1.87 (1H, m), 1.87-1.44 (10H, m). | 562 |
| --- | --- | --- | --- |
| 35 | 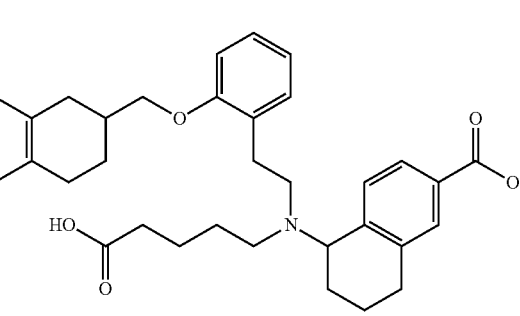 | (CD₃OD) δ: 7.70-7.60 (2H, m), 7.48 (1H, d, J = 8.1 Hz), 7.17 (1H, ddd, J = 8.1, 7.3, 1.7 Hz), 7.11-7.07 (1H, m), 7.06-6.97 (4H, m), 6.91-6.80 (2H, m), 4.40-4.26 (1H, m), 3.91-3.72 (2H, m), 3.03-2.62 (11H, m), 2.61-2.46 (1H, m), 2.22 (2H, t, J = 6.5 Hz), 2.18-1.86 (4H, m), 1.83-1.40 (7H, m). | 556 |
| 36 | 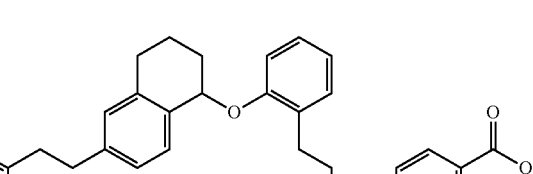 | (CD₃OD) δ: 7.75-7.71 (2H, m), 7.51-7.47 (1H, m), 7.26-6.95 (11H, m), 6.90-6.84 (1H, m), 5.44-5.39 (1H, m), 4.50-4.41 (1H, m), 2.96-2.61 (14H, m), 2.22-1.42 (14H, m). | 646 |

TABLE 29-continued
| 37 | 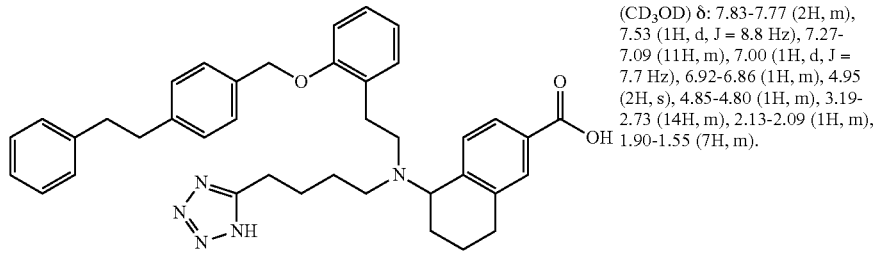 | (CD₃OD) δ: 7.83-7.77 (2H, m), 7.53 (1H, d, J = 8.8 Hz), 7.27-7.09 (11H, m), 7.00 (1H, d, J = 7.7 Hz), 6.92-6.86 (1H, m), 4.95 (2H, s), 4.85-4.80 (1H, m), 3.19-2.73 (14H, m), 2.13-2.09 (1H, m), 1.90-1.55 (7H, m). | 630 |
| --- | --- | --- | --- |
| 38 | 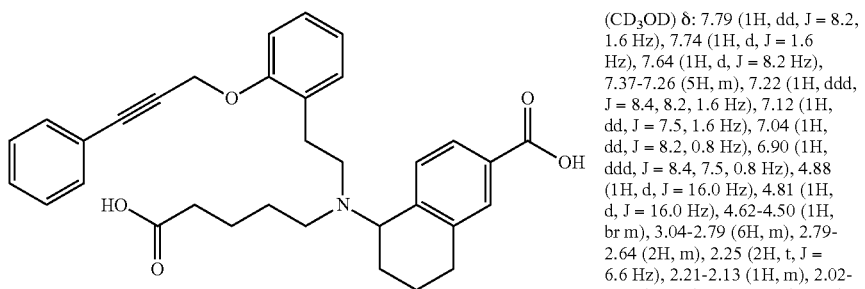 | (CD₃OD) δ: 7.79 (1H, dd, J = 8.2, 1.6 Hz), 7.74 (1H, d, J = 1.6 Hz), 7.64 (1H, d, J = 8.2 Hz), 7.37-7.26 (5H, m), 7.22 (1H, ddd, J = 8.4, 8.2, 1.6 Hz), 7.12 (1H, dd, J = 7.5, 1.6 Hz), 7.04 (1H, dd, J = 8.2, 0.8 Hz), 6.90 (1H, ddd, J = 8.4, 7.5, 0.8 Hz), 4.88 (1H, d, J = 16.0 Hz), 4.81 (1H, d, J = 16.0 Hz), 4.62-4.50 (1H, br m), 3.04-2.79 (6H, m), 2.79-2.64 (2H, m), 2.25 (2H, t, J = 6.6 Hz), 2.21-2.13 (1H, m), 2.02-1.88 (1H, m), 1.88-1.52 (6H, m). | 526 |
TABLE 30
| 39 | 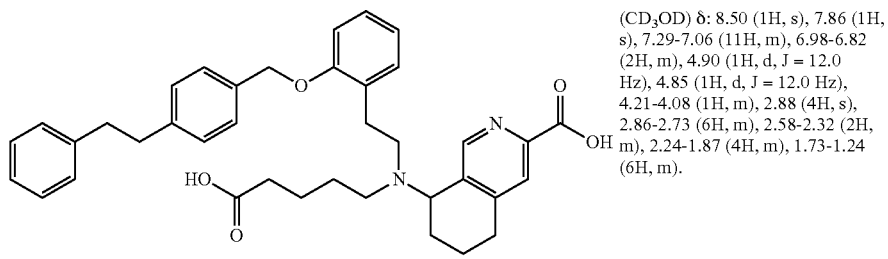 | (CD₃OD) δ: 8.50 (1H, s), 7.86 (1H, s), 7.29-7.06 (11H, m), 6.98-6.82 (2H, m), 4.90 (1H, d, J = 12.0 Hz), 4.85 (1H, d, J = 12.0 Hz), 4.21-4.08 (1H, m), 2.88 (4H, s), 2.86-2.73 (6H, m), 2.58-2.32 (2H, m), 2.24-1.87 (4H, m), 1.73-1.24 (6H, m). | 607 |
| --- | --- | --- | --- |
| 40 | 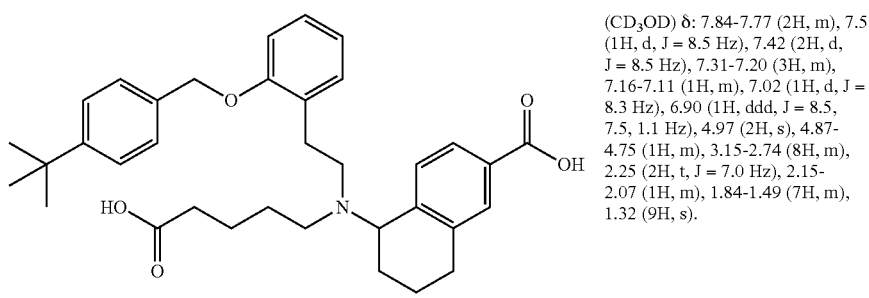 | (CD₃OD) δ: 7.84-7.77 (2H, m), 7.53 (1H, d, J = 8.5 Hz), 7.42 (2H, d, J = 8.5 Hz), 7.31-7.20 (3H, m), 7.16-7.11 (1H, m), 7.02 (1H, d, J = 8.3 Hz), 6.90 (1H, ddd, J = 8.5, 7.5, 1.1 Hz), 4.97 (2H, s), 4.87-4.75 (1H, m), 3.15-2.74 (8H, m), 2.25 (2H, t, J = 7.0 Hz), 2.15-2.07 (1H, m), 1.84-1.49 (7H, m), 1.32 (9H, s). | 558 |
| 41 | 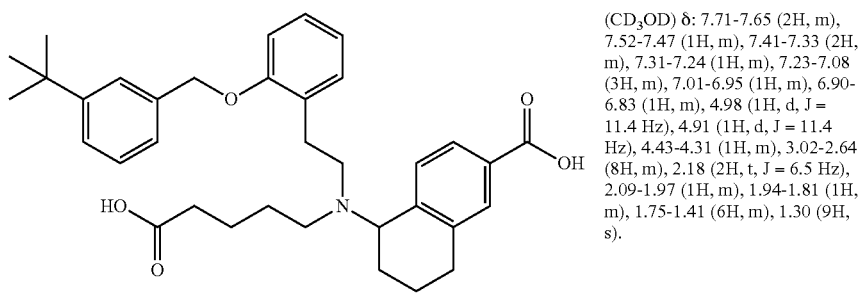 | (CD₃OD) δ: 7.71-7.65 (2H, m), 7.52-7.47 (1H, m), 7.41-7.33 (2H, m), 7.31-7.24 (1H, m), 7.23-7.08 (3H, m), 7.01-6.95 (1H, m), 6.90-6.83 (1H, m), 4.98 (1H, d, J = 11.4 Hz), 4.91 (1H, d, J = 11.4 Hz), 4.43-4.31 (1H, m), 3.02-2.64 (8H, m), 2.18 (2H, t, J = 6.5 Hz), 2.09-1.97 (1H, m), 1.94-1.81 (1H, m), 1.75-1.41 (6H, m), 1.30 (9H, s). | 558 |

TABLE 30-continued
| 42 | 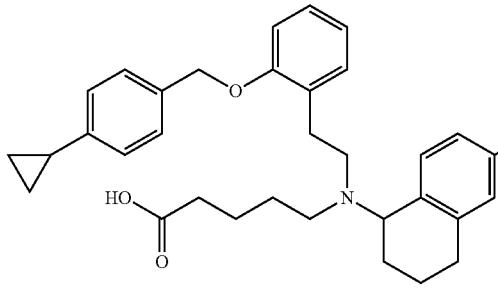 | (CD$_3$OD) δ: 7.76-7.73 (2H, m), 7.53-7.50 (1H, m), 7.23-7.17 (3H, m), 7.11-6.97 (4H, m), 6.89-6.84 (1H, m), 4.93 (1H, d, J = 11.2 Hz), 4.89 (1H, d, J = 11.2 Hz), 4.57-4.52 (1H, m), 2.99-2.94 (3H, m), 2.82-2.72 (5H, m), 2.21 (2H, t, J = 6.8 Hz), 2.04-1.85 (3H, m), 1.73-1.48 (6H, m), 0.99-0.93 (2H, m), 0.69-0.63 (2H, m). | 542 |
|---|---|---|---|
| 43 | 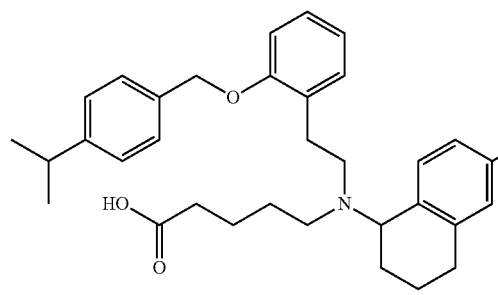 | (DMSO-D$_6$) δ: 7.58-7.56 (2H, m), 7.21-7.14 (7H, m), 6.97 (1H, d, J = 8.1 Hz), 6.82 (1H, t, J = 7.4 Hz), 5.06 (1H, s), 4.94 (1H, d, J = 12.0 Hz), 4.88 (1H, d, J = 12.0 Hz), 3.94-3.88 (1H, m), 2.90-2.85 (2H, m), 2.71-2.63 (4H, m), 2.43-2.42 (3H, m), 2.11-2.09 (2H, m), 1.98-1.84 (2H, m), 1.49-1.38 (5H, m), 1.18 (6H, d, J = 6.8 Hz). | 544 |
TABLE 31
| 44 | 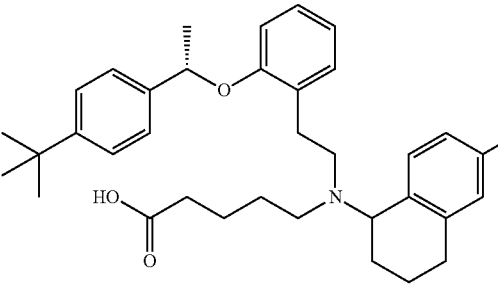 | (CD$_3$OD) δ: 7.76 (2H, d, J = 6.1 Hz), 7.63 (1H, t, J = 9.3 Hz), 7.34-7.27 (2H, m), 7.20 (1H, d, J = 8.4 Hz), 7.14-6.96 (3H, m), 6.80-6.66 (2H, m), 5.32-5.17 (1H, m), 4.55-4.42 (1H, m), 3.03-2.75 (8H, m), 2.32-2.13 (3H, m), 2.08-1.94 (1H, m), 1.90-1.56 (6H, m), 1.48, 1.45 (3H, each d, J = 6.4 Hz), 1.29, 1.27 (9H, each s). | 572 |
|---|---|---|---|
| 45 | 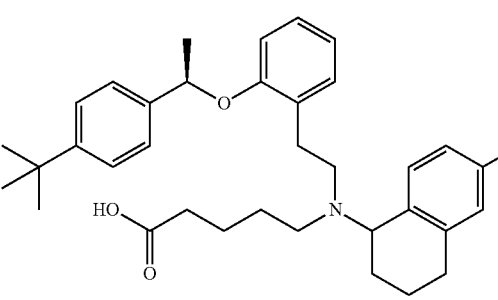 | (CD$_3$OD) δ: 7.78-7.72 (2H, m), 7.68-7.59 (1H, m), 7.34-7.27 (2H, m), 7.20 (1H, d, J = 8.4 Hz), 7.14-6.96 (3H, m), 6.80-6.66 (2H, m), 5.32-5.17 (1H, m), 4.48-4.38 (1H, m), 3.03-2.75 (8H, m), 2.32-2.13 (3H, m), 2.08-1.94 (1H, m), 1.90-1.56 (6H, m), 1.47, 1.44 (3H, each d, J = 6.4 Hz), 1.28, 1.27 (9H, each s). | 572 |
| 46 | 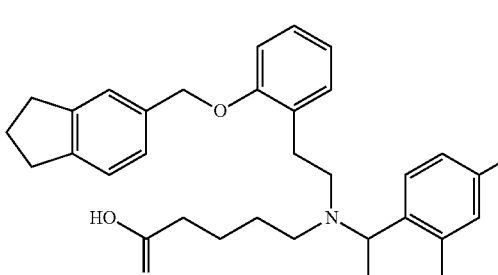 | (CD$_3$OD) δ: 7.75-7.66 (2H, m), 7.51 (1H, d, J = 8.6 Hz), 7.24-7.13 (3H, m), 7.12-7.04 (2H, m), 6.98 (1H, d, J = 7.7 Hz), 6.86 (1H, ddd, J = 8.2, 7.4, 0.9 Hz), 4.90 (2H, s), 4.54-4.33 (1H, m), 3.02-2.63 (12H, m), 2.18 (2H, t, J = 6.8 Hz), 2.12-1.96 (3H, m), 1.95-1.79 (1H, m), 1.78-1.39 (6H, m). | 542 |

TABLE 31-continued

| | | | |
|---|---|---|---|
| 47 | (structure) | (CD₃OD) δ: 7.95-7.82 (2H, m), 7.47 (1H, d, J = 7.9 Hz), 7.30-7.19 (1H, m), 7.18-6.98 (5H, m), 6.89 (1H, ddd, J = 8.2, 7.3, 0.9 Hz), 5.10-5.02 (1H, m), 4.94 (2H, s), 3.17-2.79 (7H, m), 2.78-2.66 (4H, m), 2.39-2.23 (2H, m), 2.19 (2H, t, J = 6.8 Hz), 1.83-1.41 (9H, m). | 594 |
| 48 | (structure) | (DMSO-D₆) δ: 7.42 (1H, d, J = 8.0 Hz), 7.33 (1H, dd, J = 8.0, 1.7 Hz), 7.21 (1H, d, J = 1.7 Hz), 7.16-6.96 (6H, m), 6.83 (1H, ddd, J = 8.6, 7.5, 1.3 Hz), 4.94 (1H, d, J = 11.5 Hz), 4.89 (1H, d, J = 11.5 Hz), 4.29-4.20 (1H, m), 4.11-3.96 (2H, m), 3.02-2.58 (11H, m), 2.15-2.05 (2H, m), 1.98-1.82 (2H, m), 1.78-1.65 (4H, m), 1.55-1.35 (3H, m). | 558 |
| 49 | (structure) | (DMSO-D₆) δ: 7.46-7.20 (10H, m), 7.16-7.05 (2H, m), 7.01-6.94 (3H, m), 6.83 (1H, ddd, J = 8.5, 7.3, 1.1 Hz), 5.10 (2H, S), 4.96 (1H, d, J = 11.9 Hz), 4.91 (1H, d, J = 11.9 Hz), 4.29-4.20 (1H, m), 4.09-3.96 (2H, m), 2.85-2.55 (4H, m), 2.53-2.40 (2H, m), 2.13 (2H, t, J = 7.1 Hz), 1.99-1.80 (2H, m), 1.58-1.35 (4H, m). | 610 |

Compounds of Examples 50 to 69, which have been produced by using the corresponding optically active compound of Reference Example according to the same method as Example 1, are shown in Table 33 to Table 37.

TABLE 33

| Example | Structural formula | ¹H-NMR | ESI-MS (M + H)⁺ | Optical rotation [α]_D Optical purity |
|---|---|---|---|---|
| 50 | (structure) | (CD₃OD) δ: 7.76-7.76 (2H, m), 7.54-7.51 (1H, m), 7.26-7.10 (11H, m), 6.99 (1H, d, J = 7.7 Hz), 6.88 (1H, dd, J = 7.6, 0.9 Hz), 4.96 (1H, d, J = 11.6 Hz), 4.92 (1H, d, J = 11.6 Hz), 4.65-4.63 (1H, m), 3.07-2.73 (12H, m), 2.23 (2H, t, J = 6.9 Hz), 2.14-2.08 (1H, m), 1.90-1.49 (7H, m). | 606 | +74.0 (c = 0.66, CHCl₃) 99.84% ee |

TABLE 33-continued

| Example | Structural formula | ¹H-NMR | ESI-MS (M + H)⁺ | Optical rotation [α]$_D$ Optical purity |
|---|---|---|---|---|
| 51 | | (CD$_3$OD) δ: 7.75-7.73 (2H, m), 7.52-7.50 (1H, m), 7.25-7.09 (11H, m), 6.98 (1H, d, J = 7.5 Hz), 6.87 (1H, td, J = 7.4, 1.0 Hz), 4.95 (1H, d, J = 11.4 Hz), 4.91 (1H, d, J = 11.4 Hz), 4.57-4.52 (1H, m), 3.00-2.72 (12H, m), 2.22 (2H, t, J = 6.8 Hz), 2.09-2.06 (1H, m), 1.90-1.88 (1H, m), 1.75-1.52 (6H, m). | 606 | −78.0 (c = 0.24, CHCl$_3$) 98.76% ee |
| 52 | | (CD$_3$OD) δ: 7.96-7.85 (2H, m), 7.50 (1H, d, J = 8.1 Hz), 7.34-7.08 (11H, m), 7.04 (1H, d, J = 8.3 Hz), 6.90 (1H, ddd, J = 8.3, 7.5, 0.9 Hz), 5.10 (1H, dd, J = 8.3, 4.9 Hz), 4.99 (2H, s), 3.23-2.80 (12H, m), 2.44-2.13 (4H, m), 1.83-1.43 (4H, m). | 592 | +26.2 (c = 0.49, MeOH) 99.44% ee |

TABLE 34

| Example | Structural formula | ¹H-NMR | ESI-MS (M + H)⁺ | Optical rotation [α]$_D$ Optical purity |
|---|---|---|---|---|
| 53 | | (CD$_3$OD) δ: 7.92-7.83 (2H, m), 7.46 (1H, d, J = 7.9 Hz), 7.32-7.08 (11H, m), 7.02 (1H, d, J = 8.1 Hz), 6.89 (1H, ddd, J = 8.3, 7.5, 0.9 Hz), 5.05 (1H, dd, J = 8.3, 5.0 Hz), 4.98 (2H, s), 3.15-2.78 (12H, m), 2.42-2.09 (4H, m), 1.78-1.43 (4H, m). | 592 | −34.7 (c = 0.48, MeOH) 99.60% ee |
| 54 | | (DMSO-D$_6$) δ: 7.41 (1H, d, J = 8.1 Hz), 7.34-7.09 (13H, m), 6.98 (1H, d, J = 8.1 Hz), 6.84 (1H, t, J = 7.4 Hz), 4.97 (1H, d, J = 11.7 Hz), 4.91 (1H, d, J = 11.7 Hz), 4.30-4.26 (1H, m), 4.12-3.97 (2H, m), 3.34-3.30 (1H, m), 2.86 (4H, s), 2.82-2.54 (3H, m), 2.44-2.40 (2H, m), 2.11 (2H, t, J = 6.5 Hz), 2.02-1.73 (2H, m), 1.49-1.32 (4H, m). | 608 | +67.0 (c = 0.27, MeOH) 99.99% ee |
| 55 | | (DMSO-D$_6$) δ: 7.41 (1H, d, J = 8.1 Hz), 7.34-7.09 (13H, m), 6.98 (1H, d, J = 8.1 Hz), 6.84 (1H, t, J = 7.4 Hz), 4.97 (1H, d, J = 11.7 Hz), 4.91 (1H, d, J = 11.7 Hz), 4.30-4.26 (1H, m), 4.12-3.97 (2H, m), 3.33-3.31 (1H, m), 2.86 (4H, S), 2.81-2.54 (3H, m), 2.44-2.40 (2H, m), 2.12 (2H, t, J = 6.4 Hz), 1.92-1.78 (2H, m), 1.50-1.35 (4H, m). | 608 | −63.2 (c = 0.25, MeOH) 99.99% ee |

TABLE 34-continued

| 56 | (structure) | (CD₃OD) δ: 7.82-7.79 (2H, m), 7.57 (1H, d, J = 8.2 Hz), 7.21 (1H, t, J = 7.7 Hz), 7.11 (1H, d, J = 7.1 Hz), 6.98 (1H, d, J = 8.2 Hz), 6.90-6.82 (4H, m), 4.88-4.76 (3H, m), 4.22 (4H, s), 3.14-2.77 (8H, m), 2.25 (2H, t, J = 6.9 Hz), 2.16-2.09 (1H, m), 1.97-1.50 (7H, m). | 560 | +48.2 (c = 0.25, MeOH) |
| --- | --- | --- | --- | --- |
| 57 | (structure) | (CD₃OD) δ: 7.85-7.83 (2H, m), 7.56 (1H, d, J = 8.8 Hz), 7.23 (1H, ddd, J = 9.9, 7.5, 1.7 Hz), 7.12 (1H, dd, J = 7.3, 1.3 Hz), 7.00 (1H, d, J = 8.1 Hz), 6.91-6.83 (4H, m), 4.92-4.87 (3H, m), 4.23 (4H, s), 3.22-2.80 (8H, m), 2.27 (2H, t, J = 7.1 Hz), 2.19-2.12 (1H, m), 1.97-1.47 (7H, m). | 560 | −52.1 (c = 0.24, MeOH) 99.99% ee |

TABLE 35

| 58 | (structure) | (CD₃OD) δ: 7.74-7.66 (2H, m), 7.50 (1H, d, J = 8.8 Hz), 7.20 (1H, t, J = 7.6 Hz), 7.11-6.97 (5H, m), 6.87 (1H, t, J = 7.6 Hz), 4.95-4.85 (2H, m), 4.40 (1H, s), 2.98-2.65 (12H, m), 2.17 (2H, t, J = 6.4 Hz), 2.05-1.43 (12H, m). | 556 | +80.1 (c = 0.29, MeOH) 99.32% ee |
| --- | --- | --- | --- | --- |
| 59 | (structure) | (CD₃OD) δ: 7.72-7.65 (2H, m), 7.50 (1H, d, J = 8.8 Hz), 7.20 (1H, ddd, J = 8.8, 7.3, 1.2 Hz), 7.11-6.98 (5H, m), 6.87 (1H, ddd, J = 8.4, 7.3, 0.9 Hz), 4.96-4.82 (2H, m), 4.37 (1H, t, J = 7.7 Hz), 2.98-2.62 (12H, m), 2.17 (2H, t, J = 6.5 Hz), 2.05-1.92 (1H, m), 1.90-1.42 (11H, m). | 556 | −81.8 (c = 0.36, MeOH) 99.88% ee |
| 60 | (structure) | (DMSO-D₆) δ: 7.58-7.50 (3H, m), 7.39 (1H, s), 7.33 (1H, d, J = 7.9 Hz), 7.27 (1H, t, J = 7.4 Hz), 7.19-7.08 (3H, m), 6.99 (1H, d, J = 8.1 Hz), 6.84 (1H, t, J = 7.4 Hz), 4.99 (1H, d, J = 11.6 Hz), 4.91 (1H, d, J = 11.6 Hz), 3.94-3.91 (1H, m), 3.33-3.31 (1H, m), 2.83-2.76 (1H, m), 2.68-2.56 (4H, m), 2.44-2.40 (2H, m), 2.10 (2H, t, J = 6.1 Hz), 1.95-1.84 (2H, m), 1.50-1.31 (6H, m), 1.26 (9H, s). | 558 | +86.0 (c = 0.27, MeOH) 99.64% ee |

TABLE 35-continued

| 61 | (structure) | (DMSO-D$_6$) δ: 7.59-7.50 (3H, m), 7.39-7.24 (3H, m), 7.19-7.08 (3H, m), 6.99 (1H, d, J = 8.1 Hz), 6.84 (1H, t, J = 7.5 Hz), 4.99 (1H, d, J = 11.8 Hz), 4.91 (1H, d, J = 11.8 Hz), 3.93-3.90 (1H, m), 3.33-3.31 (1H, m), 2.80-2.76 (1H, m), 2.67-2.55 (4H, m), 2.44-2.40 (2H, m), 2.10 (2H, t, J = 7.0 Hz), 1.94-1.84 (2H, m), 1.47-1.32 (6H, m), 1.26 (9H, s). | 558 | −78.0 (c = 0.25, MeOH) 99.99% ee |

TABLE 36

| 62 | (structure) | (CD$_3$OD) δ: 7.76-7.69 (2H, m), 7.56-7.49 (1H, m), 7.25-7.14 (3H, m), 7.13-7.01 (3H, m), 6.97 (1H, d, J = 8.2 Hz), 6.86 (1H, ddd, J = 8.1, 7.3, 0.7 Hz), 4.92 (1H, d, J = 11.2 Hz), 4.87 (1H, d, J = 11.2 Hz), 4.45 (1H, t, J = 7.3 Hz), 3.03-2.83 (3H, m), 2.83-2.63 (5H, m), 2.20 (2H, t, J = 6.6 Hz), 2.10-1.96 (1H, m), 1.95-1.81 (2H, m), 1.76-1.42 (6H, m), 1.01-0.91 (2H, m), 0.70-0.62 (2H, m). | 542 | +86.2 (c = 0.19, MeOH) 99.42% ee |
| 63 | (structure) | (CD$_3$OD) δ: 7.68-7.62 (2H, m), 7.47-7.41 (1H, m), 7.17-7.05 (3H, m), 7.04-6.92 (3H, m), 6.88 (1H, d, J = 8.2 Hz), 6.77 (1H, ddd, J = 8.1, 7.3, 0.7 Hz), 4.83 (1H, d, J = 11.2 Hz), 4.79 (1H, d, J = 11.2 Hz), 4.41 (1H, t, J = 7.3 Hz), 3.02-2.77 (3H, m), 2.77-2.54 (5H, m), 2.11 (2H, t, J = 6.6 Hz), 2.02-1.88 (1H, m), 1.88-1.72 (2H, m), 1.69-1.32 (6H, m), 0.93-0.81 (2H, m), 0.62-0.53 (2H, m). | 542 | −78.7 (c = 0.19, MeOH) 99.82% ee |
| 64 | (structure) | (CD$_3$OD) δ: 7.91-7.89 (2H, m), 7.68-7.65 (1H, m), 7.32 (2H, d, J = 8.4 Hz), 7.13-7.02 (4H, m), 6.82-6.73 (2H, m), 5.31 (1H, q, J = 6.2 Hz), 5.06-5.00 (1H, m), 3.34-2.87 (8H, m), 2.37 (2H, t, J = 7.0 Hz), 2.10-1.64 (7H, m), 1.51 (3H, d, J = 6.2 Hz), 1.29 (9H, s). | 572 | — 96.22% ee |
| 65 | (structure) | (CD$_3$OD) δ: 7.79-7.76 (2H, m), 7.65 (1H, d, J = 8.1 Hz), 7.33 (2H, d, J = 8.4 Hz), 7.20 (2H, d, J = 8.4 Hz), 7.08-7.00 (2H, m), 6.80-6.74 (2H, m), 5.28 (1H, q, J = 6.4 Hz), 4.57-4.52 (1H, m), 3.07-2.76 (8H, m), 2.28 (2H, t, J = 6.8 Hz), 2.22-2.15 (1H, m), 2.02-1.98 (1H, m), 1.87-1.59 (6H, m), 1.47 (3H, d, J = 6.4 Hz), 1.28 (9H, s). | 572 | — 99.67% ee |

TABLE 37

| | | | | |
|---|---|---|---|---|
| 66 | (structure) | (CD₃OD) δ: 7.74-7.68 (2H, m), 7.52 (1H, d, J = 8.8 Hz), 7.22-7.14 (3H, m), 7.09-7.07 (2H, m), 6.97 (1H, d, J = 8.2 Hz), 6.85 (1H, ddd, J = 8.4, 7.5, 1.1 Hz), 4.94-4.86 (2H, m), 4.50-4.40 (1H, m), 3.00-2.65 (12H, m), 2.17 (2H, t, J = 6.7 Hz), 2.11-1.98 (3H, m), 1.93-1.80 (1H, m), 1.74-1.40 (6H, m). | 542 | +79.4 (c = 0.30, MeOH) 99.32% ee |
| 67 | (structure) | (CD₃OD) δ: 7.74-7.69 (2H, m), 7.51 (1H, d, J = 8.6 Hz), 7.22-7.15 (3H, m), 7.10-7.08 (2H, m), 6.98 (1H, d, J = 7.5 Hz), 6.86 (1H, ddd, J = 8.4, 7.3, 0.9 Hz), 4.95-4.85 (2H, m), 4.47 (1H, t, J = 7.6 Hz), 2.97-2.71 (12H, m), 2.18 (2H, t, J = 6.7 Hz), 2.12-1.98 (3H, m), 1.94-1.82 (1H, m), 1.76-1.41 (6H, m). | 542 | −78.5 (c = 0.27, MeOH) 99.42% ee |
| 68 | (structure) | (CD₃OD) δ: 7.77-7.68 (2H, m), 7.52 (1H, d, J = 8.6 Hz), 7.29-7.15 (5H, m), 7.11 (1H, dd, J = 7.4, 1.6 Hz), 6.98 (1H, d, J = 8.2 Hz), 6.87 (1H, ddd, J = 8.2, 7.3, 0.9 Hz), 4.94 (1H, d, J = 11.4 Hz), 4.90 (1H, d, J = 11.4 Hz), 4.51 (1H, t, J = 7.9 Hz), 3.04-2.65 (10H, m), 2.21 (2H, t, J = 6.7 Hz), 2.13-1.80 (2H, m), 1.79-1.41 (5H, m), 1.24 (6H, d, J = 7.0 Hz). | 544 | +81.6 (c = 0.21, MeOH) 97.64% ee |
| 69 | (structure) | (CD₃OD) δ: 7.76-7.64 (2H, m), 7.52 (1H, d, J = 8.6 Hz), 7.29-7.14 (5H, m), 7.10 (1H, dd, J = 7.4, 1.6 Hz), 6.97 (1H, d, J = 8.2 Hz), 6.86 (1H, ddd, J = 8.2, 7.3, 0.9 Hz), 4.94 (1H, d, J = 11.4 Hz), 4.89 (1H, d, J = 11.4 Hz), 4.44 (1H, t, J = 7.9 Hz), 3.03-2.63 (10H, m), 2.20 (2H, t, J = 6.7 Hz), 2.11-1.79 (2H, m), 1.77-1.42 (5H, m), 1.24 (6H, d, J = 7.0 Hz). | 544 | −92.9 (c = 0.20, MeOH) 99.99% ee |

In the following test Examples, the compound of the invention was tested regarding the sGC activating function.

Test Example 1

Maximum Effect of sGC Activating Function

For the assay, Chinese hamster ovary cells (CHO-K1 cells) in which human sGC α subunit and β subunit and mouse cyclic nucleotide gated channel (CNGA2) are stably expressed were used.

CHO-K1 cells in which human sGC and mouse CNGA2 are stably expressed were cultured at 37° C. in F-12 medium containing 10% (v/v) fetal bovine serum (FBS), penicillin (100 U/mL), streptomycin (100 μg/mL), G418 (250 μg/mL), and zeocin (250 μg/mL). The cells were suspended in the culture medium and seeded onto a 96-well plate, and then cultured at 37° C. for 24 hours. After washing with assay buffer 1 (140 mmol/L sodium chloride, 5 mmol/L potassium chloride, 0.5 mmol/L magnesium chloride, 0.01 mmol/L calcium chloride, 10 mmol/L glucose, 0.4 mmol/L magnesium sulfate, 10 mmol/L 4-(2-hydroxyethyl)piperazin-1-ylethane sulfonic acid, and 125 μmol/L sulfinpyrazone, pH 7.4), an indicator solution in which FURA2-AM as a fluorescent $Ca^{2+}$ indicator is dissolved at concentration of 5 μmol/L in assay buffer 1 was added followed by culture for 60 minutes at 37° C. The indicator solution was removed. After washing with assay buffer 1, the test compound solution was added and incubated for 10 minutes at room temperature. The plate was placed in a fluorometer (Flex Station II, Molecular Devices, LLC), and then the intracellular calcium concentration was measured as fluorescence intensity ratio which is obtained from each excitation wavelength (excitation wavelength of 340 nm and 380 nm and detection wavelength of 510 nm).

The test compound solution was prepared by dissolving each of the test compounds in DMSO to a concentration of 10 mmol/L, and then adding the assay buffer 2 (140 mmol/L sodium chloride, 5 mmol/L potassium chloride, 0.5 mmol/L magnesium chloride, 1 mmol/L calcium chloride, 10 mmol/L glucose, 0.4 mmol/L magnesium sulfate, 10 mmol/L 4-(2-hydroxyethyl)piperazin-1-ylethane sulfonic acid, 125 µmol/L sulfinpyrazone, 100 µmol/L isobutylmethylxanthine, 10 µmol/L 1H-[1,2,4]-oxadiazole[4,3-a]quinoxalin-1-one (hereinbelow, ODQ), pH 7.4) for dilution to have test concentration of 10 µmol/L. For the evaluation of a case in which ODQ is not contained, the same evaluation was performed except that ODQ is excluded from assay buffer 2. As a control solution, a DMSO solution was used instead of the test compound solution.

The activity of the test compound corresponds to the increase ratio (%) of the sGC activity at the time of adding the test compound solution with respect to the sGC activity at the time of adding the control solution, and it was calculated by dividing the fluorescence intensity ratio at the time of adding the test compound by the fluorescence intensity ratio of the control solution and subtracting the sGC activity (100%) at the time of adding the control solution.

The assay results are shown in Table 38 and Table 39.

TABLE 38

| Test compound (Example No.) | Emax (%) ODQ− (Heme-dependent) | Emax (%) ODQ+ (Heme-independent) |
|---|---|---|
| 1 | 85.6 | 103.3 |
| 2 | 97.5 | 109.0 |
| 3 | 101.6 | 111.0 |
| 4 | 113.8 | 108.8 |
| 5 | 84.5 | 86.9 |
| 6 | 126.3 | 99.9 |
| 7 | 110.1 | 107.6 |
| 8 | 129.6 | 101.5 |
| 13 | 64.2 | 87.2 |
| 14 | 99.1 | 101.4 |
| 15 | 101.1 | 99.9 |

TABLE 39

| 16 | 116.2 | 97.5 |
|---|---|---|
| 17 | 114.6 | 91.8 |
| 19 | 88.7 | 88.0 |
| 22 | 107.6 | 100.2 |
| 23 | 125.5 | 104.5 |
| 24 | 134.8 | 114.2 |
| 26 | 119.4 | 86.9 |
| 27 | 113.0 | 96.6 |
| 29 | 140.9 | 133.0 |
| 41 | 109.1 | 140.3 |
| 42 | 86.7 | 122.5 |
| 43 | 90.3 | 107.4 |
| 45 | 95.3 | 121.3 |
| 46 | 81.3 | 122.7 |
| Cinaciguat | 53.0 | 86.0 |

In this assay, intracellular cGMP concentration increases as sGC is activated, and according to opening of CNGA2 following the increase of cGMP, intracellular $Ca^{2+}$ concentration increases. Thus, SGC activation can be measured by following the change in intracellular $Ca^{2+}$ concentration. Since ODQ is an oxidizing agent which is specific to a heme-binding iron atom and the heme iron atom is oxidized in the presence of ODQ, heme-dependent sGC activation does not occur. Thus, in the absence of ODQ, the maximum sGC activating function including the heme-dependent activation can be evaluated while the heme-independent sGC activating function can be evaluated in the presence of ODQ. Meanwhile, both in the presence or absence of ODQ, sGC activity has a constant value after exhibiting the maximum value at concentration of 10 µmol/L or higher for any test compound, including Cinaciguat as a Comparative Example, and therefore the activity value at 10 µmol/L was used as the maximum effect of sGC activity of each test compound (Emax).

As shown in Table 38 and Table 39, all compounds of the present invention significantly increased the sGC activity in the presence of ODQ, clearly indicating that they are a heme-independent direct sGC activating agent. Further, compared to Cinaciguat, the compounds of the present invention exhibited higher Emax in any case of having or not having ODQ, clearly indicating that it has more excellent sGC activating function than Cinaciguat.

Test Example 2

Heme-Independent Property of sGC Activating Function

For the representative compounds, activity was measured in the same manner as Test Example 1 at each test concentration of 0.0001, 0.001, 0.003, 0.01, 0.03, 0.1, 1, and 10 µmol/L.

The degree of heme-independent property of each test compound with regard to sGC activating function was obtained by dividing, for $EC_{50}$ measured from the concentration-activation curve which has been established from the above, $EC_{50}$ in the absence of ODQ by $EC_{50}$ in the presence of ODQ. Specifically, the smaller the $EC_{50}$ ratio is, the less the change in sGC activating function is, the change in the function being caused by the presence or absence of ODQ, and thus it is found to be more heme-independent.

$EC_{50}$ value was obtained by measuring the activity of each compound to be tested at concentrations of 0.0001, 0.001, 0.003, 0.01, 0.03, 0.1, 1, and 10 µmol/L and performing the calculation using four-parameter logistics model using Assay Explorer (Accelrys).

The test results are shown in Table 40.

TABLE 40

| Test compound (Example No.) | $EC_{50}$ Ratio (ODQ−/ODQ+) |
|---|---|
| 1 | 2.86 |
| 2 | 2.67 |
| 3 | 2.54 |
| 4 | 2.85 |
| 6 | 0.87 |
| 7 | 2.34 |
| 8 | 1.80 |
| 14 | 1.73 |
| 15 | 1.40 |
| 23 | 1.15 |
| 27 | 1.84 |
| 29 | 1.71 |
| Cinaciguat | 3.08 |

As shown in Table 40, it was found that all of the compounds of the present invention have lower $EC_{50}$ ratio than Cinaciguat and are more heme-independent compared to Cinaciguat.

Test Example 3

Evaluation of Blood Vessel Relaxing Function

The representative compounds of the present invention were evaluated by blood vessel relaxing function according to the following Test Example. In the assay, bleeding from the upper part of a heart of a rat (male, SD) was performed under anesthesia with pentobarbital (30 mg/kg) and then abdominal aorta was extracted. The connecting tissue adhered around blood vessel was removed from the abdominal aorta in an ice-cooled Krebs-Henseleit solution (KH solution) (118 mmol/L sodium chloride, 4.7 mmol/L potassium chloride, 1.2 mmol/L magnesium sulfate, 1.2 mmol/L potassium dihydrogen phosphate, 25 mmol/L sodium hydrogen carbonate, 2.5 mmol/L calcium chloride, and 10 mmol/L glucose, pH 7.4). After that, a ring specimen with length of 2 mm was prepared and fixed in 5 mL organ bath filled with a KH solution. The KH solution was kept at 37° C. and aerated with a mixture gas of 95% $O_2$ and 5% $CO_2$. The specimen was stabilized for 1 hour with static tension of 1 g. The KH solution was exchanged twice during that time. The tension on the specimen was recorded on a multi-channel recorder via pickup and amplifier. After the stabilization of the specimen, contraction was caused by using 1 μmol/L phenylephrine (Phe), and cumulative administration of each compound (0.001, 0.01, 0.03, 0.1, 0.3, 1, 3, 10, 30, 100, 1000, 10000 nmol/L) was performed. For the evaluation of a case in which 1H-1,2,4-oxadiazole-(4,3a)-quinoxalin-1-one (ODQ) is contained, 10 μmol/L ODQ was added 10 minutes before the Phe addition, and the same evaluation as above was performed.

$EC_{50}$ value was calculated using four-parameter logistics model using Assay Explorer (Accelrys). The test compound solution was dissolved in DMSO such that the concentration of each test compound is 1000 times the final concentration.

The test results are shown in Table 41.

TABLE 41

| Test compound (Example No.) | $EC_{50}$ Ratio (ODQ−/ODQ+) |
|---|---|
| 15 | 9.0 |
| 29 | 5.0 |
| 42 | 4.3 |
| 43 | 5.5 |
| 45 | 3.5 |
| 46 | 5.2 |
| Cinaciguat | 12.4 |

As shown in Table 41, it was found that all of the compounds of the present invention have lower $EC_{50}$ ratio than Cinaciguat and are more heme-independent than Cinaciguat.

INDUSTRIAL APPLICABILITY

The bicyclic compound of the present invention, a pharmaceutically acceptable salt thereof, or a solvate thereof has sGC activating function with excellent heme-independent property, and therefore it is useful as a pharmaceutical agent for prevention and treatment of various disorders that are related with soluble guanylate cyclase, for example, heart failure, hypertension, pulmonary hypertension, and ischemic heart disease.

The invention claimed is:
1. A compound of Formula (1):

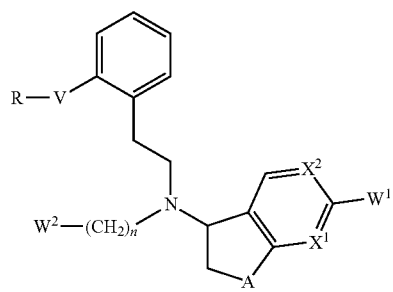

(1)

wherein
A represents a $C_1$-$C_3$ linear alkylene group, in which one methylene group is optionally substituted with O or S;

n represents an integer of from 3 to 5;
$X^1$ and $X^2$ each independently represent CH or N;
$W^1$ and $W^2$ each independently represent a carboxyl group or a tetrazolyl group;
V represents a $C_1$-$C_8$ linear or branched alkylene group, in which one methylene group is optionally substituted with O or S;
R represents a group selected from the group consisting of:

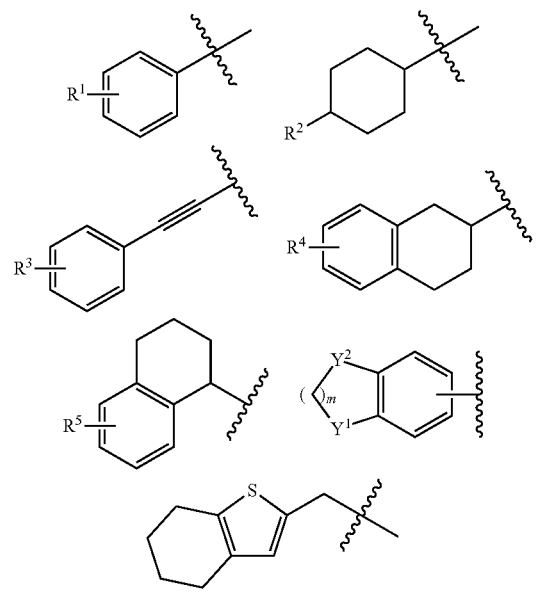

in which $R^1$, $R^2$, $R^3$, $R^4$ and $R^5$ represent a hydrogen atom, a halogen atom, a $C_1$-$C_6$ alkyl group which optionally comprises a substituent group, a $C_1$-$C_6$ alkoxy group, a $C_3$-$C_6$ cycloalkyl group, a $C_3$-$C_6$ cycloalkoxy group, a halo $C_1$-$C_4$ alkyl group, a halo $C_1$-$C_4$ alkoxy group, a vinyl group which optionally comprises a substituent group, an ethynyl group which optionally comprises a substituent group, an aryl group which optionally comprises a substituent group on an aromatic ring, an aryloxy group which optionally comprises a substituent group on an aromatic ring, a benzyl group which optionally comprises a substituent group on a benzene ring, a phenethyl group which optionally comprises a substituent group on a benzene ring, a benzyloxy group which optionally comprises a substituent group on a benzene ring, a benzylsulfanyl group which optionally comprises a substituent group on a benzene ring, a benzylamino group which optionally comprises a substituent group on a benzene ring, a phenyloxymethyl group which optionally comprises a substituent group on a benzene ring, a phenylsulfanylmethyl group which optionally comprises a substituent group on a benzene ring, or a phenylaminomethyl group which optionally comprises a substituent group on a benzene ring;
m represents an integer of 1 or 2; and
$Y^1$ and $Y^2$ each independently represent methylene, O or S, with the proviso that $Y^1$ and $Y^2$ do not simultaneously represent S,
a pharmaceutically acceptable salt thereof, or a solvate thereof.
2. The compound of claim 1, wherein, with regard to $R^1$, $R^2$, $R^3$, $R^4$ and $R^5$, a substituent group on the $C_1$-$C_6$ alkyl group is a $C_1$-$C_6$ alkoxy group, a $C_3$-$C_6$ cycloalkyl group, or a $C_3$-$C_6$ cycloalkoxy group, a substituent group on the vinyl group or ethynyl group is a $C_1$-$C_6$ alkyl group, a $C_3$-$C_6$ cycloalkyl group, a phenyl group, a halogenophenyl group, a $C_1$-$C_6$ alkylphenyl group, or a halo $C_1$-$C_4$ alkylphenyl group, a substituent group on the aryl or aryloxy group is a halogen atom, a $C_1$-$C_6$ alkyl group, a $C_1$-$C_6$ alkoxy group, or a halo $C_1$-$C_4$ alkyl group, and a substituent group on the benzene ring is a halogen atom, a $C_1$-$C_6$ alkyl group, or a halo $C_1$-$C_4$ alkyl group, a pharmaceutically acceptable salt thereof, or a solvate thereof.

3. The compound of claim 1, wherein, in Formula (1),

A is a methylene group, —O—, —$CH_2CH_2$—, —$CH_2O$—, —$OCH_2$—, —$CH_2CH_2CH_2$—, —$CH_2OCH_2$—, —$CH_2SCH_2$—, or —$CH_2CH_2O$—;

n is an integer of from 3 to 5;

$W^1$ and $W^2$ are a carboxyl group;

V is —$CH_2CH_2$—, —$CH(CH_3)O$— or —$CH_2O$—; and

R is a group selected from the group consisting of:

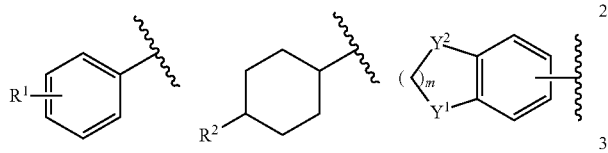

where $R^1$ and $R^2$ represent a hydrogen atom, a halogen atom, a $C_1$-$C_6$ alkyl group which optionally comprises a substituent group, a $C_1$-$C_6$ alkoxy group, a $C_3$-$C_6$ cycloalkyl group, a $C_3$-$C_6$ cycloalkoxy group, a halo $C_1$-$C_4$ alkyl group, a halo $C_1$-$C_4$ alkoxy group, a vinyl group which optionally comprises a substituent group, an ethynyl group which optionally comprises a substituent group, an aryl group which optionally comprises a substituent group on an aromatic ring, an aryloxy group which optionally comprises a substituent group on an aromatic ring, a benzyl group which optionally comprises a substituent group on a benzene ring, a phenethyl group which optionally comprises a substituent group on a benzene ring, a benzyloxy group which optionally comprises a substituent group on a benzene ring, a benzylsulfanyl group which optionally comprises a substituent group on a benzene ring, a benzylamino group which optionally comprises a substituent group on a benzene ring, a phenyloxymethyl group which optionally comprises a substituent group on a benzene ring, a phenylsulfanylmethyl group which optionally comprises a substituent group on a benzene ring, or a phenylaminomethyl group which optionally comprises a substituent group on a benzene ring;

m represents an integer of 1 or 2; and $Y^1$ and $Y^2$ each independently represent methylene, O or S, with the proviso that $Y^1$ and $Y^2$ do not simultaneously represent S, a pharmaceutically acceptable salt thereof, or a solvate thereof.

4. The compound of claim 1, wherein, in Formula (1),

A is a methylene group, —O—, —$CH_2CH_2$—, —$CH_2O$—, —$OCH_2$—, —$CH_2CH_2CH_2$—, —$CH_2OCH_2$—, —$CH_2SCH_2$—, or —$CH_2CH_2O$—;

n is an integer of 4;

$W^1$ and $W^2$ are a carboxyl group;

V is —$CH_2CH_2$—, —$CH(CH_3)O$— or —$CH_2O$—; and

R is a group selected from the group consisting of:

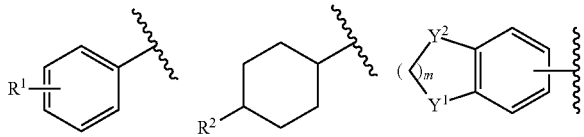

where $R^1$ and $R^2$ represent a hydrogen atom, a halogen atom, a $C_1$-$C_6$ alkyl group which optionally comprises a substituent group, a $C_1$-$C_6$ alkoxy group, a $C_3$-$C_6$ cycloalkyl group, a $C_3$-$C_6$ cycloalkoxy group, a halo $C_1$-$C_4$ alkyl group, a halo $C_1$-$C_4$ alkoxy group, a vinyl group which optionally comprises a substituent group, an ethynyl group which optionally comprises a substituent group, an aryl group which optionally comprises a substituent group on an aromatic ring, an aryloxy group which optionally comprises a substituent group on an aromatic ring, a benzyl group which optionally comprises a substituent group on a benzene ring, a phenethyl group which optionally comprises a substituent group on a benzene ring, a benzyloxy group which optionally comprises a substituent group on a benzene ring, a benzylsulfanyl group which optionally comprises a substituent group on a benzene ring, a benzylamino group which optionally comprises a substituent group on a benzene ring, a phenyloxymethyl group which optionally comprises a substituent group on a benzene ring, a phenylsulfanylmethyl group which optionally comprises a substituent group on a benzene ring, or a phenylaminomethyl group which optionally comprises a substituent group on a benzene ring;

m represents an integer of 1 or 2; and $Y^1$ and $Y^2$ each independently represent methylene, O or S, with the proviso that $Y^1$ and $Y^2$ do not simultaneously represent S, a pharmaceutically acceptable salt thereof, or a solvate thereof.

5. The compound of claim 1, wherein the compound is selected from the group consisting of:

1-{N-(4-Carboxybutyl)-N-[2-[2-[4-(2-phenylethyl)benzyloxy]phenyl]ethyl]amino}indane-5-carboxylic acid, 5-{N-(4-Carboxybutyl)-N-[2-[2-[4-(2-phenylethyl)benzyloxy]phenyl]ethyl]amino}-5,6,7,8-tetrahydronaphthalene-2-carboxylic acid, 5-{N-(4-Carboxybutyl)-N-[2-[2-[4-(2-phenylethyl)benzyloxy]phenyl]ethyl]amino}-6,7,8,9-tetrahydro-5H-benzocycloheptene-2-carboxylic acid, 4-{N-(4-Carboxybutyl)-N-[2-[2-[4-(2-phenylethyl)benzyloxy]phenyl]ethyl]amino}chromane-7-carboxylic acid, 4-{N-(4-Carboxybutyl)-N-[2-[2-[4-(2-phenylethyl)benzyloxy]phenyl]ethyl]amino}thiochromane-7-carboxylic acid, 5-{N-(4-Carboxybutyl)-N-[2-[2-[4-(2-phenylethyl)benzyloxy]phenyl]ethyl]amino}-5,6,7,8-tetrahydroquinoline-2-carboxylic acid, 3-{N-(4-Carboxybutyl)-N-[2-[2-[4-(2-phenylethyl)benzyloxy]phenyl]ethyl]amino}-2,3-dihydrobenzofuran-6-carboxylic acid, 4-{N-(4-Carboxybutyl)-N-[2-[2-[4-(2-phenylethyl)benzyloxy]phenyl]ethyl]amino}-isochromane-7-carboxylic acid, 5-{N-(4-Carboxybutyl)-N-[2-[2-(2-chlorobenzyloxy)phenyl]ethyl]amino}-5,6,7,8-tetrahydronaphthalene-2-carboxylic acid, 5-{N-[2-[2-(4-Benzyloxybenzyloxy)phenyl]ethyl]-N-(4-carboxybutyl)amino}-5,6,7,8-tetrahydronaphthalene-2-carboxylic acid, 5-{N-[2-[2-(4-Benzylsulfanylbenzyloxy)phenyl]ethyl]-N-(4-carboxybutyl)amino}-5,6,7,8-tetrahydronaphthalene-2-carboxylic acid, 5-{N-(4-Carboxybutyl)-N-[2-[2-(4-phenoxymethylbenzyloxy)phenyl]ethyl]amino}-5,6,7,8-tetrahydronaphthalene-2-carboxylic acid, 5-{N-(4-Carboxybutyl)-N-[2-[2-(4-phenylsulfanylmethylbenzyloxy)phenyl]ethyl]amino}-5,6,7,8-tetrahydronaphthalene-2-carboxylic acid, 5-{N-(4-Carboxybutyl)-N-[2-[2-(4-ethynylbenzyloxy)phenyl]ethyl]amino}-5,6,7,8-tetrahydronaphthalene-2-carboxylic acid, 5-{N-(4-Carboxybutyl)-N-[2-[2-(4-cyclohexylethynylbenzyloxy)phenyl]ethyl]amino}-5,6,7,8-tetrahydronaphthalene-2-carboxylic acid, 5-{N-(4-Carboxybutyl)-N-[2-[2-[4-((E)-2-cyclohexylethenyl)benzyloxy]phenyl]ethyl]amino}-5,6,7,8-tetrahydronaphthalene-2-carboxylic acid, 5-{N-(4-Carboxybutyl)-N-[2-[2-[4-(2-cyclohexylethyl)benzyloxy]phenyl]ethyl]amino}-5,6,7,8-tetrahydronaphthalene-2-carboxylic acid, 5-{N-(4-Carboxybutyl)-N-[2-[2-[trans-4-(2-phenylethyl)cyclohexylmethoxy]phenyl]ethyl]amino}-5,6,7,8-tetrahydronaphthalene-2-carboxylic acid, 5-{N-(4-Carboxybutyl)-N-[2-[2-[cis-4-(2-phenylethyl)cyclohexylmethoxy]phenyl]ethyl]amino}-5,6,7,8-tetrahydronaphthalene-2-carboxylic acid, 5-{N-(4-Carboxybutyl)-N-[2-[2-(5,6,7,8-tetrahydronaphthalene-1-ylmethoxy)phenyl]ethyl]amino}-5,6,7,8-tetrahydronaphthalene-2-carboxylic acid, 5-{N-[2-[2-(3-tert-Butylbenzyloxy)phenyl]ethyl]-N-(4-carboxybutyl)amino}-5,6,7,8-tetrahydronaphthalene-2-carboxylic acid, 5-{N-(4-Carboxybutyl)-N-[2-[2-(4-cyclopropylbenzyloxy)phenyl]ethyl]amino}-5,6,7,8-tetrahydronaphthalene-2-carboxylic acid, 5-{N-(4-Carboxybutyl)-N-[2-[2-(4-isopropylbenzyloxy)phenyl]ethyl]amino}-5,6,7,8-tetrahydronaphthalene-2-carboxylic acid, 5-{N-[2-[2-[(1R)-1-(4-tert-Butylphenyl)ethoxy]phenyl]ethyl]-N-(4-carboxybutyl)amino}-5,6,7,8-tetrahydronaphthalene-2-carboxylic acid, and 5-{N-(4-Carboxybutyl)-N-[2-[2-(indane-5-ylmethoxy)phenyl]ethyl]amino}-5,6,7,8-tetrahydronaphthalene-2-carboxylic acid, a pharmaceutically acceptable salt thereof, or a solvate thereof.

6. A pharmaceutical composition, comprising:
the compound of claim 1, a pharmaceutically acceptable salt thereof, or a solvate thereof; and
a pharmaceutically acceptable carrier.

7. A pharmaceutical composition, comprising:
the compound of claim 3, a pharmaceutically acceptable salt thereof, or a solvate thereof; and
a pharmaceutically acceptable carrier.

8. A pharmaceutical composition, comprising:
the compound of claim 4, a pharmaceutically acceptable salt thereof, or a solvate thereof; and
a pharmaceutically acceptable carrier.

9. A pharmaceutical composition, comprising:
the compound of claim 5, a pharmaceutically acceptable salt thereof, or a solvate thereof; and
a pharmaceutically acceptable carrier.

10. A pharmaceutical composition, comprising:
the compound of claim 2, a pharmaceutically acceptable salt thereof, or a solvate thereof; and
a pharmaceutically acceptable carrier.

* * * * *